United States Patent
Matsui et al.

(10) Patent No.: US 8,167,991 B2
(45) Date of Patent: May 1, 2012

(54) TRISAZO COMPOUND, INK COMPOSITION, RECORDING METHOD, AND COLORED ARTICLE

(75) Inventors: Takahiko Matsui, Kita-ku (JP); Yoshiyuki Dejima, Kita-ku (JP); Takashi Yoshimoto, Kita-ku (JP); Ryoutarou Morita, Kita-ku (JP); Koji Hirota, Kita-ku (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 971 days.

(21) Appl. No.: 12/087,426

(22) PCT Filed: Dec. 28, 2006

(86) PCT No.: PCT/JP2006/326264
§ 371 (c)(1),
(2), (4) Date: Jul. 3, 2008

(87) PCT Pub. No.: WO2007/077931
PCT Pub. Date: Jul. 12, 2007

(65) Prior Publication Data
US 2009/0062545 A1    Mar. 5, 2009

(30) Foreign Application Priority Data

Jan. 6, 2006   (JP) .................. 2006-001453
Jan. 6, 2006   (JP) .................. 2006-001887
Nov. 2, 2006   (JP) .................. 2006-299569
Nov. 8, 2006   (JP) .................. 2006-302514

(51) Int. Cl.
*C09D 11/02* (2006.01)
*C09B 31/16* (2006.01)

(52) U.S. Cl. ............... 106/31.5; 106/31.48; 534/752; 534/754

(58) Field of Classification Search ............. 106/31.5, 106/31.48; 534/752, 754; 427/256; 347/100; 428/195.1
See application file for complete search history.

(56) References Cited

U.S. PATENT DOCUMENTS

| | | | |
|---|---|---|---|
| 4,012,371 A * | 3/1977 | Roueche et al. ............ | 534/752 |
| 7,217,803 B2 * | 5/2007 | Feiler et al. ............... | 534/752 |
| 7,550,037 B2 * | 6/2009 | Mafune et al. ............ | 106/31.48 |
| 7,901,498 B2 * | 3/2011 | Hirota et al. ............. | 106/31.5 |
| 8,080,100 B2 * | 12/2011 | Yoshimoto et al. ......... | 106/31.5 |
| 2005/0200671 A1 * | 9/2005 | Mistry et al. ............. | 347/100 |
| 2006/0053571 A1 * | 3/2006 | Feiler et al. ............... | 8/512 |
| 2011/0050787 A1 * | 3/2011 | Yoshimoto et al. ......... | 347/20 |

FOREIGN PATENT DOCUMENTS

| | | |
|---|---|---|
| DE | 2 004 488 | 8/1971 |
| DE | 2 023 295 | 11/1971 |
| JP | 2002-332426 | 11/2002 |
| JP | 2005-525449 | 8/2005 |
| WO | 2004/050768 | 6/2004 |
| WO | WO 2008/056626 A1 * | 5/2008 |
| WO | WO 2008/096697 A1 * | 8/2008 |

OTHER PUBLICATIONS

International Search Report dated Feb. 20, 2007.

\* cited by examiner

*Primary Examiner* — Helene Klemanski
(74) *Attorney, Agent, or Firm* — Nields, Lemack & Frame, LLC

(57) ABSTRACT

The present invention relates to a trisazo compound represented by the following formula (1) or a salt thereof, The formula (1)

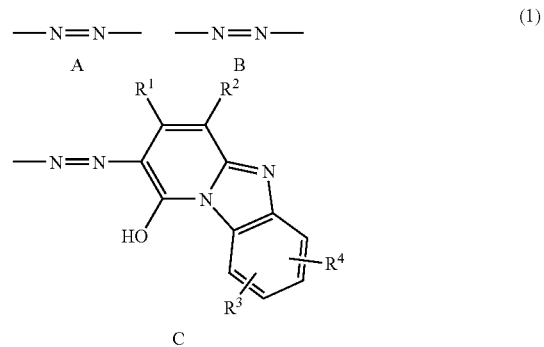

wherein, the group A is a substituted phenyl group, the group B and the group C are substituted para-phenylene groups, $R^1$ represents a C1 to C4 alkyl group which may be substituted by a carboxy group, a phenyl group which may be substituted by a sulfo group, or a carboxy group, $R^2$ represents a cyano group, a carbamoyl group or a carboxy group, each of $R^3$ and $R^4$ independently represents a hydrogen atom, a methyl group, a chlorine atom or a sulfo group, respectively and a water-based black ink composition containing said compound; said compound has high solubility in a medium where the main component is water, its aqueous solution having a high concentration and ink are stable when stored for a long period of time, black-recorded images with it can be provided where both light fastness and ozone gas fastness of the printed images are excellent.

23 Claims, No Drawings

TRISAZO COMPOUND, INK COMPOSITION, RECORDING METHOD, AND COLORED ARTICLE

TECHNICAL FIELD

The present invention relates to a novel trisazo compound or a salt thereof, an ink composition containing these and a colored article therewith.

BACKGROUND ART

In the recording method by means of an ink jet printer which is one of the typical methods among various color recording methods, ink droplets are generated and adhered onto various record-receiving materials (such as paper, film and cloth) to perform recording. This method has been rapidly prevailing lately and is expected to continue growing remarkably in the future because of such features as quietness with less noise generation due to no direct contact of a recording head with a record-receiving material and as easiness in downsizing and speedup. Conventionally, as an ink for fountain pens, felt-tip pens and the like and an ink for inkjet recording, water-based inks where a water-soluble dye is dissolved in an aqueous medium have been used, and in these water-based inks, a water-soluble organic solvent is generally added to prevent ink from clogging at a pen tip or an inkjet nozzle. Therefore, these inks are required to provide recorded images with sufficient density, not to clog at a pen tip or a nozzle, to dry quickly on record-receiving materials, to bleed less, to have excellent storage stability and so on. In addition, a water-soluble dye to be used is required to have high solubility especially in water and in a water-soluble organic solvent to be added to the ink. Further, formed images are required to have image fastnesses such as water fastness, light fastness, ozone gas fastness and moisture fastness.

Among these, the ozone gas fastness means durability against the phenomenon that ozone gas and the like having oxidizing effect, which exist in the air, react with a dye in recording paper to cause discoloration or fading of printed images. Besides ozone gas, oxidizing gases having this type of effect include NOx, SOx and the like, and ozone gas is, among these oxidizing gases, regarded as a main causative substance to further promote the phenomenon of discoloration or fading of inkjet recorded images. Many of ink receiving layers provided on the surfaces of special paper for photo quality inkjet employ a material such as porous white inorganic substance and the like in order to dry ink sooner and to make bleeding less in high image quality, resulting in that on such recording paper, discoloration or fading caused by ozone gas is noticeably observed. As this phenomenon of discoloration or fading caused by ozone gas is a characteristic of inkjet images, improvement of ozone gas fastness is one of important challenges in the inkjet recording method.

In order to extend the use field of the printing method using ink in the future, ink compositions to be used for inkjet recording and colored articles colored therewith are strongly required to have light fastness, ozone gas fastness, moisture fastness and water fastness which are further improved.

While inks with various hues have been prepared from various dyes, black ink among them is an important ink to be used for both mono color and full color images. Many dyes for these black inks have been proposed up to the present, but any product sufficiently satisfying the market requirements has been not provided yet. Many of the proposed coloring matters are azo coloring matters, and among them, disazo coloring matters such as C.I. Food Black 2 have such problems that the optical density of images is low, water fastness and moisture fastness are too low, and light fastness and gas fastness are not sufficient. Polyazo coloring matters where the conjugate system is extended have such problems that bronzing phenomenon having metallic luster is apt to generate partially on recorded images because their water-solubility is generally low, and that light fastness and gas fastness are not sufficient. In addition, in the case of metal-containing azo coloring matter proposed in large numbers as well, some of them have good light fastness but also have such problems that they are not preferable in view of safety to creatures and environment due to containing a metal ion and that ozone gas fastness is extremely poor.

A compound (coloring matter) for black ink for inkjet which has been improved on ozone gas fastness which becomes the most important problem in recent years includes, for example, the compounds described in Patent Literatures 1 and 2. These compounds don't sufficiently satisfy the market requirements on ozone gas fastness and their light fastness is not sufficient, either. In addition, azo compounds having a benzimidazolopyridone skeleton which is a characteristic of the coloring matter compound for black ink of the present invention are described in Patent Literatures 3 to 6 and the like. Patent Literature 4 and 5 disclose trisazo compounds, which have a symmetrical structure where two benzimidazolopyridone skeletons are further bonded to the both ends of a linking group containing an azo structure by an azo structure, and any similar compound to the unsymmetrical trisazo compound of the present invention has not been disclosed yet. Further, there are only a small number of water-soluble compounds and there is no example of their use as a black compound for inkjet ink.

Black inks where yellow to orange dyes are further formulated in a black dye have been proposed, for example, in Patent Literatures 7 to 11, but any product has not been provided yet which sufficiently satisfies the market requirements in terms of print quality, ozone fastness and light fastness.

Patent Literature 12 discloses the compound represented by the following formula (5) which is one of the coloring matter compounds to be used in the present invention.

In addition, a black ink containing two black dyes and yellow to orange dyes is proposed as an ink composition improved on ozone fastness, light fastness and the like, in Patent Literature 13, and it has an excellent hue and color density as black color but has not sufficiently satisfied the recent market requirements yet in terms of the fastnesses (ozone fastness and light fastness).

[Patent Literature 1] JP 2003-183545
[Patent Literature 2] JP 2003-201412
[Patent Literature 3] JP 2006-509068
[Patent Literature 4] DE 2004488
[Patent Literature 5] DE 2023295
[Patent Literature 6] JP H05-134435
[Patent Literature 7] JP H7-122044
[Patent Literature 8] JP 3178200
[Patent Literature 9] JP H9-255906
[Patent Literature 10] JP 2003-286421
[Patent Literature 11] JP 2003-286422
[Patent Literature 12] WO 2006/001274 International Publication Pamphlet
[Patent Literature 13] JP 2005-68416

DISCLOSURE OF THE INVENTION

Problems to be Solved by the Invention

The present invention has an object to provide a coloring matter compound for black ink where it has high solubility in a medium whose main component is water and is stable even when its high concentration aqueous solution and its ink are stored for a long period of time, the density of images printed with it is very high, bronzing is not caused on images even when its high concentration solution is printed on special paper for photo quality inkjet, black-recorded images are allowed to have printed images excellent in fastnesses, particularly both light fastness and ozone gas fastness, and its synthesis is easy and inexpensive; and an ink composition thereof.

In addition, the present invention further has another object to provide a neutral gray to black dye composition with less color by adding (b) a dye having a maximum absorption wavelength in the range of 350 nm to 550 nm and (c) a dye having a maximum absorption wavelength in the range of 560 nm to 660 nm as a dye for color toning, as well as has another object to provide a black ink composition where, by selecting the above dye (b) and dye (c), it is stable even when stored in the state of solution for a long period of time, recorded images obtained by inkjet printing exhibit neutral gray to black with less color, the density of said recorded images is high, no change is caused in the hue of each media, and further, black-recorded images have printed images excellent in fastnesses, particularly both light fastness and ozone gas fastness.

Means of Solving the Problems

The inventors of the present invention have intensively studied a way to solve the above problems and found that a certain trisazo compound can solve the above problems, as well as found that a dye composition exhibiting neutral gray to black with less color can be obtained by means of adding, in said trisazo compound, (b) a dye having a maximum absorption wavelength in the range of 350 nm to 550 nm and (c) a dye having a maximum absorption wavelength in the range of 560 nm to 660 nm as dyes for color toning to make a dye composition containing the three, and further, a water-based black ink composition suitable for inkjet printing where said dye composition in the state of solution has good storage stability, recorded images which have been inkjet printed are excellent in both light fastness and ozone gas fastness is made by means of selecting certain dyes as said (b) and (c), and completed the present invention.

In the connection of the present description, the chemical formulas are shown in free acid form, and if their salts, tautomers and the like exist, said tautomers and the like are also included in the present invention.

That is, the present invention relates to;
(1) A trisazo compound represented by the following formula (1) in free acid form or a salt thereof,

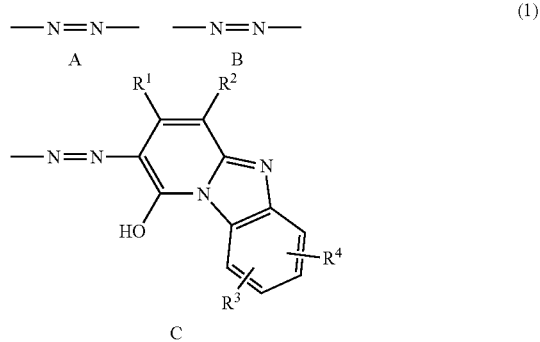

Formula (1)
(wherein, the group A is a substituted phenyl group and has a substituent selected from the group consisting of a carboxy group, a sulfo group, a chlorine atom, a cyano group, a nitro group, a sulfamoyl group, a C1 to C4 alkyl group, a C1 to C4 alkoxy group (which may be substituted by a hydroxy group, a C1 to C4 alkoxy group, a sulfo group or a carboxy group) and a C1 to C4 alkylsulfonyl group (which may be substituted by a hydroxy group, a sulfo group or a carboxy group),
B and C are substituted para-phenylene groups and have a substituent selected from the group consisting of a carboxy group, a sulfo group, a C1 to C4 alkyl group and a C1 to C4 alkoxy group (which may be substituted by a hydroxy group, a C1 to C4 alkoxy group, a sulfo group or a carboxy group),
$R^1$ represents a C1 to C4 alkyl group which may substituted by a carboxy group, a phenyl group which may be substituted by a sulfo group, or a carboxy group,
$R^2$ represents a cyano group, a carbamoyl group or a carboxy group, each of $R^3$ and $R^4$ independently represents a hydrogen atom, a methyl group, a chlorine atom or a sulfo group, respectively),
(2) The trisazo compound or the salt thereof according to the above (1), wherein the substituent of the group A is a sulfo group or a carboxy group and at least one of the substituents on the group B and the group C is a sulfo group or a sulfopropoxy group,
(3) The trisazo compound or the salt thereof according to the above (1), wherein the group B and the group C in the formula (1) are groups represented by the following formula (2),

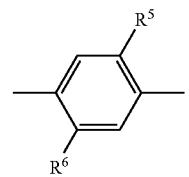

Formula (2)
(wherein, $R^5$ represents a sulfo group or a sulfopropoxy group, and $R^6$ represents a hydrogen atom, a methyl group, an ethyl group, a methoxy group or an ethoxy group, respectively),
(4) The trisazo compound or the salt thereof according to the above (3), wherein in the formula (1), $R^1$ is a methyl group, $R^2$ is a cyano group or a carbamoyl group, $R^3$ is a hydrogen atom, and $R^4$ is a sulfo group,
(5) The trisazo compound or the salt thereof according to the above (3), wherein in the formula (1), the substituent of the group A is a sulfo group or a carboxy group, $R^1$ is a methyl group, $R^2$ is a cyano group or a carbamoyl group, $R^3$ is a hydrogen atom, $R^4$ is a sulfo group, the group B and the group C are represented by the above formula (2), $R^5$ is a sulfo group or a sulfopropoxy group, and $R^6$ is a hydrogen atom or a methyl group,
(6) The trisazo compound or the salt thereof according to the above (3), wherein, in the formula (1), the substituent of the group A is a sulfo group and its substitution position is the para-position to the azo group, $R^1$ is a methyl group, $R^2$ is a cyano group or a carbamoyl group, $R^3$ is a hydrogen atom, $R^4$ is a sulfo group, and the group B and the group C are represented by the above formula (2) where in the group B, $R^5$ is a sulfo group and $R^6$ is a hydrogen atom, and in the group C, $R^5$ is a sulfopropoxy group and $R^6$ is a methyl group,
(7) An ink composition characterized by containing at least one of the trisazo compounds according to any of the above (1) to (6),
(8) An inkjet print recording method characterized by using the ink composition according to the above (7), (9) The inkjet print recording method according to the above (8), wherein a record-receiving material in the inkjet print recording method is a communication sheet,

(10) The inkjet print recording method according to the above (9), wherein the communication sheet is a sheet containing a porous white inorganic substance,

(11) An ink jet printer loading a container containing the ink composition according to the above (10),

(12) A colored article colored with the trisazo compound according to any one of the above (1) to (6) or the ink composition according to the above (7),

(13) The trisazo compound according to the above (1), wherein in the formula (1), at least either one of the group B and the group C is a para-phenylene group substituted by a sulfo C1 to C4 alkoxy group (said phenylene group may be further substituted by a C1 to C4 alkyl group),

(14) The trisazo compound according to the above (13), wherein in the formula (1), at least either one of the group B and the group C is a 2-sulfo C1 to C4 alkoxy-5-C1 to C4 alkyl-1,4-phenylene group,

(15) The trisazo compound according to any of the above (1) to (6) or (13) to (14), wherein, in the formula (1), the group A is a phenyl group which has a sulfo group, a sulfo C1 to C4 alkoxy group or a sulfo C1 to C4 alkylsulfonyl group as one substituent and further, may be substituted by a sulfo group, a carboxy group, a C1 to C4 alkoxy group or a nitro group, or a dicarboxy-substituted phenyl group,

(16) The trisazo compound according to the above (15), wherein in the formula (1), $R^1$ is a C1 to C4 alkyl group (which may be substituted by a carboxy group) or a phenyl group, $R^2$ is a cyano group, a carbamoyl group or a carboxy group, and one of $R^3$ and $R^4$ is a hydrogen atom and the other is a sulfo group,

(17) The trisazo compound according to the above (1) or (13), wherein in the formula (1), the group A is a 4-sulfophenyl group, a 2-carboxy-4-sulfophenyl group, a 2,4- or 2,5-disulfophenyl group, a 4-sulfo C1 to C4 alkoxyphenyl group, a 2-sulfo-4-(nitro or C1 to C4 alkoxy)phenyl group or a 3,5-dicarboxyphenyl group,

(18) The trisazo compound according to the above (17), wherein in the formula (1), both the group B and the group C are 2-sulfo C1 to C4 alkoxy-5-C1 to C4 alkyl-1,4-phenylene groups, $R^1$ is a C1 to C4 alkyl group which may be substituted by a carboxy group, $R^2$ is a cyano group, and one of $R^3$ and $R^4$ is a hydrogen atom and the other is a sulfo group,

(19) The water-based black ink composition according to the above (7), which contains the three of (a) the trisazo compound according to any of the above (1) to (18), (b) a dye having a maximum absorption wavelength in the range of 350 nm to 550 nm and (c) a dye having a maximum absorption wavelength in the range of 560 nm to 660 nm,

(20) The water-based black ink composition according to the above (19), wherein the above (b) a dye having a maximum absorption wavelength in the range of 350 nm to 550 nm and (c) a dye having a maximum absorption wavelength in the range of 560 nm to 660 nm are compounds represented by the following formula (5) and the formula (I-2) or salt thereof, respectively, Formula (5):

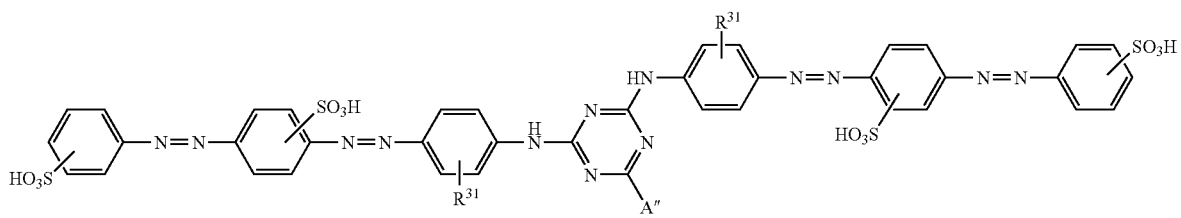

(5)

(wherein, $R^{31}$ represents a hydrogen atom; a hydroxy group; a carboxy group; a C1 to C4 alkyl group which may be substituted by a hydroxy group or a C1 to C4 alkoxy group; a C1 to C4 alkoxy group which may be substituted by a hydroxy group or a C1 to C4 alkoxy group; a C1 to C4 alkylamino group which may be substituted by a hydroxy group or a C1 to C4 alkoxy group; a carboxy C1 to C5 alkylamino group; a bis[carboxy C1 to C5 alkyl]amino group; and a C1 to C4 alkanoylamino group which may be substituted by a hydroxy group or a C1 to C4 alkoxy group; a phenylamino group which may be substituted by a carboxy group, a sulfonic acid group or an amino group; a sulfo group; a halogen atom or a ureide group, and the group A" represents a substituted alkylamino group (the substituent on said alkyl group is a carboxy group or a sulfo group), respectively), Formula (I-2):

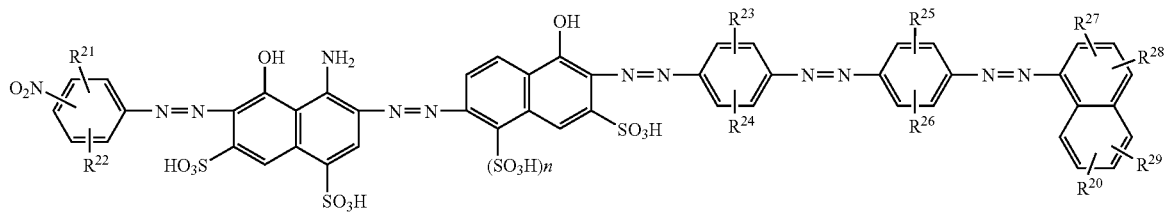

(I-2)

(wherein, each of $R^{21}$ and $R^{22}$ independently represents a hydrogen atom, a halogen atom, a cyano group, a carboxy group, a sulfo group, a sulfamoyl group, an N-alkylaminosulfonyl group, an N-phenylaminosulfonyl group, a C1 to C4 alkylsulfonyl group (which may be substituted by a hydroxy group), a phosphono group, a nitro group, an acyl group, a ureide group, a C1 to C4 alkyl group (which may be substituted by a group selected from the group consisting of a hydroxy group and a C1 to C4 alkoxy group), a C1 to C4 alkoxy group (which may be substituted by a group selected from the group consisting of a hydroxy group, a C1 to C4 alkoxy group, a sulfo group and a carboxy group), an acylamino group, an alkylsulfonylamino group or a phenylsulfonylamino group (the phenyl group may be substituted by a group selected from the group consisting of a halogen atom, an alkyl group and a nitro group), each of $R^{23}$, $R^{24}$, $R^{25}$, $R^{26}$, $R^{27}$, $R^{28}$, $R^{29}$ and $R^{20}$ independently represents a hydrogen atom, a halogen atom, a hydroxy group, a cyano group, a carboxy group, a sulfo group, a sulfamoyl group, an N-alkylaminosulfonyl group, an N-phenylaminosulfonyl group, a C1 to C4 alkylsulfonyl group (which may be substituted by a hydroxy group), a phosphono group, a nitro group, an acyl group, a ureide group, a C1 to C4 alkyl group (which may be substituted by a hydroxy group or a C1 to C4 alkoxy group), a C1 to C4 alkoxy group (which may be substituted by a hydroxy group, a C1 to C4 alkoxy group, a sulfo group or a carboxy group), an acylamino group, an alkylsulfonylamino group or a phenylsulfonylamino group (the phenyl group may be substituted by a halogen atom, an alkyl group or a nitro group), n represents 0 or 1, respectively),

(21) The water-based black ink composition according to the above (19), wherein the above (b) a dye having a maximum absorption wavelength in the range of 350 nm to 550 nm and the above (c) a dye having a maximum absorption wavelength in the range of 560 nm to 660 nm are the compound represented by the formula (5) or the salt thereof according to the above (20) and a compound represented by the formula (II-2) or the salt thereof, respectively, The group B' is the following formula (II-3) or (II-4)

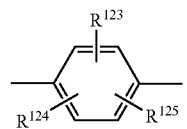

(II-3)

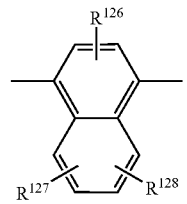

(II-4)

(wherein, each of $R^{123}$, $R^{124}$, $R^{125}$, $R^{126}$, $R^{127}$ and $R^{128}$ independently represents a hydrogen atom, a halogen atom, a hydroxy group, a cyano group, a carboxy group, a sulfo group, a sulfamoyl group, an N-alkylaminosulfonyl group, an N-phenylaminosulfonyl group, a C1 to C4 alkylsulfonyl group (which may be substituted by a hydroxy group), a phosphono group, a nitro group, an acyl group, an ureide group, a C1 to C4 alkyl group (which may be substituted by a hydroxy group or a C1 to C4 alkoxy group), a C1 to C4 alkoxy group (which may be substituted by a group selected from the group consisting of a hydroxy group, a C1 to C4 alkoxy group, a sulfo group or a carboxy group), an acylamino group, an alkylsulfonylamino group or a phenylsulfonylamino group (the phenyl group may be substituted by a group selected from the group consisting of a halogen atom, an alkyl group or a nitro group)),

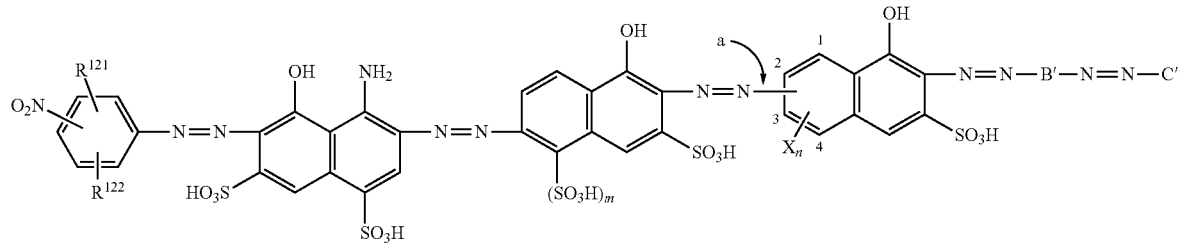

(II-2)

Formula (II-2):
{wherein, each of $R^{121}$ and $R^{122}$ independently represents a hydrogen atom, a halogen atom, a cyano group, a carboxy group, a sulfo group, a sulfamoyl group, an N-alkylaminosulfonyl group, an N-phenylaminosulfonyl group, a C1 to C4 alkylsulfonyl group (which may be substituted by a hydroxy group), a phosphono group, a nitro group, an acyl group, a ureide group, a C1 to C4 alkyl group (which may be substituted by a hydroxy group or a C1 to C4 alkoxy group), a C1 to C4 alkoxy group (which may be substituted by a hydroxy group, a C1 to C4 alkoxy group, a sulfo group or a carboxy group), acylamino group, alkylsulfonylamino group or a phenylsulfonylamino group (the phenyl group may be substituted by a halogen atom, an alkyl group or a nitro group), m represents 0 or 1,
n represents 0 or 1,
X represents a sulfo group, The group C' is a substituted phenyl group or a substituted naphthyl group, and said phenyl group or naphthyl group has a group selected from the group consisting of a hydroxy group, a halogen atom, a cyano group, a carboxy group, a sulfo group, a sulfamoyl group, an N-alkylaminosulfonyl group, an N-phenylaminosulfonyl group, a C1 to C4 alkylsulfonyl group (which may be substituted by a hydroxy group), a phosphono group, a nitro group, an acyl group, a ureide group, a C1 to C4 alkyl group (which may be substituted by a hydroxy group or a C1 to C4 alkoxy group), a C1 to C4 alkoxy group (which may be substituted by a group selected from the group consisting of a hydroxy group, a C1 to C4 alkoxy group, a sulfo group and a carboxy group), an acylamino group, an alkylsulfonylamino group and a phenylsulfonylamino group (the phenyl group may be substituted by a group selected from the group consisting of a halogen atom, an alkyl group or a nitro group), as a substituent),
respectively}.

In addition, the present invention further includes the following invention. It relates to;

(22) The water-based black ink composition according to the above (20), wherein in the formula (1), the substituent of the group A is a sulfo group or a carboxy group and at least one of the substituents on the group B and the group C is a sulfo group or a sulfopropoxy group,

(23) The water-based black ink composition according to the above (20) or (22), wherein in the formula (I-2), $R^{21}$ is a sulfo group or a carboxy group, the substitution position of the nitro group is the para-position to the azo group when the substitution position of $R^{21}$ is the ortho-position to the azo group, the substitution position of the nitro group is the ortho-position to the azo group when the substitution position of $R^{22}$ is the para-position to the azo group, and $R^{22}$ is a hydrogen atom,

(24) The water-based black ink composition according to any of the above (20) and (22) to (23), wherein the compound of the above formula (5) is represented by an azo compound represented by the following formula (I-8)

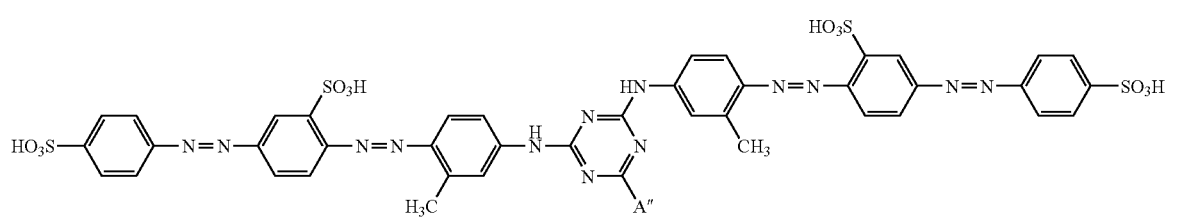

(I-8)

(wherein, the group A" has the same meaning as in the formula (5)) or a salt thereof,

(25) The water-based black ink compositions according to any of the above (20) to (24), wherein in the formula (1), the group A is a substituted phenyl group having 1 to 2 substituents of one or two kinds selected from the group consisting of a sulfo group, a carboxy group, a nitro group and a sulfopropoxysulfonyl group, the group B is a substituted para-phenylene group having 1 to 2 substituents of one or two kinds selected from the group consisting of a sulfo group, a methyl group and a sulfopropoxy group, the group C is a substituted para-phenylene group having 2 substituents of one or two kinds selected from the group consisting of a methyl group, a sulfopropoxy group, a carboxymethoxy group, a sulfoethoxy group and a hydroxyethoxy group, $R^1$ is a group selected from a methyl group, an n-propyl group, a phenyl group, a carboxymethyl group and a t-butyl group, $R^2$ is a group selected from a cyano group, a carbamoyl group and a carboxy group, and one of $R^3$ and $R^4$ is a hydrogen atom and the other is a sulfo group,

(26) The water-based black ink composition according to any of the above (20), and (22) to (25), wherein in a compound represented by the formula (I-2), $R^{21}$ is a sulfo group, the substitution position is the ortho-position to the azo group and the substitution position of the nitro group is the para-position to the azo group; $R^{22}$ is a hydrogen atom; $R^{23}$ and $R^{25}$ are sulfo-substituted C1 to C4 alkoxy groups; $R^{24}$ and $R^{26}$ are C1 to C4 alkyl groups; $R^{27}$ is a hydrogen atom; $R^{28}$ and $R^{29}$ are sulfo groups; $R^{20}$ is a hydroxy group and its substitution position is the peri-position to the azo group; and n is 1,

(27) The water-based black ink composition according to any of the above (20) to (26), wherein the group A" in the formula (5) is a group selected from a sulfoethylamino group, a di(carboxyethyl)amino group, a carboxyethylamino group, a carboxypentylamino group, a sulfomethylamino group, a di(sulfomethyl)amino group, a di(sulfoethyl)amino group, a carboxymethylamino group, a di(carboxymethyl)amino group, a sulfopropylamino group or a di(sulfopropyl)amino group,

(28) The water-based black ink composition according to the above (20), wherein
at least, a compound represented by the formula (1) or a salt thereof, a compound represented by the formula (5) or a salt thereof, and a compound represented by the formula (I-2) or a salt thereof are contained, in the formula (1), the group A is a group selected from a 4-sulfophenyl group, a 2-carboxy-4-sulfophenyl group, a 2-sulfo-4-nitrophenyl group, a 4-sulfopropylsulfonyl group, a 3,5-dicarboxyphenyl group, a 2,5-disulfophenyl group, a 2,4-disulfophenyl group, a 4-sulfopropoxy group and a 2-sulfo-4-methoxyphenyl group when the azo group binding to the group B is at the 1-position; the group B is a 2-sulfo-1,4-phenylene group or a 2-sulfopropoxy-5-methyl-1,4-phenylene group when the azo group binding to the group C is at the 1-position; the group C is a 2-sulfopropoxy-5-methyl-1,4-phenylene group or a 2,5-dihydroxyethoxy-1,4-phenylene group when the azo group not binding to the group B is at the 1-position; $R^1$ is a group selected from a methyl group, an n-propyl group, a carboxymethyl group, a phenyl group and a t-butyl group; $R^2$ is a group selected from a cyano group, a carbamoyl group and a carboxy group; $R^3$ is a hydrogen atom; and $R^4$ is a sulfo group,
in the formula (5), $R^{31}$ is a methyl group, and the group A" is a group selected from a sulfoethylamino group, a di(carboxyethyl)amino group, a carboxyethylamino group, a carboxypentylamino group, a sulfomethylamino group, a di(sulfomethyl)amino group, a di(sulfoethyl)amino group, a carboxymethylamino group, a di(carboxymethyl)amino group, a sulfopropylamino group or a di(sulfopropyl)amino group, and
in the formula (I-2), $R^{21}$ is a group selected from a sulfo group, a carboxy group and a cyano group, the nitro group is at the para-position when the substitution position of $R^{21}$ is the ortho-position to the azo group, and the nitro group is at the ortho-position when the substitution position of $R^{21}$ is the para-position; $R^{22}$ is a hydrogen atom; as for $R^{23}$ and $R^{24}$, when the azo group binding to the substituted naphthalene is at the 1-position, $R^{23}$ is a 3-sulfopropoxy group at the 2-position and $R^{24}$ is a methyl group at the 5-position; as for $R^{25}$ and $R^{26}$, when the azo group binding to the substituted naphthalene is at the 1-position, $R^{25}$ is a group selected from a 3-sulfopropoxy group, a 2-hydroxyethoxy group and a carboxymethoxy group, at the 3-position and $R^{26}$ is a hydrogen atom, a methyl group or a 2-hydroxyethoxy group, at the 6-position; as for $R^{20}$ and $R^{27}$ to $R^{29}$, $R^{27}$ is a hydrogen atom, $R^{28}$ and $R^{29}$ are sulfo groups, $R^{20}$ is a sulfo group or a hydroxy group; and n is 1,

(29) The water-based black ink composition according to the above (20), wherein
at least, a compound represented by the formula (1) or a salt thereof, a compound represented by the formula (5) or a salt thereof, and a compound represented by the formula (I-2) or a salt thereof are contained,
in the formula (1), the group A is a group selected from a 4-sulfophenyl group, a 2-carboxy-4-sulfophenyl group, a 2-sulfo-4-nitrophenyl group, a 3,5-dicarboxyphenyl group, a 2,5-disulfophenyl group, a 2,4-disulfophenyl group, a 4-sulfopropoxy group and a 2-sulfo-4-methoxyphenyl group when the azo group binding to the group B is at the 1-position; the group B is a 2-sulfo-1,4-phenylene group or a 2-sulfopropoxy-5-methyl-1,4-phenylene group when the azo group binding to the group C is at the 1-position; the group C is a 2-sulfopropoxy-5-methyl-1,4-phenylene group when the azo group not binding to the group B is at the 1-position; $R^1$ is a group selected from a methyl group, an n-propyl group and a phenyl group; $R^2$ is a cyano group or a carbamoyl group; $R^3$ is a hydrogen atom; and $R^4$ is a sulfo group,
in the formula (5), $R^{31}$ is a methyl group, the group A'' is a sulfoethylamino group or a di(carboxymethyl)amino group, and
in the formula (I-2), $R^{21}$ is a sulfo group, the nitro group is at the para-position when the substitution position of $R^{21}$ is at the ortho-position to the azo group, and the nitro group is at the ortho-position when the substitution position of $R^{21}$ is at the para-position; $R^{22}$ is a hydrogen atom; as for $R^{23}$ and $R^{24}$, when the azo group binding to the substituted naphthalene is at the 1-position, $R^{23}$ is a 3-sulfopropoxy group at the 2-position and $R^{24}$ is a methyl group at the 5-position; as for $R^{25}$ and $R^{26}$, when the azo group binding to the substituted naphthalene is at the 1-position, $R^{25}$ is a 3-sulfopropoxy group at the 3-position and $R^{26}$ is a methyl group at the 6-position; as for $R^{27}$ to $R^{29}$ and $R^{20}$, when the azo group is at the 1-position, $R^{27}$ is a hydrogen atom, $R^{28}$ is a sulfo group at the 3-position or the 4-position, $R^{29}$ is a sulfo group at the 6-position, and $R^{20}$ is a hydroxy group at the 8-position; and n is 1,
(30) An inkjet recording method using the water-based black ink composition according to any one of the above (20) and (22) to (29),
(31) The inkjet recording method according to the above (30), wherein a record-receiving material in the inkjet print recording method is a communication sheet,
(32) The inkjet recording method according to the above (31), wherein the communication sheet contains a porous white inorganic substance,
(33) An ink jet printer loading a container containing the water-based black ink composition according to any one of the above (20) and (22) to (29),
(34) A colored article colored with the water-based black ink composition according to any one of the above (20) and (22) to (29),
(35) The water-based black ink composition according to the above (21), wherein the compounds of the above formula (1) and formula (II-2), and a dye having a maximum absorption wavelength in the range of 350 nm to 550 nm are contained,
(36) The water-based black ink composition according to the above (21) or the above (35), wherein the above formula (1), the substituent of the group A is a sulfo group or a carboxy group, and at least one of the substituents of the group B and the group C is a sulfo group or a sulfopropoxy group,
(37) The water-based black ink composition according to any one of the above (21), (35) and (36), wherein the binding position of Bond a in the above formula (II-2) is the 2-position or the 3-position, the substitution position of X is the 3-position when the binding position of Bond a is the 2-position, and the substitution position of X is the 4-position when the binding position of Bond a is the 3-position,
(38) The water-based black ink composition according to any one of the above (21) and (35) to (37), wherein an azo dye represented by the above formula (5) or a salt thereof is contained at least in free acid form as a dye having a maximum absorption wavelength in the range of 350 nm to 550 nm,
(39) The water-based black ink composition according to any one of the above (21) and (35) to (37), wherein
a condensation dye (BB) of 4,4'-dinitrostilbene-2,2'-disulfonic acid of the formula (II-6) described later with a compound represented by the formula (II-7) described later and (CC) a dye obtained by reduction of (BB) are contained, in free acid from, as dyes having a maximum absorption wavelength in the range of 350 nm to 550 nm,
(40) The water-based black ink composition according to any one of the above (21) and (35) to (38), wherein the compound of the above formula (5) is an azo compound represented by the above formula (I-8) or a salt thereof,
(41) The water-based black ink composition according to any one of the above (21) and (35) to (40), wherein the dye having a maximum absorption wavelength in the range of 350 nm to 550 nm is a mixture of at least one kind of azo compound represented by the above formula (5) or a salt thereof and at least one of dyes represented by (BB) or (CC) described later,
(42) The water-based black ink composition according to the above (21) or (35), wherein the dye having a maximum absorption wavelength in the range of 350 nm to 550 nm is C.I. Direct Yellow 132 or C.I. Direct Yellow 86,
(43) The water-based black ink composition according to the above (21) or (35), wherein in the compound represented by the formula (1), the group A is a substituted phenyl group having 1 to 2 substituents of one or two kinds selected from the group consisting of a sulfo group, a carboxy group, a nitro group and a sulfopropoxysulfonyl group; the group B is a substituted para-phenylene group having 1 to 2 substituents of one or two kinds selected from the group consisting of a sulfo group, a methyl group or a sulfopropoxy group; the group C is a substituted para-phenylene group having 2 substituents of one or two kinds selected from the group consisting of a methyl group, a sulfopropoxy group, a carboxymethoxy group, a sulfoethoxy group and hydroxyethoxy group; $R^1$ is a group selected from a methyl group, an n-propyl group, a phenyl group, a carboxymethyl group and a t-butyl group; $R^2$ is a group selected from a cyano group, a carbamoyl group and a carboxy group; and one of $R^3$ and $R^4$ is a hydrogen atom and the other is a sulfo group,
(44) The water-based black ink composition according to the above (21) or (35), wherein, in the compound represented by the formula (II-2), $R^{121}$ is a sulfo group or a methoxy group substituted at the ortho-position to the azo group, the substitution position of the nitro group is the para-position to the azo group, and $R^{122}$ is a hydrogen atom or a sulfo group substituted at the para-position to $R^{121}$; otherwise $R^{121}$ is a sulfo group substituted at the para-position to the azo group, the substitution position of the nitro group is the ortho-position to the azo group, and $R^{122}$ is a hydrogen atom; m is 1; n is 0 or 1; X is a sulfo group at the 4-position when the substitution position of Bond a is the 3-position, and X is a sulfo group at the 3-position when the substitution position of Bond a is the 2-position; $R^{123}$ is a group selected from a sulfo group, a sulfopropoxy group and a carboxymethoxy group, at the meta-position to the azo group binding to the group C' when the group B' is represented by the formula (II-3); $R^{124}$ is a hydrogen atom; $R^{125}$ is a hydrogen atom or a methyl group substituted at the para-position to $R^{123}$; $R^{126}$ and $R^{127}$ are hydrogen atoms when the group B' is represented by the formula (II-4); $R^{128}$ is a sulfo group substituted at the 6-position or the 7-position when the azo group binding to the group C' is the 1-position; the group C' is a group selected from a 4-hydroxyethylsulfophenyl, a 4-sulfophenyl, a 2-carboxy-4-sulfophenyl, a 4-methoxy-3-sulfophenyl, a 4-sulfonaphthyl-1-yl, a 4,8-disulfonaphthyl-2-yl, a 8-hydroxy-3,6-disulfonaphthyl-1-yl and a 6-nitro-4,8-disulfonaphthyl-2-yl,

(45) The water-based black ink composition according to the above (38), wherein the group A" represented by the formula (5) is a group selected from a sulfoethylamino group, a di(carboxyethyl)amino group, a carboxyethylamino group, a carboxypentylamino group, a sulfomethylamino group, a di(sulfomethyl)amino group, a di(sulfoethyl)amino group, a carboxymethylamino group, a di(carboxymethyl)amino group, a sulfopropylamino group and di(sulfopropyl)amino group,

(46) The water-based black ink composition according to the above (39), wherein in the compound represented by the formula (II-7), each of $R^{41}$ and $R^{42}$ is independently a group selected from a hydrogen atom, a methyl group and a methoxy group, and each of $R^{43}$ to $R^{45}$ is independently a group selected from a hydrogen atom, a carboxy group, a sulfo group, a methoxy group and a hydroxy group,

(47) An inkjet recording method, wherein the water-based black ink composition according to any one of the above (19), (21) and (35) to (46) is used,

(48) The inkjet recording method according to the above (47), wherein a record-receiving material in the inkjet print recording method is a communication sheet,

(49) The inkjet recording method according to the above (48), wherein the communication sheet contains a porous white inorganic substance,

(50) The ink jet printer loading a container containing the ink composition according to any one of the above (19), (21) and (35) to (46),

(51) A colored article colored with the water-based black ink composition according to any one of the above (21) and (35) to (46),

(52) The water-based black ink composition according to the above (19), wherein (b) the dye having a maximum absorption wavelength in the range of 350 nm to 550 nm is a compound represented by the above formula (5), respectively.

(53) The trisazo compound according to the above (1), wherein in the formula (1), the group A is a 2,4-disulfophenyl group, both the group B and the group C are 2-(3-sulfopropoxy)-5-methyl-1,4-phenylene groups, $R^1$ is a methyl group, $R^2$ is a cyano group, one of $R^3$ and $R^4$ is a hydrogen atom and the other is a sulfo group,

(54) The water-based black ink composition according to the above (19) or (53), wherein (b) the dye having a maximum absorption wavelength in the range of 350 nm to 550 nm is the above formula (5),

(55) The water-based black ink composition according to claim 19, wherein (c) the dye having a maximum absorption wavelength in the range of 560 nm to 660 nm is a compound represented by the above formula (I-2) or a salt thereof.

Effect of the Invention

The trisazo compound of the formula (1) of the present invention and a tautomer thereof or their salts (hereinafter, these are referred to as the trisazo compound merely for simplicity) have excellent water-solubility, and therefore provide good filtration property by a membrane filter in the process of producing its ink composition as well as excellent stability in storage of its recording liquid and excellent jet stability. In addition, the ink composition of the present invention containing this trisazo compound has good storage stability, exhibiting no crystal precipitation, no change in physical properties and color, nor the like after storage for a long period of time. Further, the ink composition containing the trisazo compound of the present invention can be suitably used for inkjet recording and writing tools; the print density of recorded images in the case of recording on plain paper and inkjet special paper with it is extremely high; bronzing does not occurred on the images where printing is performed with its high concentration solution; and it has various excellent fastnesses, especially both light fastness and ozone gas fastness. Using it together with ink compositions using magenta, cyan and yellow dyes provides various excellent fastnesses and allows full-color inkjet recording excellent in storage properties. The ink composition of the present invention is thus extremely useful as a black ink for inkjet recording

BEST MODE FOR CARRYING OUT THE INVENTION

Hereinafter, the present invention will be specifically explained.

The terms "alkyl" "alkoxy" "acyl" and the like in the present description mean, unless otherwise noted in particular, to have about 1 to 20 carbon atoms, preferably 1 to 10 carbon atoms, and more preferably 1 to 4 carbon atoms.

The present invention includes its tautomers if they exist, the trisazo compound represented by the formula (1) is expected to have tautomers represented by the following formula (3) and (4), and these compounds are included in the present invention.

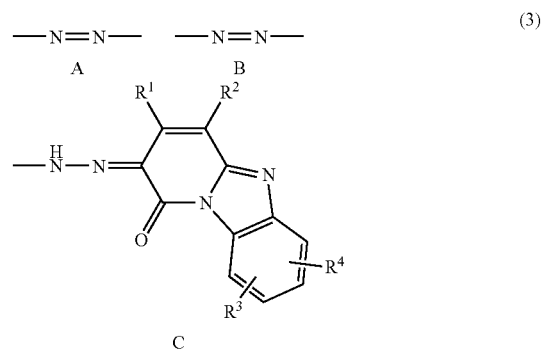

(wherein, the group A, the group B, the group C and $R^1$ to $R^4$ have the same meanings as in the formula (1))

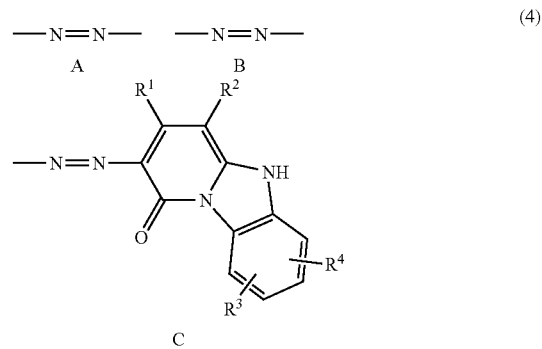

(wherein, the group A, the group B, the group C and $R^1$ to $R^4$ have the same meanings as in the formula (1))

As for the substituents of the group A, the group B, and the group C in the formula (1), examples of the C1 to C4 alkyl group include, for example, methyl, ethyl, n-propyl, isopropyl, n-butyl, isobutyl, sec-butyl, tert-butyl and the like.

The C1 to C4 alkyl group on the group B and the group C are preferably methyl or ethyl, and more preferably methyl.

As for $R^1$ in the formula (1), examples of the C1 to C4 alkyl group which may be substituted by a carboxy group include, for example, methyl, ethyl, n-propyl, isopropyl, n-butyl, isobutyl, sec-butyl, tert-butyl, carboxymethyl, 2-carboxyethyl and the like. Preferable is methyl or ethyl and more preferable is methyl.

As for the substituents of the group A, the group B, the group C in the formula (1), examples of the C1 to C4 alkoxy group which may be substituted by a hydroxy group, a C1 to C4 alkoxy group, a sulfo group or a carboxy group include, for example, methoxy, ethoxy, n-propoxy, isopropoxy, n-butoxy, sec-butoxy, tert-butoxy, 2-hydroxyethoxy, 2-hydroxypropoxy, 3-hydroxypropoxy, methoxyethoxy, ethoxyethoxy, n-propoxyethoxy, isopropoxyethoxy, n-butoxyethoxy, methoxypropoxy, ethoxypropoxy, n-propoxypropoxy, isopropoxybutoxy, n-propoxybutoxy, 2-hydroxyethoxyethoxy, carboxymethoxy, 2-carboxyethoxy, 3-carboxypropoxy, 3-sulfopropoxy, 4-sulfobutoxy and the like.

As for the substituents of the group A in the formula (1), examples of the C1 to C4 alkylsulfonyl group which may be substituted by a hydroxy group, a sulfo group and a carboxy group include, for example, methylsulfonyl, ethylsulfonyl, propylsulfonyl, butylsulfonyl, hydroxyethylsulfonyl, 2-hydroxypropylsulfonyl, 2-sulfoethylsulfonyl, 3-sulfopropylsulfonyl, 2-carboxyethylsulfonyl, 3-carboxypropylsulfonyl and the like.

As for $R^1$ in the formula (1), examples of the phenyl group which may be substituted by a sulfo group include, for example, phenyl, 3-sulfophenyl, 4-sulfophenyl, 2,4-disulfophenyl, 3,5-disulfophenyl and the like.

Preferable substituents of the group A in the formula (1) are cyano, carboxy, sulfo, sulfamoyl, C1 to C4 alkylsulfonyl (for example, methylsulfonyl), hydroxy C1 to C4 alkylsulfonyl (for example, 2-hydroxyethylsulfonyl), sulfo C1 to C4 alkylsulfonyl (for example, 3-sulfopropylsulfonyl), nitro, C1 to C4 alkyl (for example, methyl and ethyl), C1 to C4 alkoxy (for example, methoxy and ethoxy), hydroxy C1 to C4 alkoxy (for example, 2-hydroxyethoxy), sulfo C1 to C4 alkoxy (for example, 2-sulfoethoxy, 3-sulfopropoxy and 4-sulfobutoxy), carboxy C1 to C4 alkoxy (for example, carboxymethoxy and 2-carboxyethoxy). More preferable are cyano, carboxy, sulfo, sulfamoyl, C1 to C4 alkylsulfonyl (for example, methylsulfonyl), hydroxy C1 to C4 alkylsulfonyl (for example, 2-hydroxyethylsulfonyl), sulfo C1 to C4 alkylsulfonyl (for example, 3-sulfopropylsulfonyl), nitro or/and C1 to C4 alkoxy. In addition, optionally, carboxy, sulfo, sulfo C1 to C4 alkylsulfonyl, nitro, C1 to C4 alkoxy or/and sulfo C1 to C4 alkoxy are more preferable. Further preferable are carboxy, sulfo, C1 to C4 alkoxy or/and sulfo C1 to C4 alkoxy. Most preferable are carboxy or/and sulfo. These substituents may be one or plural, and they may be the same or different when they are plural. The preferable number of the substituent is 1 or 2, the substitution position is the para-position to the azo group when it is 1, and the substitution positions are the ortho-position and the para-position or they are the meta-positions when it is 2. The group A can preferably include, for example, 4-sulfophenyl, 2-carboxy-4-sulfophenyl, 2,4- or 2,5-disulfophenyl, 4-sulfo C1 to C4 alkoxyphenyl, 2-sulfo-4-(nitro or C1 to C4 alkoxy)phenyl or 3,5-dicarboxyphenyl (when the bond position of the azo group is 1).

Preferable substituents of the group B and the group C as the para-phenylene group in the formula (1) include carboxy, sulfo, C1 to C4 alkyl (for example, methyl and ethyl), C1 to C4 alkoxy (for example, methoxy and ethoxy), hydroxy C1 to C4 alkoxy (for example, 2-hydroxyethoxy), sulfo C1 to C4 alkoxy (for example, 2-sulfoethoxy, 3-sulfopropoxy and 4-sulfobutoxy) and carboxy C1 to C4 alkoxy (for example, carboxymethoxy and 2-carboxyethoxy). More preferably, sulfo, methyl, methoxy, 2-hydroxyethoxy, 2-sulfoethoxy, 3-sulfopropoxy or carboxymethoxy are cited. Further preferable are sulfo, methyl, methoxy or 3-sulfopropoxy. The group B and the group C have 1 to 3 of these substituents, preferably 1 to 2. The group B and the group C preferably include the groups represented by the above formula (2). A preferable combination of $R^5$ and $R^6$ as substituents is that $R^5$ is sulfo and $R^6$ is a hydrogen atom, or that $R^5$ is 3-sulfopropoxy and $R^6$ is methyl.

In this connection, the group B and the group C may be the same or different.

$R^1$ in the formula (1) is preferably methyl, ethyl, n-propyl, n-butyl, t-butyl, carboxymethyl, phenyl, 4-sulfophenyl or carboxy, more preferably methyl, n-propyl, carboxymethyl or 4-sulfophenyl, and further preferably methyl or n-propyl.

A preferable combination of $R^1$ and $R^2$ in the formula (1) is that $R^1$ is methyl and $R^2$ is cyano or that $R^1$ is methyl and $R^2$ is a carbamoyl group.

$R^3$ and $R^4$ in the formula (1) are preferably hydrogen atom(s), methyl(s), sulfo(s). A preferable combination of $R^3$ and $R^4$ is that one of them is a hydrogen atom and the other is sulfo.

The salt of the trisazo compound represented by the above formula (1) is a salt with an inorganic or organic cation. Of them, specific examples of the inorganic salt include an alkali metal salt, an alkali earth metal salt and an ammonium salt. Preferable inorganic salts are salts of lithium, sodium and potassium, and an ammonium salt. In addition, the above organic cation includes, for example, a quaternary ammonium ion represented by the following formula (I-11), but not limited thereto. Further, a free acid, a tautomer thereof and their salts may be a mixture. For example, any combination may be employed, such as a mixture of sodium salt and ammonium salt, a mixture of free acid and sodium salt and a mixture of lithium salt, sodium salt and ammonium salt. Physical property values of solubility and the like can differ depending on the kind of salt, so a mixture having intended physical properties can be also obtained by selecting a kind of salt appropriately if needed, or by changing, if a plural of salts and the like are contained, the rate of the salts.

(I-11)

Each of $Z^1$, $Z^2$, $Z^3$ and $Z^4$ in the formula (I-11) independently represents a group selected from the group consisting of a hydrogen atom, an alkyl group, a hydroxyalkyl group and a hydroxyalkoxyalkyl group. As for $Z^1$, $Z^2$, $Z^3$ and $Z^4$ in the formula (I-11), specific examples of the alkyl group include methyl, ethyl, n-propyl, isopropyl, n-butyl, isobutyl, sec-butyl and tert-butyl, specific examples of the hydroxyalkyl group include hydroxy C1 to C4 alkyl groups such as hydroxymethyl, hydroxyethyl, 3-hydroxypropyl, 2-hydroxypropyl, 4-hydroxybutyl, 3-hydroxybutyl, and 2-hydroxybutyl groups, examples of hydroxyalkoxyalkyl group include hydroxy C1 to C4 alkoxy C1 to C4 alkyl groups such as hydroxyethoxymethyl, 2-hydroxyethoxyethyl, 3-hydroxyethoxypropyl, 2-hydroxyethoxypropyl, 4-hydroxyethoxybutyl, 3-hydroxyethoxybutyl and 2-hydroxyethoxybutyl, and preferably a hydroxyethoxy C1 to C4 alkyl group among them. Particularly preferable are a hydrogen atom; methyl; a hydroxy C1 to C4 alkyl group such as hydroxymethyl, hydroxyethyl, 3-hydroxypropyl, 2-hydroxypropyl, 4-hydroxybutyl, 3-hydroxybutyl and 2-hydroxybutyl; and a hydroxyethoxy C1 to C4 alkyl group such as hydroxyethoxymethyl, 2-hydroxyethoxyethyl, 3-hydroxyethoxypropyl, 2-hydroxyethoxypropyl, 4-hydroxyethoxybutyl, 3-hydroxyethoxybutyl and 2-hydroxyethoxybutyl.

Specific examples of $Z^1$, $Z^2$, $Z^3$ and $Z^4$ in the formula (I-11) are shown in Table 1.

TABLE 1

| Compound No. | $Z^1$ | $Z^2$ | $Z^3$ | $Z^4$ |
|---|---|---|---|---|
| 1-1 | H | $CH_3$ | $CH_3$ | $CH_3$ |
| 1-2 | $CH_3$ | $CH_3$ | $CH_3$ | $CH_3$ |
| 1-3 | H | $-C_2H_4OH$ | $-C_2H_4OH$ | $-C_2H_4OH$ |
| 1-4 | $CH_3$ | $-C_2H_4OH$ | $-C_2H_4OH$ | $-C_2H_4OH$ |
| 1-5 | H | $-CH_2CH(OH)CH_3$ | $-CH_2CH(OH)CH_3$ | $-CH_2CH(OH)CH_3$ |
| 1-6 | $CH_3$ | $-CH_2CH(OH)CH_3$ | $-CH_2CH(OH)CH_3$ | $-CH_2CH(OH)CH_3$ |
| 1-7 | H | $-C_2H_4OH$ | H | $-C_2H_4OH$ |
| 1-8 | $CH_3$ | $-C_2H_4OH$ | H | $-C_2H_4OH$ |
| 1-9 | H | $-CH_2CH(OH)CH_3$ | H | $-CH_2CH(OH)CH_3$ |
| 1-10 | $CH_3$ | $-CH_2CH(OH)CH_3$ | H | $-CH_2CH(OH)CH_3$ |
| 1-11 | $CH_3$ | $-C_2H_4OH$ | $CH_3$ | $-C_2H_4OH$ |
| 1-12 | $CH_3$ | $-CH_2CH(OH)CH_3$ | $CH_3$ | $-CH_2CH(OH)CH_3$ |

The trisazo compound of the present invention represented by the formula (1) can be synthesized by, for example, the following process. In this connection, the structural formula of the compound in each process is shown in free acid form.

A compound represented by the following formula (6)

$$A\text{-}NH_2 \tag{6}$$

(wherein, the group A has the same meaning as in the formula (1)) is diazotized in a conventional manner, and then reacted with a compound represented by the following formula (7)

$$B\text{—}NH_2 \tag{7}$$

(wherein, the group B represents a phenyl group corresponding to the group B in the formula (1)) for coupling reaction in a conventional manner to obtain a compound represented by the following formula (8)

$$A\text{-}N{=}N\text{—}B\text{—}NH_2 \tag{8}$$

(wherein, the group A and the group B have the same meanings as in the formula (1)). The obtained compound of the formula (8) is diazotized in a conventional manner, and then reacted with a compound represented by the following formula (9)

$$C\text{—}NH_2 \tag{9}$$

(wherein, the group C represents a phenyl group corresponding to the group C in the formula (1)) for coupling reaction in a conventional manner to obtain a compound represented by the following formula (10)

$$A\text{-}N{=}N\text{—}B\text{—}N{=}N\text{—}C\text{—}NH_2 \tag{10}$$

(wherein, the group A, the group B and the group C have the same meanings as in the formula (1)). The obtained compound of the formula (10) is diazotized in a conventional manner, and then reacted with a compound represented by the following formula (11)

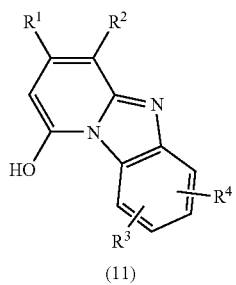

Formula (11)

(11)

(wherein, $R^1$ to $R^4$ have the same meanings as in the formula (1)) for coupling reaction in a conventional manner to obtain a trisazo compound of the present invention represented by the formula (1). In addition, the compound represented by the formula (11) can be synthesized in accordance with the method described in Patent Literature 4.

Suitable specific examples of the compound of the present invention represented by the formula (1) are not limited, but can include compounds represented by the following formulas. The sulfo groups and the carboxy groups in the tables are shown in free acid form.

TABLE 2

| Compound No. | Structural Formula |
|---|---|
| 1 | |

TABLE 2-continued
| Compound No. | Structural Formula |
|---|---|
| 2 | 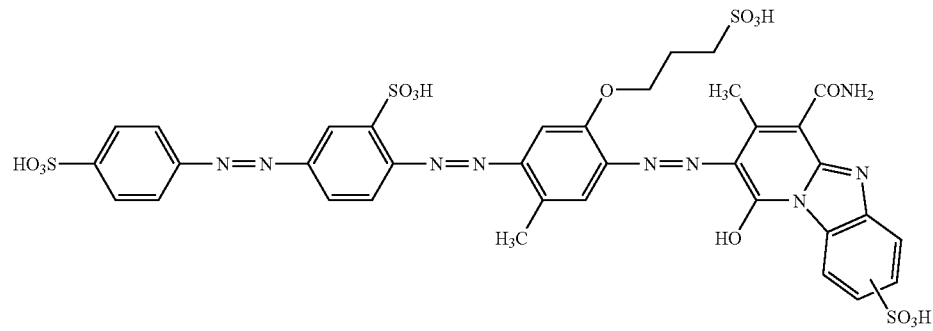 |
| 3 | 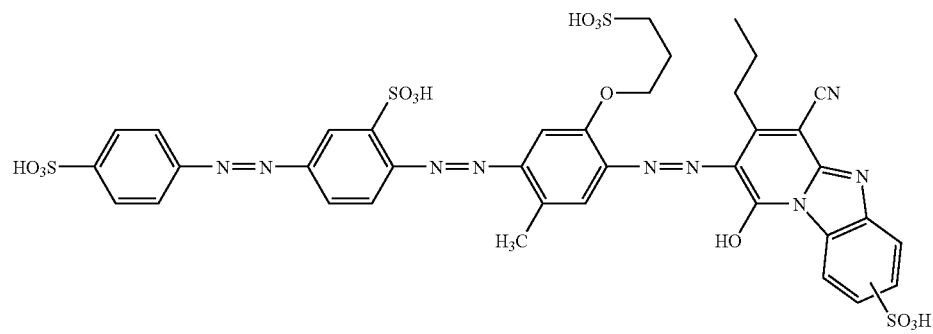 |
| 4 | 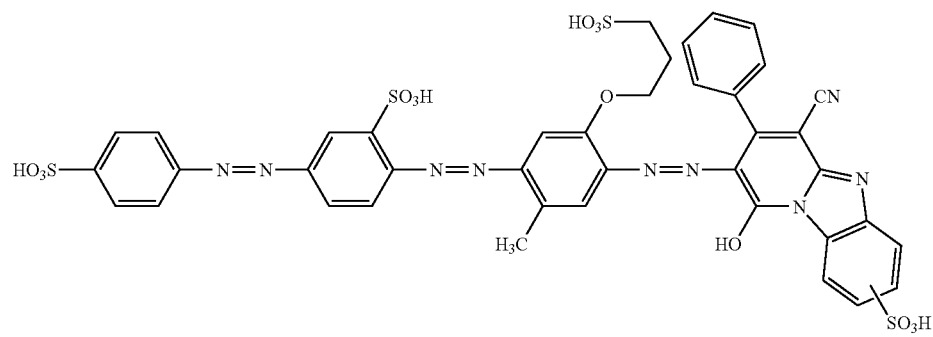 |
| 5 | 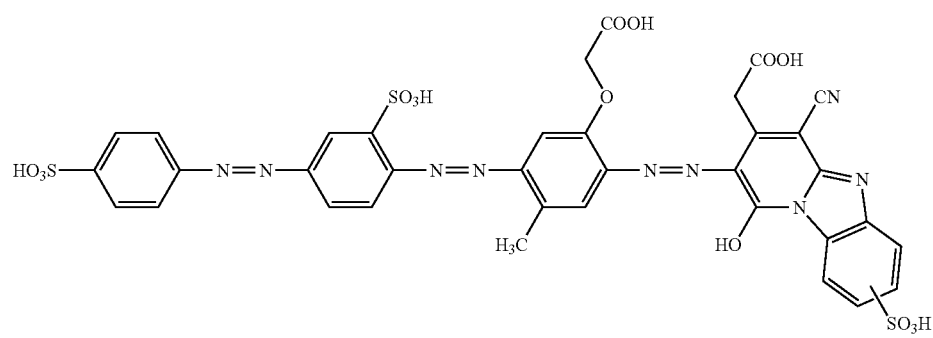 |

TABLE 2-continued
| Compound No. | Structural Formula |
|---|---|
| 6 | 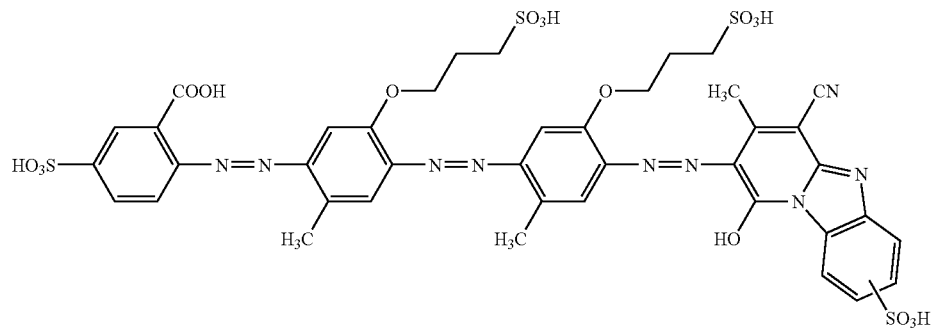 |
TABLE 3
| Compound No. | Structural Formula |
|---|---|
| 7 | 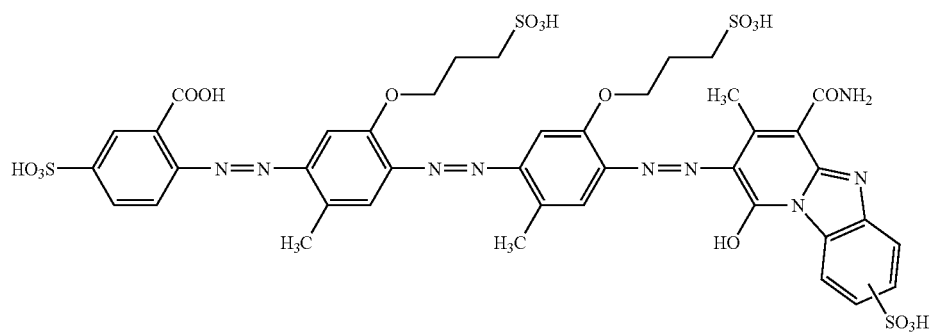 |
| 8 | 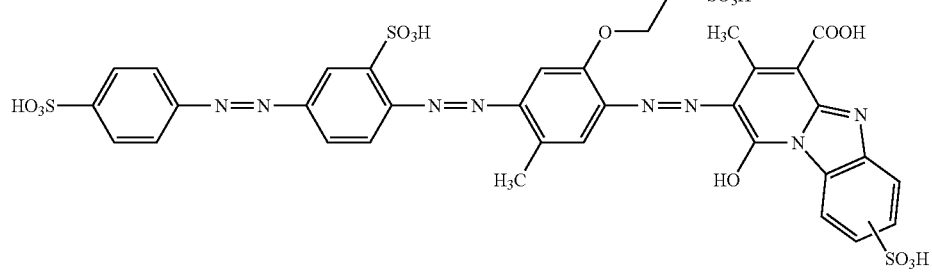 |
| 9 | 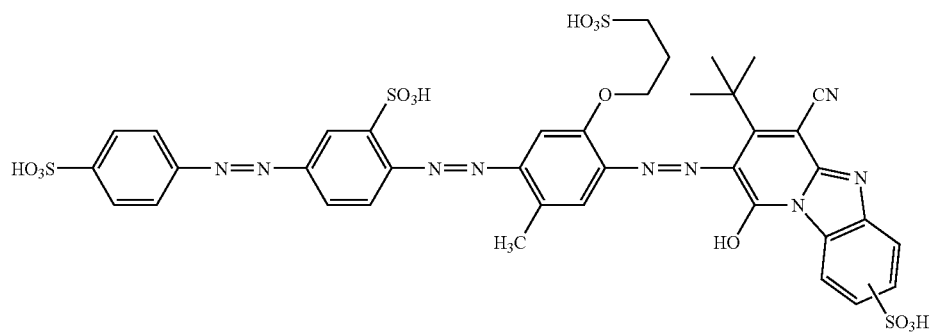 |

TABLE 3-continued

| Compound No. | Structural Formula |
|---|---|
| 10 | (structure) |
| 11 | (structure) |
| 12 | (structure) |

Other than the examples in the above tables 2 and 3, preferable specific examples of the compound represented by the above formula (1) are shown in the following tables 6 and 7. The present invention is, however, not limited thereto.

TABLE 6

| Compound No. | Structural Formula |
|---|---|
| 13 | (structure) |

TABLE 6-continued
| Compound No. | Structural Formula |
| --- | --- |
| 14 | 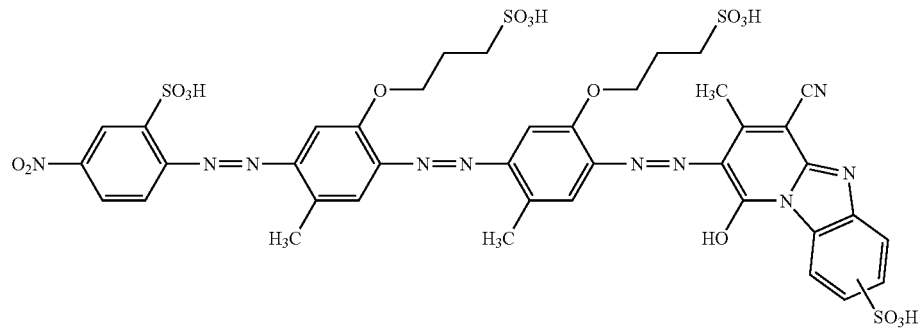 |
| 15 | 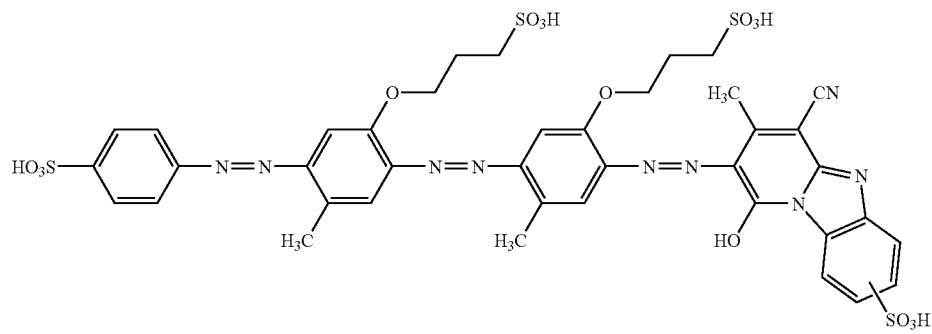 |
| 16 | 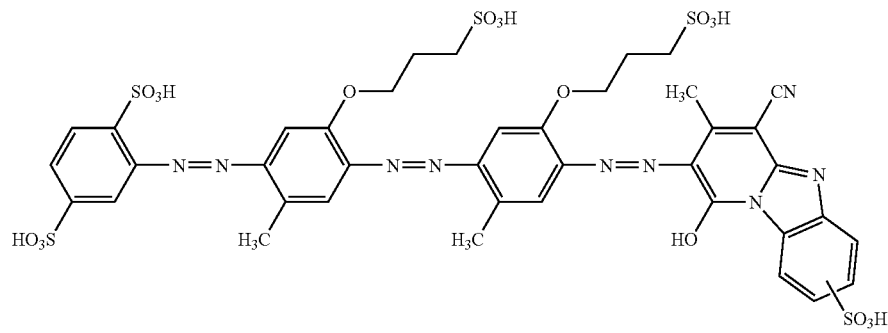 |
| 17 | 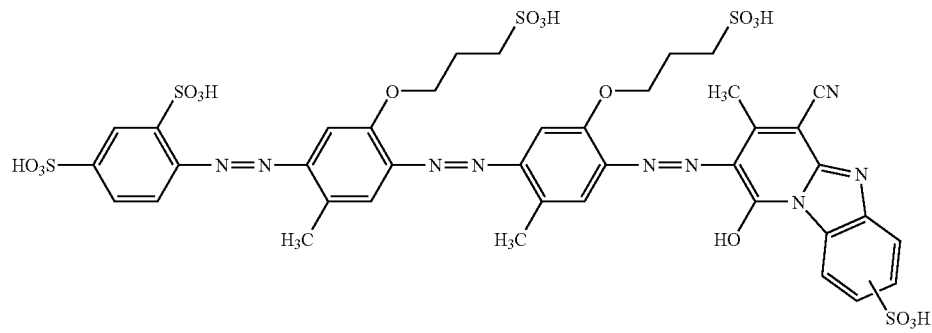 |

TABLE 7

| Compound No. | Structural Formula |
|---|---|
| 18 | (structure) |
| 19 | (structure) |
| 20 | (structure) |

The diazotization of the compound of the formula (6) is carried out by a known method per se. It is carried out, for example, in an inorganic acid medium at a temperature of, for example, −5 to 30° C., preferably 5 to 15° C., using a nitrite salt, for example, an alkali metal nitrite such as sodium nitrite. The coupling of the diazotized compound of the compound of the formula (6) with the compound of the formula (7) is carried out in known conditions per se. It is advantageously carried out in water or an aqueous organic medium (a mixed solvent of water and a water soluble or miscible organic solvent) at a temperature of, for example, −5 to 30° C., preferably 0 to 25° C. and an acidic to neutral pH value, for example, pH 1 to 6. The adjustment to the above pH value is preferably carried out by addition of a base because the diazotized reaction solution is acidic and the inside of the reaction system becomes further acidified as the progress of the coupling reaction. As the base, for example, an alkali metal hydroxide such as lithium hydroxide or sodium hydroxide, an alkali metal carbonate such as lithium carbonate, sodium carbonate or potassium carbonate, an acetate salt such as sodium acetate, ammonia, organic amine or the like can be used. The compound of the formula (6) and the compound of the formula (7) are used in approximately stoichiometric amounts.

The diazotization of the compound of the formula (8) is carried out by a known method per se. It is carried out, for example, in an inorganic acid medium, at a temperature of, for example, −5 to 40° C., preferably 5 to 30° C., using a nitrite salt, for example, an alkali metal nitrite such as sodium nitrite. The coupling of the diazotized compound of the compound of the formula (8) with the compound of the formula (9) is carried out in known conditions per se. It is advantageously carried out in water or an aqueous organic medium at a temperature of, for example, −5 to 40° C., preferably 10 to 30° C. and an acidic to neutral pH value, for example, pH 2 to 7. The adjustment of the pH of the reaction solution to the pH value in preferable conditions is preferably carried out by addition of a base because the diazotized reaction solution is acidic and the inside of the reaction system becomes further acidic as the progress of the coupling reaction. As the base, for example, an alkali metal hydroxide such as lithium hydroxide or sodium hydroxide, an alkali metal carbonate such as lithium carbonate, sodium carbonate and potassium carbonate, an acetate salt such as sodium acetate, ammonia, organic amine or the like can be used. The compound of the formula (8) and the compound of the formula (9) are used in approximately stoichiometric amounts.

The diazotization of the compound of the formula (10) is carried out by a known method per se, for example, in an inorganic acid medium at a temperature of, for example, −5 to 40° C., preferably 10 to 30° C., using a nitrite salt, for example, an alkali metal nitrite such as sodium nitrite. The coupling of the diazotized compound of the compound of the formula (10) with the compound of the formula (11) is carried out in known conditions per se. It is advantageously carried out in water or an aqueous organic medium at a temperature of, for example, −5 to 50° C., preferably 10 to 30° C., and a weakly acidic to alkaline pH value. It is preferably carried out at a weakly acidic to weakly alkaline pH value, for example, pH 6 to 10, and the adjustment of the pH value is carried out by addition of a base. As the base, for example, an alkali metal hydroxide such as lithium hydroxide or sodium hydroxide, an alkali metal carbonate such as lithium carbonate, sodium carbonate or potassium carbonate, an acetate salt such as sodium acetate, ammonia, organic amine or the like can be used. The compounds of the formulas (10) and (11) are used in approximately stoichiometric amounts.

In order to convert the trisazo compound represented by the formula (1) of the present invention to a desired salt, after the coupling reaction, a desired inorganic salt or organic cation salt is added to the reaction solution for salting out; otherwise the reaction solution is isolated in free acid form by addition of a mineral acid, which is then washed, if needed, using water, acidified water, an aqueous organic medium and the like to remove an inorganic salt, followed by neutralization with an desired inorganic or organic base in an aqueous medium to give a solution of a corresponding salt. Acidic water here means water acidified by dissolving, for example, a mineral acid such as sulfuric acid and hydrochloric acid or an organic acid such as acetic acid in water. Aqueous organic medium means water-miscible organic substances, so-called water-miscible organic solvents and the like (its specific examples include a water-soluble organic solvent described later and the like, while organic substances which are not classified usually into a solvent can be also used as long as they are water-miscible, if needed) containing water. Examples of the inorganic salt include an alkali metal salt such as lithium chloride, sodium chloride or potassium chloride, and an ammonium salt such as ammonium chloride or ammonium bromide, and examples of the organic cation salt include a halogen salt of quaternary ammoniums represented by the above formula (I-11) and the like. Examples of the inorganic base include, for example, a hydroxide of an alkali metal such as lithium hydroxide, sodium hydroxide or potassium hydroxide, an ammonium hydroxide, a carbonate of an alkali metal such as lithium carbonate, sodium carbonate or potassium carbonate, and the like, examples of the organic base include organic amine, for example, quaternary ammoniums represented by the above formula (I-11) such as diethanolamine and triethanolamine, but not limited thereto.

The ink composition of the present invention will be explained. An aqueous composition containing the trisazo compound represented by the above formula (1) of the present invention can dye materials composed of cellulose. In addition, it can also dye other materials having a carbonamide bond and used widely for dyeing leather, textile fabric and paper. On the other hand, a typical use of the compound of the present invention includes a dye composition where said compound is dissolved in a liquid medium, particularly an ink composition.

A reaction solution containing the trisazo compound of the present invention represented by the above formula (1), for example, the reaction solution in (3) of Example 1-1 described later and the like can be used directly for production of an ink composition. However, firstly this is dried, for example, by spray-drying for isolation; or an inorganic salt such as sodium chloride, potassium chloride, calcium chloride or sodium sulfate are added to said reaction solution for salting out or an mineral acid such as hydrochloric acid, sulfuric acid or nitric acid is added for aciding out; or salting-aciding out which is a combination of the above salting out and aciding out is conducted in order to take out the trisazo compound of the present invention, which can be then used for preparing an ink composition.

The ink composition of the present invention is a composition whose main medium is water, where the trisazo compound represented by the formula (1) of the present invention is contained in an amount of typically 0.1 to 20% by mass, preferably 1 to 10% by mass, more preferably 2 to 8% by mass and the rest is water, an aqueous organic solvent or the like. The ink composition of the present invention may further contain a water-soluble organic solvent in an amount of, for example, 0 to 30% by mass and an ink preparation agent in an amount of, for example, 0 to 10%, preferably 0 to 7%, and optionally 0 to 5% by mass. In addition, other dyes may be contained for the purpose of color toning and the like, if desired. In this connection, the pH of the ink composition is preferably pH 5 to 11, and more preferably pH 7 to 10, in terms of improvement of storage stability. Further, the surface tension of the ink composition is preferably 25 to 70 mN/m, and more preferably 25 to 60 m N/m. Furthermore, the viscosity of the ink composition is preferably 30 mPa·s or less, and more preferably 20 mPa·s or less. The pH and the surface tension of the ink composition of the present invention can be accordingly adjusted with the pH adjuster and the surfactant described later.

The ink composition of the present invention is an ink composition where the trisazo compound represented by the above formula (1) is dissolved in water or a water-soluble organic solvent (a water-miscible organic solvent), if needed, together with other dyes for color toning and the like, and if needed, an ink preparation agent are added thereto.

One of preferable ink compositions includes an water-based black dye composition containing (a) the trisazo compound represented by the above formula (1) as well as both (b) a dye having a maximum absorption wavelength in the range of 350 nm to 550 nm (having a hue of yellow to red or brown: hereinafter, also referred to as a brown dye) and (c) a dye having a maximum absorption wavelength in the range of 560 nm to 660 nm (hereinafter, also referred to as a blue-tinted dye for convenience in the present invention) for color toning. In this case, the ratio of the three dyes can be accordingly adjusted for use, depending on the dyes to be used, and usually so adjusted that the dyes are contained in the range of, based on the total (mass) of the three, (a) the trisazo compound represented by the above formula (1) in an amount of 5 to 85% by mass (hereinafter, % is the same unless otherwise noted in particular), preferably 5 to 60%, a brown dye of (b) in an amount of 5 to 85%, preferably 5 to 60% by mass, and a blue-tinted dye of (c) in an amount of 10 to 90%, preferably 10 to 80%, in order to make a total of 100%. A more preferable ratio of the three is approximately, based on the total of the three, (a) the trisazo compound represented by the above formula (1) in an amount of 15 to 70%, a brown dye of (b) 10 to 65%, and a blue-tinted dye of (c) 20 to 75%.

As the dye of (b), any dye can be used as long as it has a maximum absorption wavelength in the range of 350 nm to 550 nm. This dye has a hue of yellow to red or brown. The range of the maximum absorption wavelength of this dye is preferably in a shorter wavelength than the maximum absorption wavelength of the compound of the general formula (1). The range of the maximum absorption wavelength of the compound of the general formula (1) to be used here in the present invention is approximately from 530 nm to 570 nm, so the range of the maximum absorption wavelength of the above dye having a hue of yellow to red or brown is more preferably approximately 380 nm to 500 nm.

A general dye having a color index number can be used as the above dye having a maximum absorption wavelength ($\lambda$max) in the range of 350 nm to 550 nm, and its specific examples include C.I. Direct Yellow 132 ($\lambda$max: about 405 nm), C. I. Direct Yellow 86 ($\lambda$max: about 370 nm) and the like.

However, more preferably, the compounds described in the following (1) and (2) or salts thereof can be cited.

More preferable compounds are compounds of the following formula (5) described in the following (1).

In this connection, in the present description, all the chemical structural formulas are shown in free acid form and mean they can be also salts thereof.

(1) A compound represented by the following formula (5)

tuted alkylamino group (the substituent on said alkyl group is a carboxy group or a sulfo group), respectively) or a salt thereof, or (2) A condensation dye (BB) of 4,4'-dinitrostilbene-2,2'-disulfonic acid of the following formula (II-6) with an aminobenzenes, preferably a monoazo compound represented by the following (II-7) and a dye (CC) obtained by reduction of (BB) can be cited.

The compound of the formula (II-6)

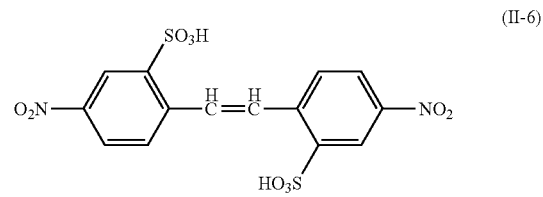

The compound of the formula (II-7)

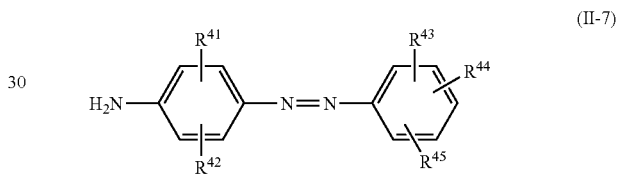

(wherein, each of $R^{41}$ to $R^{45}$ independently represents a hydrogen atom; a halogen atom; a hydroxy group; a sulfo

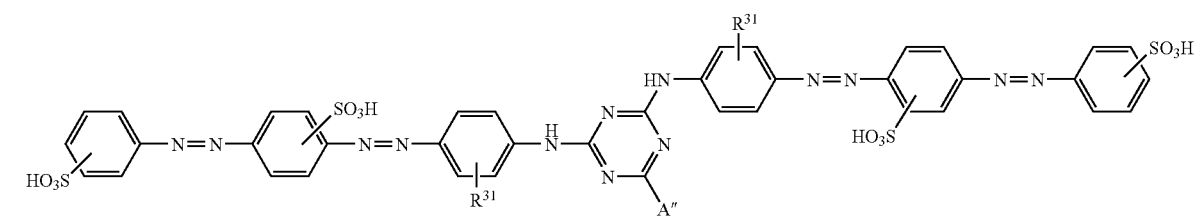

(wherein, $R^{31}$ represents a hydrogen atom; a hydroxy group; a carboxy group; a C1 to C4 alkyl group which may be substituted by a hydroxy group or a C1 to C4 alkoxy group; a C1 to C4 alkoxy group which may be substituted by a hydroxy group or a C1 to C4 alkoxy group; a C1 to C4 alkylamino group which may be substituted by a hydroxy group or a C1 to C4 alkoxy group; a carboxy C1 to C5 alkylamino group; a bis(carboxy C1 to C5 alkyl)amino group; a C1 to C4 alkanoylamino group which may be substituted by a hydroxy group or a C1 to C4 alkoxy group; a phenylamino group which may be substituted by a carboxy group, a sulfonic acid group and an amino group; a sulfo group; a halogen atom or a ureide group, and the group A" represents a substigroup; a carboxy group; a C1 to C4 alkyl group; and a C1 to C4 alkoxy group)

Specific examples of the above condensation dye (BB) include C.I. Direct Orange 62 ($\lambda$max: about 494 nm) and the like. In addition, synthesis of dyes corresponding to the dye BB and the dye CC is described in Synthesis Examples II-13 to II-15 described later. Of these, 1 or several kinds may be used in combination, but not limited.

The dye of (b) is more preferably a compound of the above formula (5) or a salt thereof. Most preferable compound as the formula (5) is a compound represented by the following formula (I-8)

(I-8)

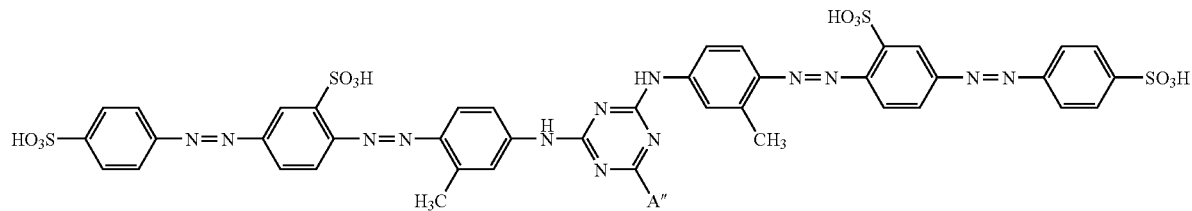

(wherein, the group A" has the same meaning as in the formula (5)) or a salt thereof.

The dye (c) (blue-tinted dye) having a maximum absorption wavelength in the range of 560 nm to 660 nm preferably has a maximum absorption wavelength in the longer wavelength side than that of the compound of the formula (1). The range of the maximum absorption wavelength of the compound of the formula (1) is, as described above, approximately from 530 nm to 570 nm, so the range of the maximum absorption wavelength of the blue-tinted dye is, more preferably approximately from 570 nm to 660 nm.

In addition, (c) the dye having a maximum absorption wavelength in the range of 560 nm to 660 nm can preferably include a compound of the following formula (I-2) or a salt thereof, or a compound of the following formula (II-2) or a salt thereof.

The compound of the formula (I-2)

alkoxy group (which may be substituted by a group selected from the group consisting of a hydroxy group, a C1 to C4 alkoxy group, a sulfo group and a carboxy group), an acylamino group, an alkylsulfonylamino group or a phenylsulfonylamino group (the phenyl group may be substituted by a group selected from the group consisting of a halogen atom, an alkyl group and a nitro group), each of $R^{23}$, $R^{24}$, $R^{25}$, $R^{26}$, $R^{27}$, $R^{28}$, $R^{29}$ and $R^{20}$ independently represents a hydrogen atom, a halogen atom, a hydroxy group, a cyano group, a carboxy group, a sulfo group, a sulfamoyl group, an N-alkylaminosulfonyl group, an N-phenylaminosulfonyl group, a C1 to C4 alkylsulfonyl group (said alkyl group may be substituted by a hydroxy group), a phosphono group, a nitro group, an acyl group, a ureide group, a C1 to C4 alkyl group (said alkyl group may be (I-2)

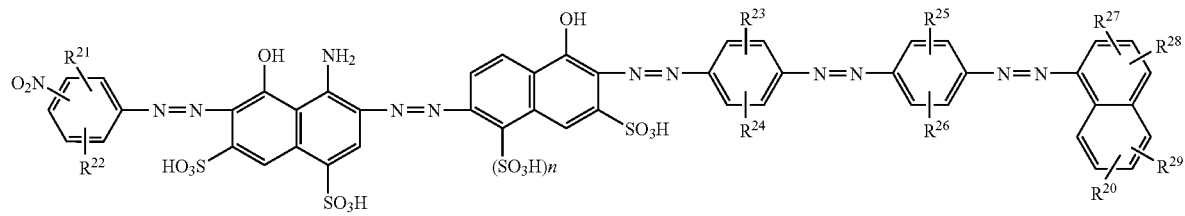

(wherein, each of $R^{21}$ and $R^{22}$ independently represents a hydrogen atom, a halogen atom, a cyano group, a carboxy group, a sulfo group, a sulfamoyl group, an N-alkylaminosulfonyl group, an N-phenylaminosulfonyl group, a C1 to C4 alkylsulfonyl group which may be substituted by a hydroxy group, a phosphono group, a nitro group, an acyl group, a ureide group, a C1 to C4 alkyl group (which may be substituted by a group selected from the group consisting of a hydroxy group and a C1 to C4 alkoxy group), a C1 to C4 substituted by a hydroxy group or a C1 to C4 alkoxy group), a C1 to C4 alkoxy group (said alkoxy group may be substituted by a hydroxy group, a C1 to C4 alkoxy group, a sulfo group or a carboxy group), an acylamino group, an alkylsulfonylamino group or a phenylsulfonylamino group (the phenyl group may be substituted by a halogen atom, an alkyl group or a nitro group); and n represents 0 or 1, respectively)

The compound of the formula (II-2)

(II-2)

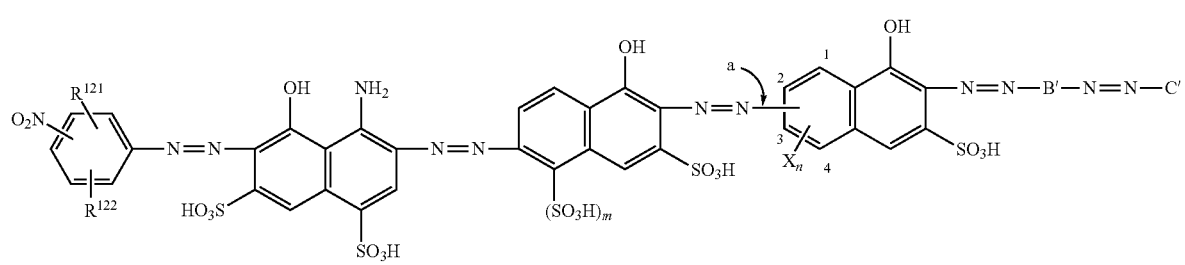

(wherein, $R^{121}$, $R^{122}$, m, n, X, the group B' and the group C' have the same meanings as above, respectively)

Next, the preferable compound of the above formula (5) as the dye (b) (brown dye) having a maximum absorption wavelength in the range of 350 nm to 550 nm will be explained.

2-hydroxy-n-propionylamino, 3-hydroxy-n-propionylamino, 2-methoxy-n-propionylamino, 3-methoxy-n-propionylamino, 2-hydroxy-n-butyrylamino, 3-hydroxy-n-butyrylamino, 2-methoxy-n-butyrylamino, 3-methoxy-n-butyrylamino and the like.

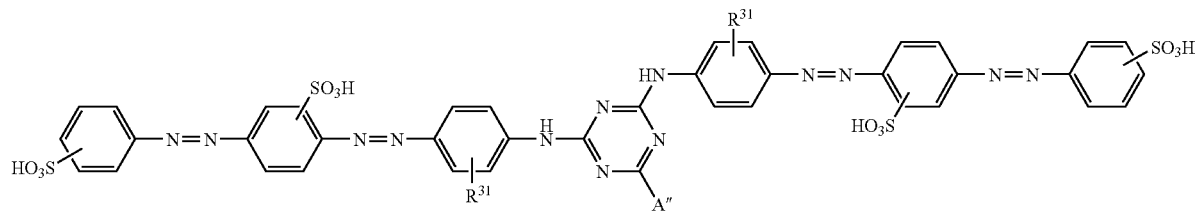

(5)

In the compound represented by the above formula (5), $R^{31}$ represents a hydrogen atom; a hydroxy group; a carboxy group; a C1 to C4 alkyl group which may be substituted by a hydroxy group or a C1 to C4 alkoxy group; a C1 to C4 alkoxy group which may be substituted by a hydroxy group or a C1 to C4 alkoxy group; a C1 to C4 alkylamino group which may be substituted by a hydroxy group or a C1 to C4 alkoxy group; a carboxy C1 to C5 alkylamino group; a bis(carboxy C1 to C5 alkyl)amino group; a C1 to C4 alkanoylamino group which may be substituted by a hydroxy group or a C1 to C4 alkoxy group; a phenylamino group where the phenyl group may be substituted by a carboxy group, a sulfo group or an amino group; a sulfo group; a halogen atom or a ureide group.

Specific examples of the C1 to C4 alkyl group where $R^{31}$ in the above formula (5) may be substituted by a hydroxy group or a C1 to C4 alkoxy group include methyl, ethyl, n-propyl, isopropyl, n-butyl, isobutyl, sec-butyl, t-butyl, methoxyethyl, ethoxyethyl, n-propoxyethyl, isopropoxyethyl, n-butoxyethyl, sec-butoxyethyl, tert-butoxyethyl, 2-hydroxyethyl or the like.

Examples of the C1 to C4 alkoxy group where $R^{31}$ in the above formula (5) may be substituted by a hydroxy group or a C1 to C4 alkoxy group include methoxy, ethoxy, n-propoxy, isopropoxy, n-butoxy, sec-butoxy, t-butoxy, 2-hydroxyethoxy, 2-hydroxypropoxy, 3-hydroxypropoxy, methoxyethoxy, ethoxyethoxy, n-propoxyethoxy, isopropoxyethoxy, n-butoxyethoxy, methoxypropoxy, ethoxypropoxy, n-propoxypropoxy, isopropoxybutoxy, n-propoxybutoxy, 2-hydroxyethoxyethoxy or the like.

Examples of the C1 to C4 alkylamino group where $R^{31}$ in the above formula (5) may be substituted by a hydroxy group or a C1 to C4 alkoxy group include methylamino, ethylamino, n-propylamino, isopropylamino, n-butylamino, isobutylamino, N,N-dimethylamio, N,N-diethylamino, N,N-di(n-propylamino), N,N-di(isopropyl)amino, hydroxyethylamino, 2-hydroxypropylamino, 3-hydroxypropylamino, bis(hydroxyethyl)amino, methoxyethylamino, ethoxyethylamino, bis(metoxyethyl)amino, bis(2-ethoxyethyl)amino or the like.

Examples where $R^{31}$ in the above formula (5) is a carboxy C1 to C5 alkylamino group include carboxymethylamino, carboxyethylamino, carboxypropylamino, carboxy-n-butylamino, carboxy-n-pentylamino and the like.

Examples of the bis(carboxy C1 to C5 alkyl)amino group include bis(carboxymethyl)amino, bis(carboxyethyl)amino, bis(carboxypropyl)amino and the like.

Examples of the C1 to C4 alkanoylamino group where $R^{31}$ in the above formula (5) may be substituted by a hydroxy group or a C1 to C4 alkoxy group include acetylamino, n-propionylamino, isopropionylamino, hydroxyacetylamino, Examples where $R^{31}$ in the above formula (5) is the phenylamino group (the phenyl may be substituted by a carboxy group, sulfo group or an amino group) include phenylamino, sulfophenylamino, carboxyphenylamino, biscarboxyphenylamino, aminophenylamino, diaminophenylamino, diaminosulfophenylamino and the like.

$R^{31}$ is preferably a C1 to C4 alkyl group, particularly preferably a methyl group.

The substitution position of said $R^{31}$ can be either the ortho-position or the meta-position, preferably the meta-position, to the binding position of the amino group binding to the triazine ring.

The group A″ in the above formula (5) is a substituted alkylamino group, and the substituent on the alkyl group is a carboxy group or a sulfo group. Specifically, a mono C1 to C5 alkylamino group or a di C1 to C5 alkylamino group having a carboxy group or a sulfo group is cited, such as a sulfo C1 to C5 alkylamino group (amino C1 to C5 alkyl sulfonic acid), a di(sulfo C1 to C5 alkyl)amino group (diimino C1 to C5 alkyl sulfonic acid), a carboxy C1 to C5 alkylamino group (amino C1 to C5 alkylcarboxylic acid) or a di(carboxy C1 to C5 alkyl)amino group (diimino C1 to C5 alkylcarboxylic acid), and more preferable is one having a sulfo group. The carbon atom number of the alkyl group is preferably 1 to 3, and more preferably 1 to 2. Its specific examples preferably include sulfoethylamino or di(carboxymethyl)amino, and sulfoethylamino is particularly preferred. In addition, this group A″ is the same in the above formula (I-8), and preferable groups in the formula (5) are also preferred in the formula (I-8).

The compounds represented by the formulas (5) and (1-8) exist either in free acid form or in a form of salt thereof and can be in any form of them. Their preferable salts and the like can be the same as in the above formula (1), however, when the organic cation forming the salts is the above formula (I-11), each of $Z^1$, $Z^2$, $Z^3$ and $Z^4$ particularly in the formula (I-11) is independently, preferably, a hydrogen atom, an alkyl group, a hydroxy C1 to C4 alkyl group or a hydroxy C1 to C4 alkoxy C1 to C4 alkyl group. When it is an inorganic cation, they are the same, including the preferable ones, as in the above formula (1).

The azo compound represented by the above formula (5) can be synthesized by, for example, the following method. In addition, the structural formula of the compound of in each process is shown in free acid form.

In this connection, the substituent $R^{31}$ in the following formulas (I-31) to (I-33) has the same meaning as in the above formula (5).

For example, firstly, a cyanuric chloride is reacted with a compound represented by the following formula (I-31) to obtain a compound represented by the following formula (I-32).

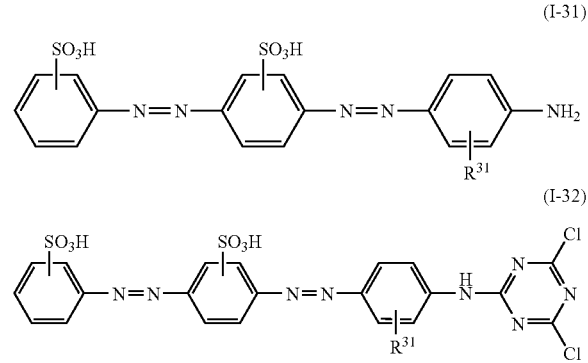

The compound of the above formula (I-31) is further condensed with the obtained compound of the above formula (I-32) to obtain a compound represented by the following formula (I-33).

Preferable examples of the group A" in the above formula (5) include substituted alkylamino groups having a structure shown in the following Table I-7. The group A" is, however, not limited thereto.

Table I-7

TABLE I-7

| No. | Substituted Alkylamino Group |
|---|---|
| 3-1 | NH(CH$_2$)$_2$SO$_3$H |
| 3-2 | NH((CH$_2$)$_2$COOH)$_2$ |
| 3-3 | NH(CH$_2$)$_2$COOH |
| 3-4 | NH(CH$_2$)$_5$COOH |
| 3-5 | NH(CH$_2$SO$_3$H) |
| 3-6 | N(CH$_2$SO$_3$H)$_2$ |
| 3-7 | N((CH$_2$)$_2$SO$_3$H)$_2$ |
| 3-8 | NH(CH$_2$COOH) |
| 3-9 | N(CH$_2$COOH)$_2$ |
| 3-10 | N((CH$_2$)$_2$COOH)$_2$ |
| 3-11 | NH(CH$_2$)$_3$SO$_3$H |
| 3-12 | N((CH$_2$)$_3$SO$_3$H)$_2$ |

Next, the condensation dye (BB) of 4,4'-dinitrostilbene-2,2'-disulfonic acid of the above formula (II-6) with the monoazo compound represented by the above (II-7) and the dye (CC) obtained by reduction of (BB) in (2) in regard to the dye (b) (having a hue of yellow to red or brown; also referred

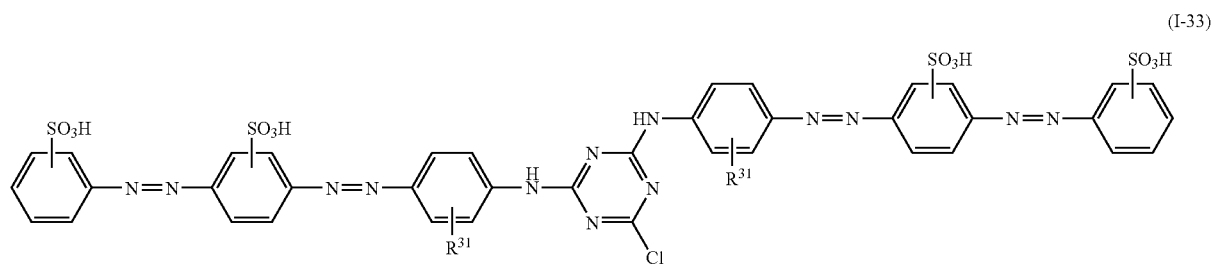

Subsequently, in alkaline conditions, the above formula (I-33) is condensed with a substituted alkylamine corresponding to the group A" to obtain a compound of the above formula (5) where the chlorine atom on the cyanuric ring is converted to said substituted alkylamino group.

The reaction of the compound of the above formula (I-31) with a cyanuric chloride (the first condensation) is carried out in known conditions per se. For example, it is carried out, for example, in an aqueous or organic medium at a temperature of, for example, 0 to 40° C., preferably 0 to 30° C. and at pH 1 to 7, preferably pH 3 to 7. In the reaction of the compound of the formula (I-31) with the cyanuric chloride, the both are used in approximately stoichiometric amounts.

The reaction of the compound of the above formula (I-31) with the compound of the formula (I-32) (the second condensation) is carried out in known conditions per se. It is carried out in an aqueous or organic medium at a temperature of, for example, 10 to 60° C., preferably 20 to 45° C., and at pH 3 to 10, preferably pH 6 to 8. In the reaction of the compounds of the formulas (I-31) with (I-32), the both are used in approximately stoichiometric amounts.

The reaction of the compound of the above formula (I-33) with alkylamine having a carboxy group or a sulfo group is carried out in known conditions per se. It is carried out in an aqueous or organic medium, at a temperature of, for example, 30 to 100° C., preferably 50 to 95° C. and at pH 5 to 13, preferably pH 6 to 11.

to as the brown dye) having a maximum absorption wavelength in the range of 350 nm to 550 nm, will be explained.

Aminobenzenes to obtain the condensation compound (BB) of 4,4'-dinitrostilbene-2,2'-disulfonic acid represented by the formula (II-6) or a salt thereof with an aminobenzenes and/or the reduced form thereof (CC) include, for example, an azo compound represented by the above formula (II-7).

As for $R^{41}$ to $R^{45}$ in the formula (II-7), examples of the C1 to C4 alkyl group include methyl, ethyl, n-propyl, isopropyl, n-butyl, isobutyl, sec-butyl, tert-butyl and the like. In addition, examples of the C1 to C4 alkoxy group include methoxy, ethoxy, n-propoxy, isopropoxy, n-butoxy, sec-butoxy, tert-butoxy and the like.

Preferably, each of $R^{41}$ to $R^{45}$ in the above formula (II-7) is, by way of example, independently hydrogen, hydroxy, sulfo, carboxy, methyl, ethyl, methoxy or ethoxy, and more preferably hydrogen, hydroxy, sulfo, carboxy, methyl or methoxy. $R^{41}$ to $R^{45}$ are each independent but can be the same or different from each other.

In the present invention, the condensation dye (BB) of the above formula (II-6) with formula (II-7) and the dye (CC) obtained by reduction thereof can be used in any form of free acid and salt. These salts can be freely converted to alkali metal salts, organic amine salts, ammonium salts or the like by a method such as salt forming or salt exchange, after the condensation of the formula (II-6) with the formula (II-7) or after the reduction thereafter. The alkali metal salt includes, for example, sodium, potassium, lithium salt or the like. The organic amine salt includes a salt with an amine such as methylamine, ethylamine, monoethanolamine, diethanolamine, triethanolamine, monoisopropanolamine, diisopropanolamine or triisopropanolamine, and a mixed salt thereof.

Examples of the aminobenzenes to be used in the present invention include a compound represented by the general formula (II-7), and suitable examples of the compound represented by the general formula (II-7) include, not limited in particular, compounds specifically shown in the following table II-7 and table II-8. In this connection, the sulfo groups and the carboxy groups are shown in free acid form, in the formulas in table II-7.

[Table II-7]

TABLE II-7

| Compound No. | Structural Formula |
|---|---|
| 4-1 | $H_2N$-C$_6$H$_4$-N=N-C$_6$H$_4$-COOH |
| 4-2 | $H_2N$-C$_6$H$_4$-N=N-C$_6$H$_4$(3-SO$_3$H) |
| 4-3 | $H_2N$-C$_6$H$_4$-N=N-C$_6$H$_4$-SO$_3$H |
| 4-4 | $H_2N$-C$_6$H$_3$(2-CH$_3$)-N=N-C$_6$H$_4$-SO$_3$H |
| 4-5 | $H_2N$-C$_6$H$_2$(2-CH$_3$,5-CH$_3$)-N=N-C$_6$H$_4$(3-SO$_3$H) |
| 4-6 | $H_2N$-C$_6$H$_2$(2-CH$_3$,5-CH$_3$)-N=N-C$_6$H$_4$-SO$_3$H |
| 4-7 | $H_2N$-C$_6$H$_2$(2-CH$_3$,5-CH$_3$)-N=N-C$_6$H$_3$(3-SO$_3$H,4-OCH$_3$) |

Table II-8

TABLE II-8

| Compound No. | Structural Formula |
|---|---|
| 4-8 | $H_2N$-C$_6$H$_2$(2-CH$_3$,5-CH$_3$)-N=N-C$_6$H$_2$(2-COOH,3-OCH$_3$,5-SO$_3$H) |
| 4-9 | $H_2N$-C$_6$H$_3$(2-OCH$_3$)-N=N-C$_6$H$_4$(3-SO$_3$H) |
| 4-10 | $H_2N$-C$_6$H$_2$(2-OCH$_3$,5-CH$_3$)-N=N-C$_6$H$_4$(3-SO$_3$H) |
| 4-11 | $H_2N$-C$_6$H$_2$(2-OCH$_3$,5-CH$_3$)-N=N-C$_6$H$_4$-SO$_3$H |
| 4-12 | $H_2N$-C$_6$H$_2$(2-OCH$_3$,5-CH$_3$)-N=N-C$_6$H$_2$(2-SO$_3$H,4-CH$_3$,5-OCH$_3$) |
| 4-13 | $H_2N$-C$_6$H$_2$(2-OCH$_3$,5-CH$_3$)-N=N-C$_6$H$_2$(2-COOH,3-OH,5-SO$_3$H) |

The condensation dye (BB) of 4,4'-dinitrostilbene-2,2'-disulfonic acid with the compound of the general formula (II-7) and the dye (CC) obtained by reduction thereof can be synthesized by, for example, the method described below.

The condensate (BB) of 4,4'-dinitrostilbene-2,2'-didisulfonic acid and the compound of general formula (II-7) can be obtained by reaction at typically 85 to 100° C. for typically 3 to 15 hours, 1 mol of 4,4'-dinitrostilbene-2,2'-disulfonic acid with the compound of the general formula (II-7) of an amount of typically 1 to 2.5 mol, preferably 1.3 to 1.8 mol, using typically caustic alkali, preferably a sodium hydroxide. The resulting condensate is known not to be a single substance and a compound represented by the following formula (II-34) is considered to be the principal ingredient.

The formula (II-34)

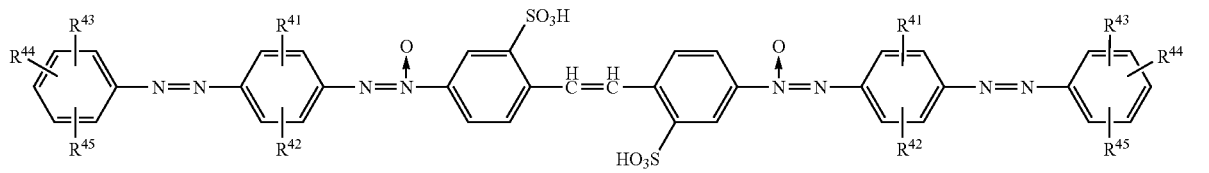

(II-34)

(wherein, $R^{41}$ to $R^{45}$ have the same meanings as in the above formula (II-7))

As a reducing agent to be used for reduction reaction of the condensate (BB), sodium sulfide or/and glucose are preferably used, typically in an amount of 0.1 to 0.4 mol based on 1 mol of 4,4'-dinitrostilbene-2,2'-disulfonic acid used in the synthesis of the condensate, at typically 80 to 95° C. for typically 0.5 to 2 hours for the reaction to obtain (CC). The compound (CC) obtained by reduction of (BB) is known not to be a single substance and a compound represented by the following formula (II-35) is considered to be the principal ingredient.

The formula (II-35)

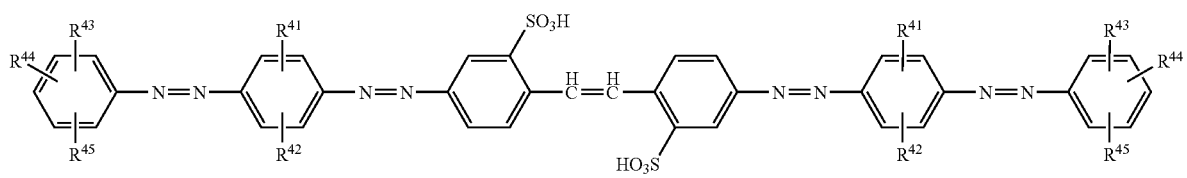

(II-35)

(wherein, $R^{41}$ to $R^{45}$ have the same meanings as in the formula (II-7))

In regard to the condensation dye (BB) of 4,4'-dinitrostilbene-2,2'-disulfonic acid and the general formula (II-7) to be used in the present invention or/and the dye (CC) obtained by reduction thereof, the reaction product obtained by the above reaction is used typically in the state of mixture as it is, while its principal ingredient may be purified for use. For the ink composition of the present invention, the above compound (BB) can be used, but typically the reductant (CC) of said condensation compound (BB) is more preferred.

Next, (c) the dye (blue-tinted dye) having a maximum absorption wavelength in the range of 560 nm to 660 nm will be explained.

At the beginning, the compound of the above formula (I-2) will be explained.

Firstly, the groups in $R^{20}$ to $R^{29}$ of the above formula (I-2) will be successively explained below.

Examples of the N-alkylaminosulfonyl group include, for example, a N—C1 to C4 alkylaminosulfonyl group such as N-methylaminosulfonyl, N-ethylaminosulfonyl, N-(n-propyl)aminosulfonyl, N-(n-butyl)aminosulfonyl, N,N-dimethylamiosulfonyl or N,N-di(n-propyl)aminosulfonyl.

Examples of the C1 to C4 alkylsulfonyl group which may be substituted by a hydroxy group include, for example, methylsulfonyl, ethylsulfonyl, propylsulfonyl, butylsulfonyl, hydroxyethylsulfonyl, 2-hydroxypropylsulfonyl, 3-hydroxypropylsulfonyl and the like.

Examples of the acyl group include, for example, acetyl, propionyl, butyryl, isobutyryl, benzoyl, naphthoyl or the like.

Examples of the C1 to C4 alkyl group which may be substituted by a hydroxy group or a C1 to C4 alkoxy group include, for example, methyl, ethyl, n-propyl, isopropyl, n-butyl, isobutyl, sec-butyl, tert-butyl, 2-hydroxyethyl, 2-hydroxypropyl, 3-hydroxypropyl, methoxyethyl, 2-ethoxyethyl, n-propoxyethyl, isopropoxyethyl, n-butoxyethyl, methoxypropyl, ethoxypropyl, n-propoxypropyl, isopropoxybutyl, n-propoxybutyl or the like.

Examples of the C1 to C4 alkoxy group which may be substituted by a hydroxy group, a C1 to C4 alkoxy group, a sulfo group or a carboxy group include, for example, methoxy, ethoxy, n-propoxy, isopropoxy, n-butoxy, sec-butoxy, tert-butoxy, 2-hydroxyethoxy, 2-hydroxypropoxy, 3-hydroxypropoxy, methoxyethoxy, ethoxyethoxy, n-propoxyethoxy, isopropoxyethoxy, n-butoxyethoxy, methoxypropoxy, ethoxypropoxy, n-propoxypropoxy, isopropoxybutoxy, n-propoxybutoxy, 2-hydroxyethoxyethoxy, carboxymethoxy, 2-carboxyethoxy, 3-carboxypropoxy, 3-sulfopropoxy, 4-sulfobutoxy or the like.

Examples of the acylamino group include, for example, acetylamino, propionylamino, butyrylamino, isobutyrylamino, benzoylamino, naphthoylamino or the like.

Examples of the alkylsulfonylamino group include, for example, methylsulfonylamino, ethylsulfonylamino, propylsulfonyl amino or the like.

Examples of the phenylsulfonylamino group which may be substituted by a halogen atom, an alkyl group or a nitro group include, for example, benzenesulfonylamino, toluenesulfonylamino, chlorobenzenesulfonylamino, nitrobenzenesulfonylamino or the like. The halogen atom, the alkyl group or the nitro group as a substituent on the phenyl group may be substituted at any of the orto-, meta- and para-positions on the phenyl ring.

The above explanation is about the groups in $R^{20}$ to $R^{29}$ of the formula (I-2) and can be applied for the same groups in the other formulas.

Preferably, each of $R^{21}$ and $R^{22}$ in the above formula (I-2) is independently a hydrogen atom, a chlorine atom, a bromine atom, cyano, carboxy, sulfo, sulfamoyl, N-methylaminosulfonyl, N-phenylaminosulfonyl, methylsulfonyl, hydroxyethylsulfonyl, phosphono, nitro, acetyl, benzoyl, ureide, methyl, methoxy, ethyl, ethoxy, propyl, propoxy, 2-hydroxyethoxy, 2-methoxyethoxy, 2-ethoxyethoxy, 3-sulfopropoxy, 4-sulfobutoxy, carboxymethoxy, 2-carboxyethoxy, acetylamino, benzoylamino or the like, more preferably a hydrogen atom, a chlorine atom, cyano, sulfamoyl, acetyl, methylsulfonyl, hydroxyethylsulfonyl, nitro, carboxy or sulfo, and further preferably a hydrogen atom, a carboxy group or sulfo. Further preferably, $R^{21}$ is a carboxy or sulfo group, and particularly preferably sulfo. $R^{22}$ is particularly preferably a hydrogen atom. As for the substitution positions of the nitro group on the leftmost phenyl group and the other substituents in the above formula (I-2), it is preferred that the substitution position of the nitro is the para-position to the azo group when the substitution position of $R^{21}$ is the ortho-position to the azo group, and that the substitution position of the nitro is the ortho-position to the azo group when the substitution position of $R^{21}$ is the para-position to the azo group.

$R^{23}$ to $R^{26}$ in the above formula (I-2) is preferably a hydrogen atom, a chlorine atom, hydroxy, cyano, carboxy, sulfo, sulfamoyl, N-methylaminosulfonyl, N-phenylaminosulfonyl, methylsulfonyl, hydroxyethylsulfonyl, nitro, acetyl, benzoyl, ureide, methyl, methoxy, ethyl, ethoxy, propyl, propoxy, 2-hydroxyethoxy, 2-methoxyethoxy, 2-ethoxyethoxy, 3-sulfopropoxy, 4-sulfobutoxy, carboxymethoxy, 2-carboxyethoxy, acetylamino, benzoylamino or the like, more preferably a hydrogen atom, methyl, ethyl, methoxy, ethoxy, 2-hydroxyethoxy, 3-sulfopropoxy, carboxy or sulfo, and further preferably a hydrogen atom, methyl, 2-hydroxyethoxy, 3-sulfopropoxy, carboxy or sulfo.

Preferably, each of $R^{20}$ and $R^{27}$ to $R^{29}$ in the above formula (I-2) is independently a hydrogen atom, a chlorine atom, a bromine atom, hydroxy, cyano, carboxy, sulfo, sulfamoyl, N-methylaminosulfonyl, N-phenylaminosulfonyl, methylsulfonyl, hydroxyethylsulfonyl, phospho, nitro, acetyl, benzoyl, ureide, methyl, methoxy, ethyl, ethoxy, propyl, propoxy, 2-hydroxyethoxy, 2-methoxyethoxy, 2-ethoxyethoxy, 3-sulfopropoxy, 4-sulfobutoxy, carboxymethoxy, 2-carboxyethoxy, acetylamino, benzoylamino or the like, more preferably a hydrogen atom, hydroxy, carboxy, sulfo, sulfamoyl, hydroxyethylsulfonyl, nitro, methyl, methoxy, ethyl or ethoxy, and further preferably a hydrogen atom, hydroxy, carboxy, sulfo or sulfamoyl.

A preferable combination of $R^{20}$ and $R^{27}$ to $R^{29}$ is that $R^{27}$ is a hydrogen atom, $R^{28}$ and $R^{29}$ are sulfo, and $R^{20}$ is hydroxy, the substitution position of $R^{20}$ is preferably the peri-position to the azo group.

A compound of preferable combination of the substituents in the above formula (I-2) is a compound where $R^{21}$ is sulfo, carboxy or cyano, the substitution position of the nitro is the para-position to the azo group when the substitution position of $R^{21}$ is the ortho-position to the azo group, or $R^{21}$ is sulfo or cyano, the substitution position of the nitro is the ortho-position to the azo group when the substitution position of $R^{21}$ is the para-position to the azo group, $R^{22}$ is a hydrogen atom, $R^{23}$ and $R^{25}$ are sulfo or hydroxy-substituted C1 to C4 alkoxy, $R^{24}$ and $R^{26}$ are hydrogen atoms, C1 to C4 alkyl or hydroxy-substituted C1 to C4 alkoxy, $R^{27}$ is a hydrogen atom, $R^{28}$ and $R^{29}$ are sulfo, $R^{20}$ is hydroxy or sulfo, the substitution position of $R^{20}$ being the peri-position to the azo group, and n is 1.

In addition, a compound of the formula (I-2) where in the above formula (I-2), $R^{21}$ is a sulfo group or a carboxy group, the substitution position of the nitro group is the para-position to the azo group when the substitution position of $R^{21}$ is the ortho-position to the azo group, and the substitution position of the nitro group is the ortho-position to the azo group when the substitution position of $R^{22}$ is the para-position to the azo group is also preferable and more preferable than the case where $R^{22}$ is a hydrogen atom.

More preferable is a compound where $R^{21}$ is sulfo and its substitution position is the ortho-position to the azo group, the substitution position of the nitro is the para-position to the azo group, $R^{22}$ is a hydrogen atom, $R^{23}$ and $R^{25}$ is sulfo-substituted C1 to C4 alkoxy, $R^{24}$ and $R^{26}$ are C1 to C4 alkyl, $R^{27}$ is a hydrogen atom, $R^{28}$ and $R^{29}$ are sulfo, $R^{20}$ is hydroxy and its substitution position is the peri-position to the azo group, and n is 1. Particularly preferable is a compound where $R^{21}$ is sulfo and its substitution position is the ortho-position to the azo group, the substitution position of the nitro is the para-position to the azo group, $R^{22}$ is a hydrogen atom, $R^{23}$ and $R^{25}$ are 3-sulfopropoxy, $R^{24}$ and $R^{26}$ are methyl, $R^{27}$ is a hydrogen atom, $R^{28}$ and $R^{29}$ are sulfo, $R^{20}$ is hydroxy and its substitution position is the peri-position to the azo group, and n is 1, respectively.

The azo compound represented by the above formula (I-2) in free acid form can form various salts, and it can be in any form of free acid and various salts. The salt of the formula (I-2) is an inorganic or organic cation salt. Of them, specific examples of the inorganic salt include an alkali metal salt, an alkali earth metal salt and an ammonium salt, preferable inorganic salts being a salt of lithium, sodium, or potassium and an ammonium salt, and the organic cation includes, for example, quaternary ammoniums represented by the above formula (I-11), preferable example being the same as the above but not limited thereto.

The azo compound represented by the above formula (I-2) can be synthesized by, for example, the following method. In this connection, the structural formula of the compound in each process is shown in free acid form. In addition, n and $R^{20}$ to $R^{29}$ described in the following formula (I-18) to formula (I-28) have the same meanings as in the above formula (I-2), respectively. A compound of the following formula (I-18) is reacted with a p-toluenesulfonyl chloride in the presence of alkali to obtain a compound represented by the following formula (I-19).

The formula (I-18)

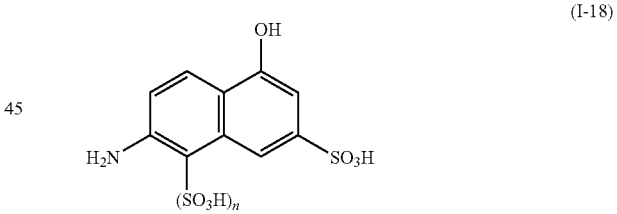

The formula (I-19)

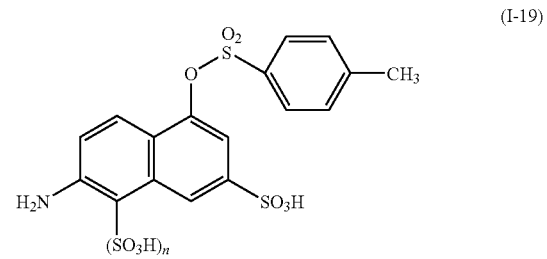

The obtained compound represented by the above formula (I-19) is diazotized in a conventional manner, and then subjected to coupling reaction with 4-amino-5-naphthole-1,7- disulfonic acid under acidic conditions to obtain a compound represented by the following formula (I-20).
The formula (I-20)

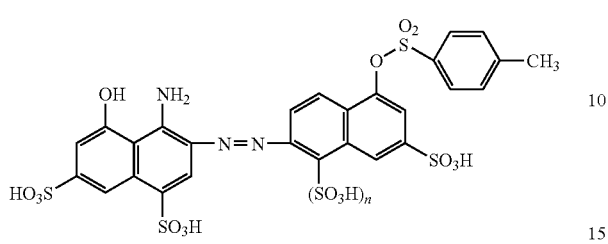

Subsequently, a compound represented by the following formula (I-21) is diazotized in a conventional manner, and then subjected to coupling reaction with the compound represented by the above formula (I-20) to obtain a compound represented by the following formula (I-22).
The formula (I-21)

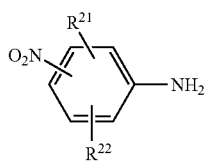

The formula (I-22)

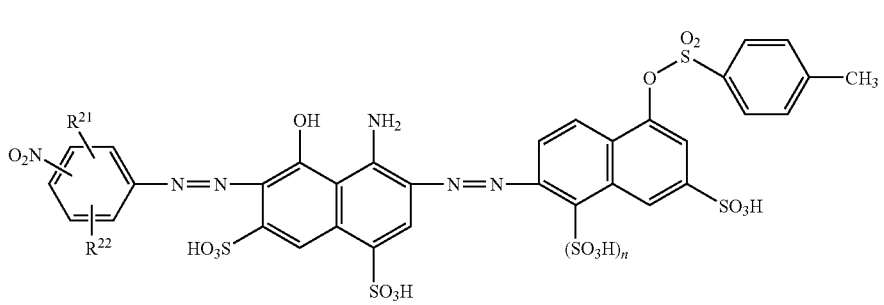

The obtained compound represented by the above formula (I-22) hydrolyzed under alkaline conditions to obtain a compound represented by the following formula (I-23).
The formula (I-23)

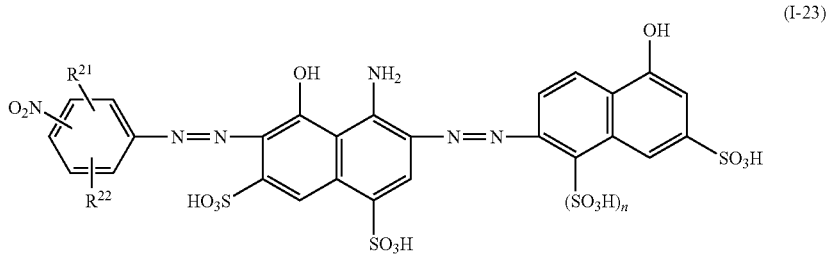

On the other hand, a compound represented by the following formula (I-24) is diazotized in a conventional manner, and then subjected to coupling reaction with a compound represented by the following formula (I-25) to obtain a compound of the following formula (I-26).
The formula (I-24)

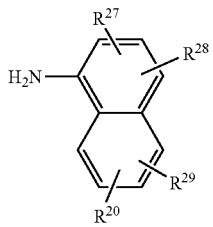

The formula (I-25)

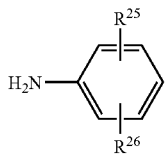

The formula (I-26)

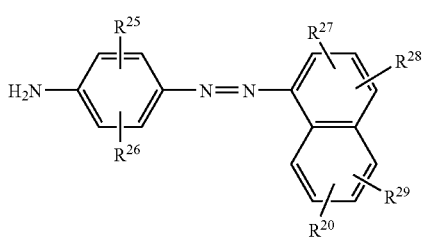

The obtained compound represented by the above formula (I-26) is diazotized in a conventional manner, and then subjected to coupling reaction with a compound represented by the following formula (I-27) to obtain a compound represented by the following formula (I-28).

The formula (I-27)

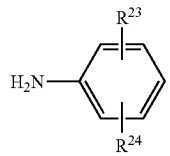

(I-27)

The formula (I-28)

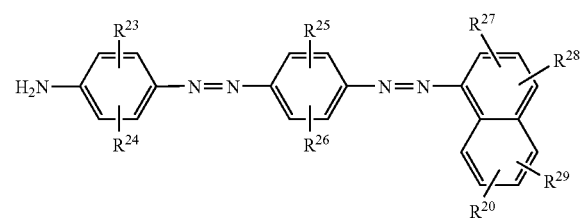

(I-28)

The obtained compound represented by the above formula (I-28) is diazotized in a conventional manner, and then subjected to coupling reaction with a compound represented by the above formula (I-23) to obtain an azo compound represented by the above formula (I-2) or a salt thereof which can be contained in the ink composition of the present invention.

The esterification reaction of the compound of the formula (I-18) and a p-toluenesulphonyl chloride is carried out by a known method per se, and it is advisable to carry it out in water or an aqueous organic medium at a temperature of, for example, 20 to 100° C., preferably 30 to 80° C. and at a neutral to alkaline pH value. It is more preferably carried out at neutral to weakly alkaline, for example, pH 7 to 10. Adjustment of this pH value is carried out by addition of a base. As the base, for example, an alkali metal hydroxide such as lithium hydroxide or sodium hydroxide, an alkali metal carbonate such as lithium carbonate, sodium carbonate or potassium carbonate, an acetate salt such as sodium acetate, or the like. The compound of the formula (I-18) and the p-toluenesulphonyl chloride are used in approximately stoichiometric amounts.

The diazotization of the compound of the formula (I-19) is carried out by a known method per se, for example, in an inorganic acid medium, at a temperature of, for example, −5 to 30° C., preferably 5 to 15° C., using a nitrite salt, for example, an alkali metal nitrite such as sodium nitrite. The coupling of the diazotized compound of the formula (I-19) with 4-amino-5-naphthole-1,7-disulfonic acid is also carried out under known conditions per se. That is, it is advisable to carry it out in water or an aqueous organic medium at a temperature of, for example, −5 to 30° C., preferably 5 to 25° C. and at an acidic to neutral pH value. The pH inside this reaction system is acidified, however it is carried out preferably at acidic to weakly acidic, for example, pH 1 to 4. Adjustment of this pH value is carried out by addition of a base. As the base, the same as above can be used. The compound of the formula (I-19) and 4-amino-5-naphthole-1,7-didisulfonic acid are used in approximately stoichiometric amounts.

The diazotization of the compound of the formula (I-21) is also carried out by a known method per se, for example, in an inorganic acid medium at a temperature of, for example, −5 to 30° C., preferably 0 to 15° C., using a nitrite salt, for example, an alkali metal nitrite such as sodium nitrite. The coupling of the diazotized compound of the formula (I-21) with the compound of the formula (I-20) is also carried out under known conditions per se. It is advisable to carry it out in water or an aqueous organic medium at a temperature of, for example, −5 to 30° C., preferably 10 to 25° C. and at a weakly acidic to alkaline pH value. It is carried out preferably at weakly acidic to weakly alkaline, for example, pH 5 to 10, and adjustment of the pH value is carried out by addition of a base. As the base, the same as above can be used. The compounds of the formulas (I-20) and (I-21) are used in approximately stoichiometric amounts.

The production of the compound of the formula (I-23) by hydrolyzation of the compound of the formula (I-22) is also carried out by a known method per se. For the hydrolyzation, a method by heating in an aqueous alkaline medium is suitably used, and it is carried out, for example, by adding a sodium hydroxide or a potassium hydroxide in a solution containing the compound of the formula (I-22) to adjust the pH to 9.5 or more, and then heating to a temperature of, for example, 20 to 150° C., preferably 30 to 100° C. At this time, the pH value of the reaction solution is preferably maintained at 9.5 to 11.5. Adjustment of this pH value is carried out by addition of a base. As the base, the above can be used.

The diazotization of the compound of the formula (I-24) is also carried out by a known method per se, for example, in an inorganic acid medium at a temperature of, for example, −5 to 30° C., preferably 0 to 15° C., using a nitrite salt, for example, an alkali metal nitrite such as sodium nitrite. The coupling of the diazotized compound of the formula (I-24) and the compound of the formula (I-25) is also carried out under known conditions per se. It is advisable to carry it out in water or an aqueous organic medium at a temperature of, for example, −5 to 30° C., preferably 5 to 25° C. and at an acidic to neutral pH value. It is carried out, for example, at pH 1 to 7, and adjustment of the pH value is carried out by addition of a base. As the base, the same as above can be used. The compounds of the formulas (I-24) and (I-25) are used in approximately stoichiometric amounts.

The diazotization of the compound of the formula (I-26) is also carried out by a known method per se, for example, in an inorganic acid medium at a temperature of, for example, −5 to 30° C., preferably 5 to 25° C., using a nitrite salt, for example, an alkali metal nitrite such as sodium nitrite. The coupling of the diazotized compound of the formula (I-26) with the compound of the formula (I-27) is carried out under known conditions per se. It is advisable to carry it out in water or an aqueous organic medium at a temperature of, for example, −5 to 30° C., preferably 10 to 30° C. and at a weakly acidic to alkaline pH value. It is carried out preferably at weakly acidic to weakly alkaline, for example, pH 6 to 10, and adjustment of the pH value is carried out by addition of a base. As the base, the same as above can be used. The compounds of the formulas (I-27) and (I-26) are used in approximately stoichiometric amounts.

The diazotization of the compound of the formula (I-28) is also carried out by a known method per se, for example, in an inorganic acid medium at a temperature of, for example, −5 to 30° C., preferably 5 to 25° C., using a nitrite salt, for example, an alkali metal nitrite such as sodium nitrite. The coupling of the diazotized compound of the formula (I-28) with the compound of the formula (I-23) is also carried out under known conditions per se. It is advisable to carry it out in water or an aqueous organic medium at a temperature of, for example, −5 to 30° C., preferably 10 to 30° C. and at a weakly acidic to alkaline pH value. It is carried out preferably at weakly acidic to weakly alkaline, for example, pH 6 to 10, and adjustment of the pH value is carried out by addition of a base. As the base, the same as above can be used. The compounds of the formula (I-23) and (I-28) are used in approximately stoichiometric amounts.

Suitable specific examples of the compound represented by the formula (I-2) include, not limited in particular, the compounds represented by the formulas described in the following tables I-5 and I-6. The acidic functional groups such as the sulfo groups and the carboxy groups in the tables are shown in free acid form.

Table I-5

TABLE I-5

| Compound No. | Structural Formula |
|---|---|
| 2-1 | |
| 2-2 | |
| 2-3 | |
| 2-4 | |

TABLE 1-5-continued
| Compound No. | Structural Formula |
|---|---|
| 2-5 | 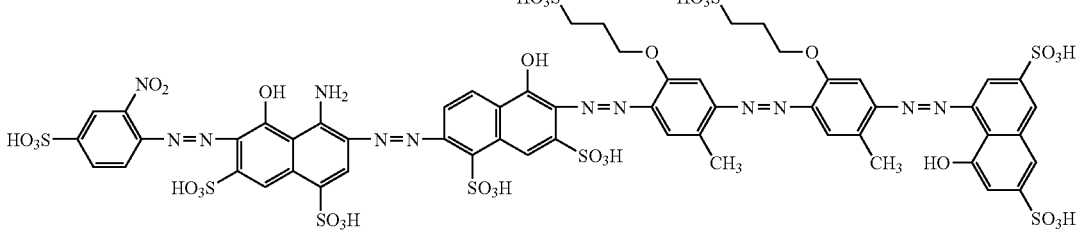 |
| 2-6 | 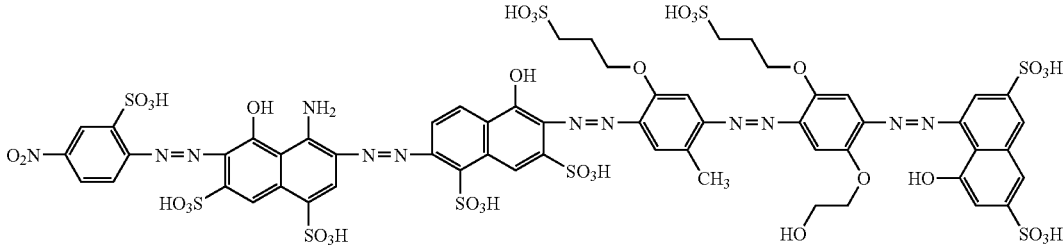 |
TABLE I-6
| Compound No. | Structural Formula |
|---|---|
| 2-7 | 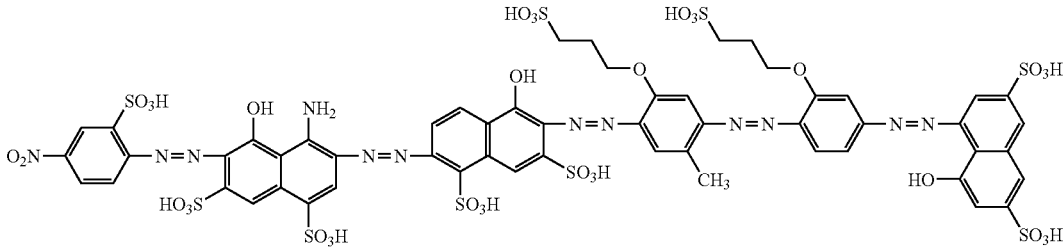 |
| 2-8 | 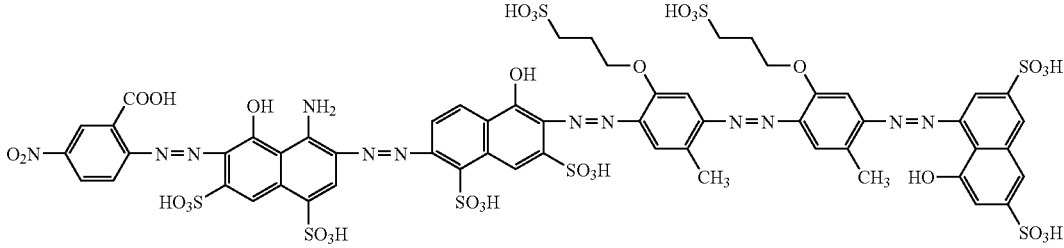 |

TABLE I-6-continued

| Compound No. | Structural Formula |
|---|---|
| 2-9 | |
| 2-10 | |
| 2-11 | |
| 2-12 | |

Next, the compound of the above formula (II-2) of the dye (c) (blue-tinted black dye) having a maximum absorption wavelength in the range of 560 nm to 660 nm will be explained.

The azo compound represented by the above formula (II-2) can be synthesized by, for example, the following method. In this connection, the structural formula of the compound in each process is represented in free acid form. In addition, all the symbols in the formulas such as m, n, $R^{121}$ to $R^{128}$, X, B', C' and the like have the same meanings as in the above formula (II-2) to formula (II-4).

An aminonaphtholsulfonic acid represented by the following formula (II-18)

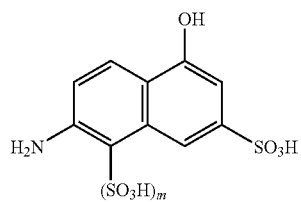
(II-18)

and a p-toluenesulfonyl chloride are subjected to esterification reaction in the presence of alkali. The obtained compound represented by the following formula (II-19)

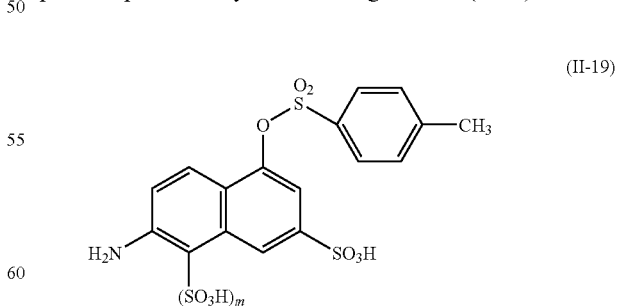
(II-19)

is diazotized in a conventional manner, and the obtained diazotized compound is subjected to coupling reaction in the presence of 4-amino-5-naphthole-1,7-disulfonic acid. With the resulting compound represented by the following formula (II-20), (II-20)

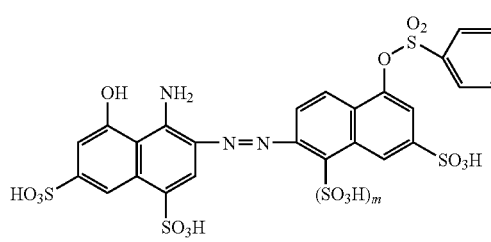

the diazotized compound of the compound represented by the following formula (II-21)

(II-21)

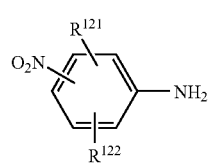

is subjected to coupling reaction. The obtained compound represented by the following formula (II-22)

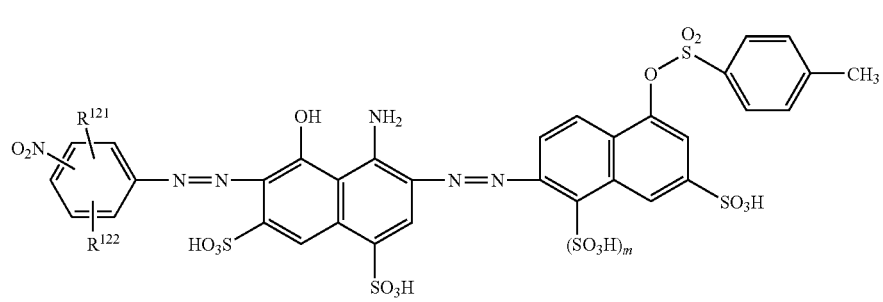

is hydrolyzed under alkaline conditions to obtain a compound represented by the formula (II-23).

(II-23)

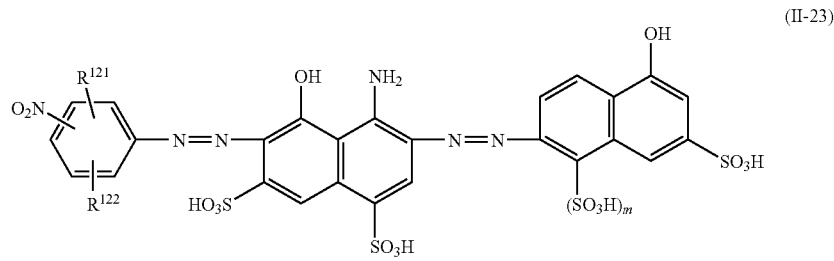

Subsequently, by esterification reaction of a compound represented by the formula (II-24)

(II-24)

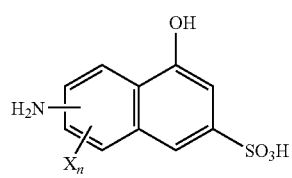

with p-toluenesulfonyl chloride in the presence of alkali, a compound represented by the following formula (II-25)

(II-25)

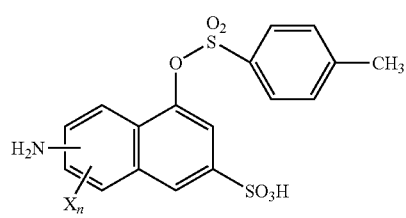

is obtained. Said compound is diazotized in a conventional manner, and then coupled with the compound of the above formula (II-23) to obtain a compound of the following formula (II-26).

(II-26)

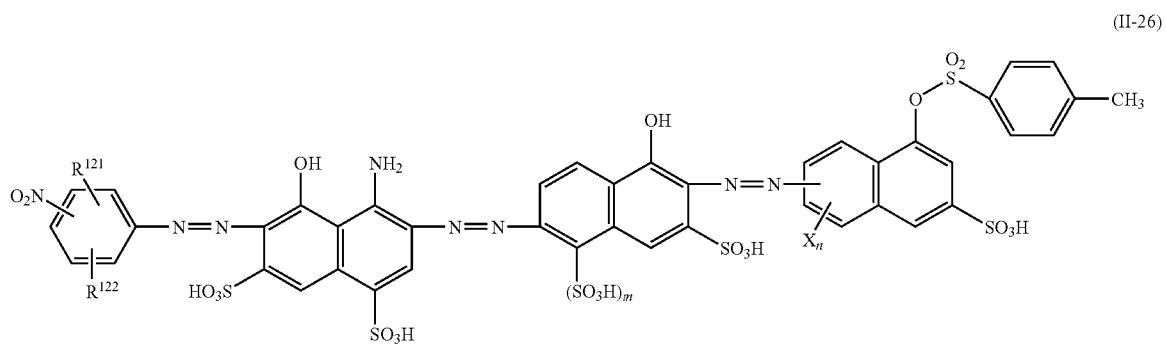

The obtained compound of the formula (II-26) is hydrolyzed under alkali conditions to obtain a compound represented by the following formula (II-27)

(II-27)

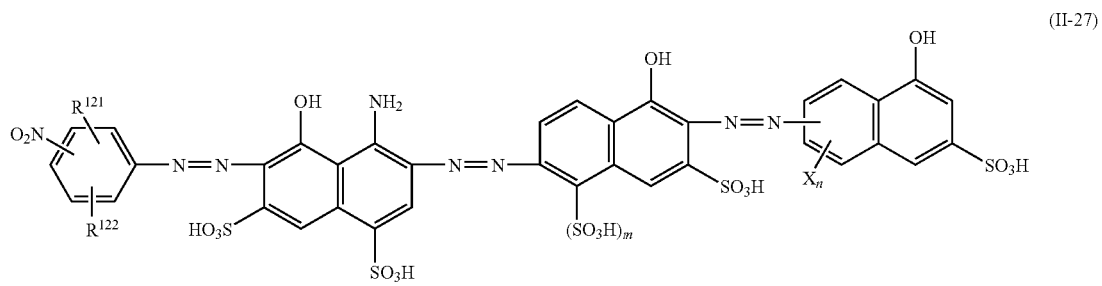

Subsequently, a compound represented by the following formula (II-28)

H₂N—C'     (II-28)

is diazotized in a conventional manner. With the obtained diazotized compound, a compound represented by the following formula (II-29)

H₂N—B'     (II-29)

is subjected to coupling reaction to obtain a compound represented by the following formula (II-30).

H₂N—B'—N=N—C'     (II-30)

The monoazo compound represented by the above formula (II-30) is diazotized in a conventional manner, and then the compound of the above formula (II-27) is subjected to coupling reaction with the obtained diazotized compound to obtain the azo compound represented by the above formula (II-2) or a salt thereof.

Suitable specific examples of the compound of the formula (II-2) can include, not limited in particular, the compounds described in the following tables II-3 to II-5. The sulfo groups and the carboxy groups in the tables are shown in free acid form.

[Table II-3]

TABLE II-3

| Compound No. | Structural Formula |
|---|---|
| 2-1 | (structure shown) |

TABLE II-3-continued
| Compound No. | Structural Formula |
|---|---|
| 2-2 | 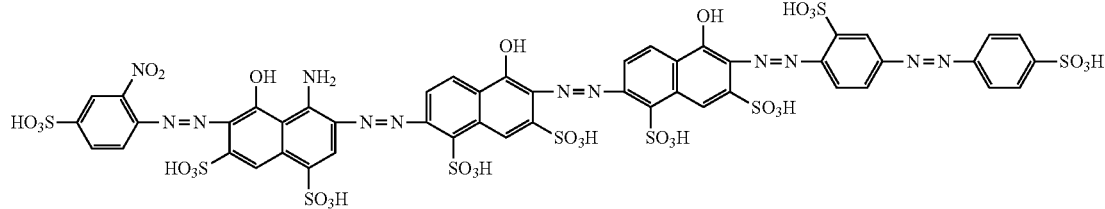 |
| 2-3 | 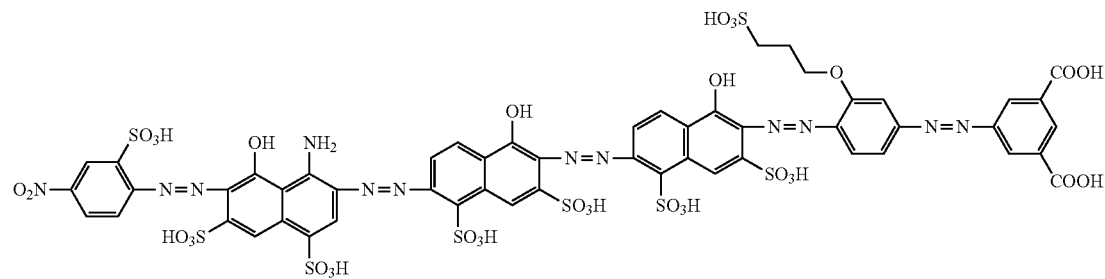 |
| 2-4 | 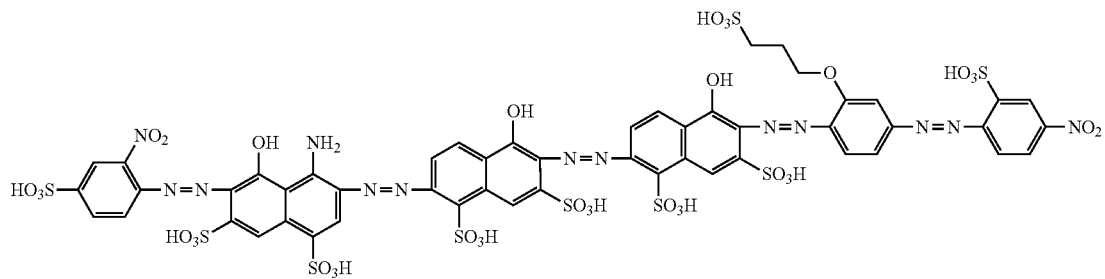 |
| 2-5 | 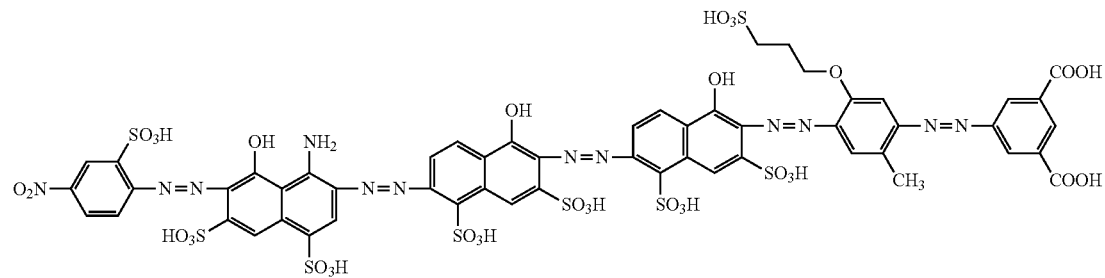 |
| 2-6 | 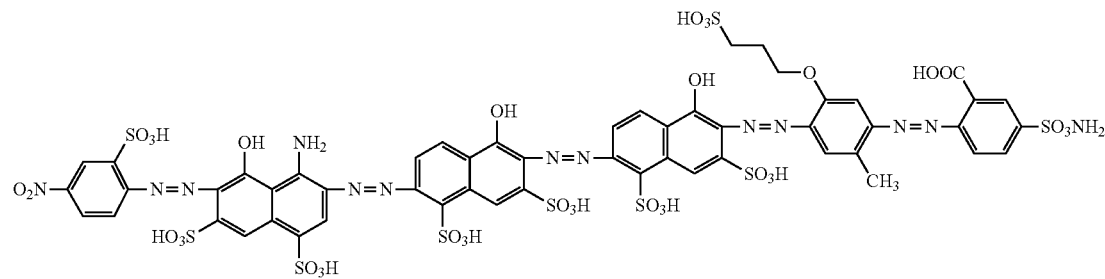 |

[Table II-4]

TABLE II-4

| Compound No. | Structural Formula |
|---|---|
| 2-7 | |
| 2-8 | |
| 2-9 | |
| 2-10 | |
| 2-11 | |
| 2-12 | |

[Table II-5]

TABLE II-5

| Compound No. | Structural Formula |
|---|---|
| 2-13 | |
| 2-14 | |
| 2-15 | |
| 2-16 | |
| 2-17 | |
| 2-18 | |

The esterification reaction of the compound of the above formula (II-18) and a p-toluenesulphonyl chloride can be carried out by a known method per se.

Said esterification reaction is advantageously carried out, for example, in water or an aqueous organic medium, at a temperature of 20 to 100° C., preferably 30 to 80° C. and a neutral to alkaline pH value, for example, pH 7 to 10. Adjustment of this pH value is carried out by addition of a base. As the base, for example, an alkali metal hydroxide such as lithium hydroxide or sodium hydroxide, an alkali metal carbonate such as lithium carbonate, sodium carbonate or potassium carbonate, an acetate salt such as sodium acetate, or the like can be used. The compound of the formula (II-18) and the p-toluenesulphonyl chloride are used in approximately stoichiometric amounts.

The diazotization of the compound of the above formula (II-19) can be carried out by a known method per se, for example, in an inorganic acid medium at a temperature of, for example −5 to 30° C., preferably 5 to 15° C., using a nitrite salt, for example, an alkali metal nitrite such as sodium nitrite. The coupling of the diazotized compound of the compound of the formula (II-19) with 4-amino-5-naphthole-1,7-disulfonic acid can also be carried out by known conditions per se. Said coupling reaction is advantageously carried out in water or an aqueous organic medium at a temperature of, for example, −5 to 30° C., preferably 5 to 25° C. and at an acidic to neutral pH value. Preferably, said pH is preferably adjusted to an acidic to weakly acidic pH value, for example, pH 1 to 4 because pH of the coupling bath becomes acidic. Adjustment of this pH value is carried out by addition of a base. As the base, for example, an alkali metal hydroxide such as lithium hydroxide or sodium hydroxide, an alkali metal carbonate such as lithium carbonate, sodium carbonate or potassium carbonate, an acetate salt such as sodium acetate, ammonia, organic amine or the like can be used. The compound of the formula (II-19) and 4-amino-5-naphthole-1,7-disulfonic acid are used in approximately stoichiometric amounts.

The diazotization of the compound of the formula (II-21) is also carried out by a known method per se. It is carried out, for example, in an inorganic acid medium at a temperature of, for example, −5 to 30° C., preferably 0 to 15° C., using a nitrite salt, for example, an alkali metal nitrite such as sodium nitrite. The coupling of the diazotized compound of the compound of the formula (II-21) with the compound of the formula (II-20) is also carried out by known conditions per se. It is advantageously carried out in water or an aqueous organic medium at a temperature of, for example, −5 to 30° C., preferably 10 to 25° C. and a pH of weakly acidic to alkaline, for example pH 5 to 10. Adjustment of the pH value is carried out by addition of a base. As the base, the above can be used. The compounds of the formulas (II-20) and (II-21) are used in approximately stoichiometric amounts.

The production of the compound of the formula (II-23) by hydrolyzation of the compound of the formula (II-22) is also carried out by a known method per se. A method by heating in an aqueous alkaline medium is advantageous and is carried out, for example, by adding a sodium hydroxide or a potassium hydroxide in a solution containing the compound of the formula (II-22) to adjust the pH to 9.5 or more, and then heating to a temperature of, for example, 20 to 150° C., preferably a temperature of 30 to 100° C. At this time, the pH value of the reaction solution is preferably maintained at 9.5 to 11.5. Adjustment of this pH value is carried out by addition of a base. As the base, the above can be used.

The esterification reaction of the compound of the formula (II-24) with p-toluenesulphonyl chloride is carried out by a known method per se. It is advantageously carried out in water or an aqueous organic medium at a temperature of, for example, 20 to 100° C., preferably 30 to 80° C. and at a neutral to alkaline pH value, for example, pH 7 to 10. Adjustment of this pH value is carried out by addition of a base. As the base, the above can be used. The compound of the formula (II-24) and p-toluenesulphonyl chloride are used in approximately stoichiometric amounts.

The diazotization of the compound of the formula (II-25) is also carried out by a known method per se. It is carried out, for example, in an inorganic acid medium at a temperature of, for example, −5 to 30° C., preferably 0 to 15° C., using a nitrite salt, for example, an alkali metal nitrite such as sodium nitrite. The coupling of the diazotized compound of the compound of the formula (II-25) with the compound of the formula (II-23) is also carried out under known conditions per se. It is advantageously carried out in water or an aqueous organic medium at a temperature of, for example, −5 to 30° C., preferably 10 to 25° C. and at a weakly acidic to alkaline pH value, for example, pH 5 to 10. Adjustment of the pH value is carried out by addition of a base. As the base, the above can be used. The compounds of the formulas (II-23) and (II-25) are used in stoichiometric amounts.

The production of the compound of the formula (II-27) by hydrolyzation of the compound of the formula (II-26) is also carried out by a known method per se. A method by heating in an aqueous alkaline medium is advantageous and carried out, for example, by addition of a sodium hydroxide or a potassium hydroxide in a solution containing the compound of the formula (II-26) to adjust the pH to 9.5 or more, and then heating to a temperature of, for example, 20 to 150° C., preferably a temperature of 30 to 100° C. At this time, the pH value of the reaction solution is preferably maintained at 9.5 to 11.5. Adjustment of this pH value is carried out by addition of a base. As the base, the above can be used.

The diazotization of the compound of the formula (II-28) is also carried out by a known method per se, for example, in an inorganic acid medium at a temperature of, for example, −5 to 30° C., preferably 0 to 15° C., using a nitrite salt, for example, an alkali metal nitrite such as sodium nitrite. The coupling of the diazotized compound of the compound of the formula (II-28) with the compound of the formula (II-29) is also carried out under known conditions per se. It is advantageously carried out in water or an aqueous organic medium at a temperature of, for example, −5 to 30° C., preferably 5 to 25° C. and an acidic to neutral pH value. It is carried out, for example, at pH 1 to 7, and adjustment of the pH value is carried out by addition of a base. As the base, the above can be used. The compounds of the formulas (II-28) and (II-29) are used in approximately stoichiometric amounts.

The diazotization of the compound of the formula (II-30) can be also carried out by a known method per se in the same manner as above. The coupling of the diazotized compound of the compound of the formula (II-30) with the compound of the formula (II-27) is also carried out under known conditions per se. It is advantageously carried out in water or an aqueous organic medium at a temperature of, for example, −5 to 30° C., preferably 10 to 30° C. and at a weakly acidic to alkaline pH value. It is carried out preferably at a weakly acidic to weakly alkaline pH value, for example, pH 6 to 10. Adjustment of the pH value is carried out by addition of a base. As the base, the above can be used. The compounds of the formulas (II-30) and (II-27) are used in approximately stoichiometric amounts.

One of the suitable combinations of dyes to obtain achromatic black having a high print density is the combination of the compound represented by the formula (1), the compound represented by the formula (I-2) and the compound of the formula (5). The water-based black dye composition containing these compounds exhibits achromatic excellent black and is suitable in particular as a water-based black ink composition suitable for inkjet recording.

As for the use ratios of the compound of the formula (1), the compound of the formula (I-2) and the compound of the formula (5), based on the total amount of the three, the compound of the formula (1) is 5 to 60% by mass, the compound of the formula (I-2) is 10 to 80% by mass and the compound of the formula (5) is 5 to 60% by mass (hereinafter, % represents % by mass unless otherwise noted in particular), preferably the compound of the formula (1) is 10 to 50%, the compound of the formula (I-2) is 20 to 70% and the compound of the formula (5) is 10 to 50%, and more preferably the compound of the formula (1) is 15 to 45%, the compound of the formula (I-2) is 25 to 65% and the compound of the formula (5) is 15 to 45%. The mixture ratio of the three is so adjusted that each of the three dyes is within the range of the each content described above and the total of the three equals 100%.

As another of the suitable combinations of dyes to obtain achromatic black having a high print density, as a dye having a maximum absorption wavelength in the range of 350 nm to 550 nm, the dye represented by the general formula (5) and/or the condensation dye (BB) of 4,4'-dinitrostilbene-2,2'-disulfonic acid of the formula (II-6) and a compound represented by the formula (II-7) and/or the dye (CC) obtained by reduction thereof are preferably formulated with the compounds represented by the general formula (1) and the general formula (II-2) for use.

As for the use ratios of the compound of the general formula (1) and the compound of the general formula (II-2), based on the total amount of the both, the compound of the formula (1) is 10 to 90% and the compound of the formula (II-2) is 90 to 10%, preferably the compound of the formula (1) is 20 to 80% and the compound of the formula (II-2) is 80 to 20%, and more preferably the compound of the formula (1) is 30 to 70% and the compound of the formula (II-2) is 70 to 30%.

When this ink composition is used as an ink for ink jet printers, the azo compound of the present invention to be used preferably has a small content of inorganic substances such as metal cation chloride and sulfuric acid salt. Its content is, for example, approximately 1% by mass or less (to the bulk of the coloring matter) only as a guide. The azo compound of the present invention having a small content of inorganic substances can be produced by a desalting treatment, for example, a typical method using a reverse osmosis membrane; or a method where a dried form or a wet cake of the azo compound of the present invention is stirred in a mixed solvent of alcohol and water such as methanol, and the precipitate is separated by filtration and then dried; and the like.

Specific examples of the water-soluble organic solvent to be used in preparation of the above ink composition include, for example, a C1 to C4 alkanol such as methanol, ethanol, propanol, isopropanol, butanol, isobutanol, secondary butanol or tertiary butanol; a carboxylic acid amide such as N,N-dimethylformamide or N,N-dimethylacetoamide; a lactam such as 2-pyrolidone or N-methyl-2-pyrrolidone(N-methylpyrrolidin-2-one); a cyclic urea such as 1,3-dimethylimidazolidin-2-one or 1,3-dimethylhexahydropyrimid-2-one; a ketone or keto alcohol such as acetone, methylethylketone or 2-methyl-2-hydroxypentan-4-one; a cyclic ether such as tetrahydrofuran or dioxane; a mono-, oligo- or poly-alkylene glycol having a C2 to C6 alkylene unit or a thioglycol such as ethyleneglycol, 1,2-propyleneglycol, 1,3-propyleneglycol, 1,2-butyleneglycol, 1,4-butyleneglycol, 1,6-hexyleneglycol, diethylene glycol, triethylene glycol, tetraethylene glycol, dipropylene glycol, polyethylene glycol, polypropylene glycol, thiodiglycol or dithiodiglycol; polyol(triol) such as glycerine or hexane-1,2,6-triol; a C1 to C4 alkyl ether of polyhydric alcohol such as ethylene glycol monomethyl ether or ethylene glycol monoethyl ether, diethylene glycol monomethyl ether or diethylene glycol monoethyl ether, or triethylene glycol monomethyl ether or triethylene glycol monoethyl ether; γ-butyrolactone; dimethylsulfoxide; or the like. These water-soluble organic solvents are used alone or as a mixture thereof. Preferable among them are 2-pyrolidone, N-methyl-2-pyrolidone, mono, di- or tri ethyleneglycol and dipropylene glycol, and more preferably 2-pyrolidone, N-methyl-2-pyrolidone, diethylene glycol, isopropyl alcohol and butylcarbitol.

The ink preparation agents to be used in preparation of the above ink composition include, for example, an antiseptic and fungicide, a pH adjuster, a chelating agent, a rust-preventive agent, a water-soluble UV absorbing agent, a water-soluble polymer compound, a dye dissolving agent, an antioxidant, a surfactant and/or the like. These agents will be explained below.

Specific examples of the fungicide include sodium dehydroacetate, sodium benzoate, sodium pyridinethion-1-oxide, p-hydroxybenzoate ethyl ester, 1,2-benzisothiazolin-3-one and a salt thereof, and the like. These are used preferably in an amount of 0.02 to 1.00% by mass in the ink composition.

Examples of the antiseptic agent include, for example, organic sulfur-based, organic nitrogen-sulfur-based, organic halogen-based, haloallylsulfone-based, iodopropargyl-based, N-haloalkylthio-based, nitrile-based, pyridine-based, 8-oxyquinoline-based, benzothiazole-based, isothiazoline-based, dithiol-based, pyridineoxide-based, nitropropane-based, organic tin-based, phenol-based, quaternary ammonium salt-based, triazine-based, thiazine-based, anilide-based, adamantane-based, dithiocarbamate-based, brominated indanone-based, benzyl bromoacetate-based, inorganic salt-based compounds, and the like. Specific examples of the organic halogen compound include, for example, sodium pentachlorophenol; specific examples of the pyridineoxide compound include, for example, sodium 2-pyridinethiol-1-oxide; specific examples of the inorganic salt compound include, for example, anhydrous sodium acetate; and the isothiazoline compound includes, for example, 1,2-benzisothiazolin-3-one, 2-n-octyl-4-isothiazolin-3-one, 5-chloro-2-methyl-4-isothiazolin-3-one, 5-chloro-2-methyl-4-isothiazolin-3-one magnesium chloride, 5-chloro-2-methyl-4-isothiazolin-3-one calcium chloride, 2-methyl-4-isothiazolin-3-one calcium chloride or the like. In addition, specific examples of the antiseptic and fungicide include sodium sorbates, sodium benzoates or the like.

As the pH adjuster, any agent can be used as long as it can control the pH of an ink to be formulated in the range of, for example, 5 to 11 without exerting a harmful influence on the ink. Its specific examples include, for example, an alkanolamine such as diethanolamine, triethanolamine or N-methyldiethanolamine or an alkali metal salt of an organic acid such as potassium acetate; an alkali metal hydroxide such as lithium hydroxide, sodium hydroxide or potassium hydroxide; an ammonium hydroxide (ammonia water); or an alkali metal carbonate such as lithium carbonate, sodium carbonate, sodium hydrogen carbonate or potassium carbonate; an inorganic base such as sodium silicate or disodium phosphate; and the like.

Specific examples of the chelating agent include, for example, sodium ethylenediamine tetraacetate, sodium nitrilotriacetate, sodium hydroxyethylethylenediamine triacetate, sodium diethylenetriamine pentaacetate, sodium uracil diacetate or the like.

Specific examples of the rust-preventive agent include, for example, acidic sulfite salts, sodium thiosulfate, ammonium thioglycollate, diisopropylammonium nitrite, pentaerythritol tetranitrate, dicyclohexylammonium nitrite or the like.

Examples of the water-soluble UV absorbing agent include, for example, sulfonated benzophenone compounds, benzotriazole compounds, salicylic acid compounds, cinnamic acid compounds or triazine compounds.

Specific examples of the water-soluble polymer compound include polyvinyl alcohols, cellulose derivatives, polyamines, polyimines or the like.

Specific examples of the dye dissolving agent include, for example, $\epsilon$-caprolactam, ethylene carbonates, ureas or the like.

As for examples of the antioxidant, for example, various antifading agents of organic and metal complex can be used. Examples of the above organic antifading agent include hydroquinones, alkoxyphenols, dialkoxyphenols, phenols, anilines, amines, indanes, chromans, alkoxyanilines, heterocycles, or the like.

Examples of the surfactant include, for example, known surfactants such as anion-, cation- or nonionic-surfactant and the like. Examples of the anionic surfactant include alkyl sulfonate, alkyl carboxylate, $\alpha$-olefin sulfonate, polyoxyethylene alkyl ether acetate, N-acylamino acids and salts thereof, N-acylmethyltaurine salts, alkylsulfate polyoxyalkylether sulfate, alkylsulfate polyoxyethylene alkylether phosphate, rosin acid soap, castor oil sulfate, lauryl alcohol sulfate, alkylphenol phosphate ester, alkyl phosphate ester, alkyl allylsulfonate, diethyl sulfosuccinate, diethylhexyl sulfosuccinate, dioctyl sulfosuccinate or the like. The cationic surfactant includes 2-vinylpyridine derivatives, poly(4-vinylpyridine) derivatives and the like.

Specific examples of the amphoteric surfactant include lauryidimethylaminoacetic acid betaine, 2-alkyl-N-carboxymethyl-N-hydroxyethylimidazolinium betaine, coconut oil fatty acid amide propyldimethylaminoacetic acid betaine, polyoctylpolyaminoethylglycine, and in addition imidazoline derivatives, or the like.

Specific examples of the nonionic surfactant include ethers such as polyoxyethylene nonylphenyl ether, polyoxyethylene octylphenyl ether, polyoxyethylene dodecylphenyl ether, polyoxyethylene oleyl ether, polyoxyethylene lauryl ether and polyoxyethylene alkyl ether; esters such as polyoxyethylene oleic acid, polyoxyethylene oleic acid ester, polyoxyethylene distearic acid ester, sorbitan laurate, sorbitan monostearate, sorbitan monooleate, sorbitan sesquioleate, polyoxyethylene monooleate and polyoxyethylene stearate; acetylene glycols such as 2,4,7,9-tetramethyl-5-decyne-4,7-diol, 3,6-dimethyl-4-octyne-3,6-diol and 3,5-dimethyl-1-hexyne-3-ol (for example, trade names: Surfynol 104, 105, 82 and 465, Olfine STG and the like; manufactured by Nissin Chemical Industry Co., Ltd.), and the like. These ink preparation agents are used alone or as a mixture thereof.

The ink composition of the present invention can be obtained by mixing the above ingredients in any order and stirring them. The obtained ink composition may be, if desired, filtered through a membrane filter or the like to remove impurities. In addition, in order to adjust the black tint as an ink composition, other coloring matters having various hues may be mixed thereto other than the azo compound represented by the formula (1) of the present invention. In that case, coloring matters of black having another hue, yellow, magenta, cyan and other colors can be mixed for use.

The ink composition of the present invention can be used in various fields, however it is suitable for water-based ink for writing, water-based printing ink, information recording ink and the like, and particularly preferably used as ink for inkjet and suitably used in the inkjet recording method of the present invention described later.

Next, the inkjet recording method of the present invention will be explained. The inkjet recording method of the present invention is characterized by using the above ink composition of the present invention to perform recording. In the inkjet recording method of the present invention, recording is performed on an image receiving material using ink for inkjet which comprises the above ink composition, where the ink nozzle and the like to be used are not limited in particular and can be accordingly selected depending on the purpose, and a known method, for example, a charge control method where ink is discharged utilizing electrostatic induction force, a drop-on-demand method (a pressure pulse method) where oscillating pressure of piezo elements are utilized, an acoustic inkjet method where electric signals are converted to acoustic beams which is then irradiated to ink and the ink is discharged by the radiation pressure, a thermal inkjet (bubble jet (registered trademark)) method where pressure generated by forming bubbles by heating ink is utilized or the like is employed. In addition, the above inkjet recording method includes a method where a lot of small volumes of ink having a low concentration called photo ink are injected, a method where image quality is improved using a plural of inks having substantially the same hue and a different concentration, or a method where a colorless and transparent ink is used.

The colored article of the present invention is an article colored with the above compound of the present invention or an ink composition containing this, and more preferably an article colored by an inkjet printer using the ink composition of the present invention. Articles to be colored include, for example, communication sheets such as paper and film, fiber and cloth (cellulose, nylon, wool and the like), leather, substrate for color filters and the like. The communication sheet among them is preferably provided with a surface treatment, specifically one where a substrate such as paper, synthetic paper or film is provided with an ink receiving layer. The ink receiving layer can be provided, for example, by impregnation or coating of a cation polymer on the above substrates, or by coating, on the surface of the above substrates, of a porous white inorganic substance, such as porous silica, aluminasol or special ceramics, which can absorb the coloring mater in ink, together with a hydrophilic property polymer such as polyvinyl alcohol or polyvinylpyrrolidone. Paper provided with such an ink receiving layer are usually called inkjet special paper (film), glossy paper (film) and the like, and commercially available as, for example, Professional Photopaper, Super Photopaper or Matte Photopaper (all are trade names; manufactured by Canon Inc.), Photo Paper (glossy), PM Matte Paper or Crispia (all are trade names; manufactured by Seiko-Epson Corporation), Advanced Photo Paper, Premium Plus Photo Paper, Premium Glossy Film or Photo Paper (all are trade names; manufactured by Hewlett Packard Japan, Ltd.), PhotoLike QP (trade name, manufactured by KONICA Corporation) and the like. In addition, it goes without saying that plain paper can be used.

Among them, it is known that discoloration or fading of images recorded on a communication sheet whose surface is coated with a porous white inorganic substance particularly becomes more evident by ozone gas. The ink composition of the present invention has an effect especially in recording on such a record-receiving material due to its excellent ozone gas fastness.

In order to record on a record-receiving material such as communication sheet by the inkjet recording method of the present invention, for example, a container containing the above ink composition is set in the predetermined position of an ink jet printer and recording can be performed on a record-receiving material in a usual manner. In the inkjet recording method of the present invention, the black ink composition of the present invention can be used in combination with a magenta ink composition, a cyan ink composition, a yellow ink composition, if needed, a green ink composition, a blue (or violet) ink composition and a red (or orange) ink composition which are known. Each color ink composition is charged into each container, which is then loaded in each predetermined position of an ink jet printer in the same way as the container containing the water-based black ink composition for inkjet recording of the present invention for use.

The azo compound of the present invention has excellent water-solubility and the ink composition of the present invention containing this azo compound exhibits no crystal precipitation or no change in physical properties and color after storage for a long period of time, and has good storage stability. In addition, the black ink composition for recording which contains the trisazo compound of the present invention is used for inkjet recording and writing tools, and when recording is performed on a plain paper and an inkjet special paper with it, the recorded images exhibit black having a high print density and are also excellent in ozone gas fastness, light fastness and bronzing resistance.

EXAMPLES

Hereinafter, the present invention will be explained more specifically by the examples, but the present invention is not limited whatsoever by the following examples. In this connection, "part(s)" and "%" in the examples are based on mass unless otherwise specifically noted. In addition, in the following formulas, the sulfo group is represented in free acid form.

Example 1-1

(1) In 40 parts of water, 5.4 parts of a compound of the following formula (12) (C.I. Acid Yellow 9) was suspended and then dissolved with the pH value adjusted to 4.0 to 5.0 by addition of sodium hydroxide. In this solution, 6.0 parts of 35% hydrochloric acid was added and then 2.9 parts of a 40% aqueous sodium nitrite solution was added at 15 to 25° C. for diazotization.

The formula (12)

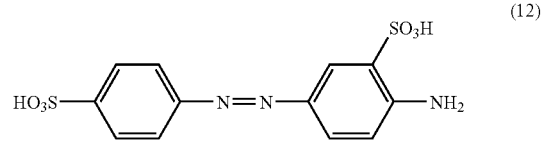

Separately, in 30 parts of water, 3.6 parts of a compound of the following formula (13) obtained by the method described in JP 2004-083492 was dissolved at pH 4.5 to 5.5 adjusted by addition of sodium hydroxide. In this solution, the diazo suspension obtained in the above (1) was added dropwise at 15 to 25° C. over about 30 minutes. During the dropwise addition, the pH value of the solution was maintained at 3.5 to 4.5 by addition of sodium carbonate. Thereafter, it was stirred for 2 hours and salted out by addition of sodium chloride, and the precipitate was separated by filtration to obtain a wet cake containing a disazo compound of the following formula (14).

The formula (13)

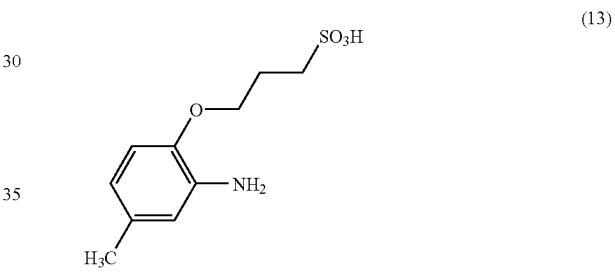

The formula (14)

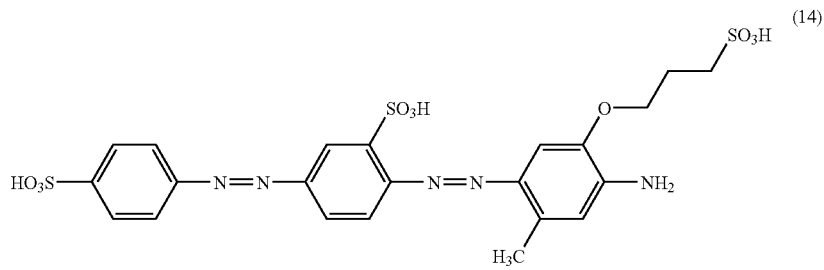

(2) 2-(cyanomethyl)benzimidazole and ethyl acetoacetate was reacted by heating in ethanol in the presence of sodium methoxide, followed by aciding out by addition of dilute hydrochloric acid to obtained a compound of the following formula (15). In 64 parts of 6% fuming sulfuric acid, 8.9 parts of said compound obtained was slowly added at 15 to 25° C. After the addition, it was stirred at the same temperature for 2 hours, and then added dropwise in 190 parts of ice water over about 10 minutes. The precipitated crystal was separated by filtration and dried to obtain 10.7 parts of a compound of the formula (16).

The formula (15)

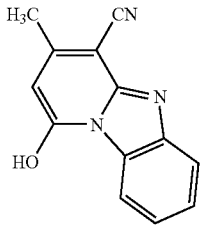
(15)

The formula (16)

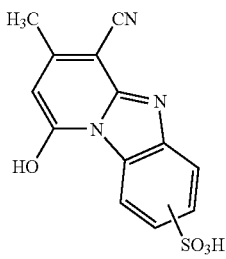
(16)

(3) The wet cake containing the disazo compound of the formula (14) obtained in the above (1) was, with the pH value adjusted to 6.0 to 7.0 by addition of sodium hydroxide, dissolved in 80 parts of water, 2.3 parts of a 40% aqueous sodium nitrite solution was added thereto, and then this solution was added dropwise in a mixed solution of 5.2 parts of 35% hydrochloric acid and 70 parts of water at 20 to 30° C. for diazotization. This diazo suspension was added dropwise at 20 to 30° C. in a solution where 3.0 parts of the compound of the formula (16) obtained in (2) was, with the pH value adjusted to 8.0 to 9.0 by addition of sodium hydroxide, dissolved in 50 parts of water. During the dropwise addition, the pH value was maintained at 7.0 to 8.0 by addition of sodium carbonate. After dropwise addition, it was stirred at the same temperature for 2 hours and salted out by addition of sodium chloride, and the precipitate was separated by filtration. The obtained wet cake was dissolved in 60 parts of water and then crystallized by addition of 100 parts of methanol, and the precipitate was separated by filtration. The obtained wet cake was further dissolved in 50 parts of water and then crystallized by addition of 120 parts of methanol, and the precipitate was separated by filtration and dried to obtain 8.2 parts of a trisazo compound of the formula (17) of the present invention (Compound No. 1 in Table 2) as a sodium salt. The maximum absorption wavelength (λmax) of this compound in an aqueous solution of pH 7 to 8 was 554 nm and the solubility was 100 g/L or more.

The formula (17)

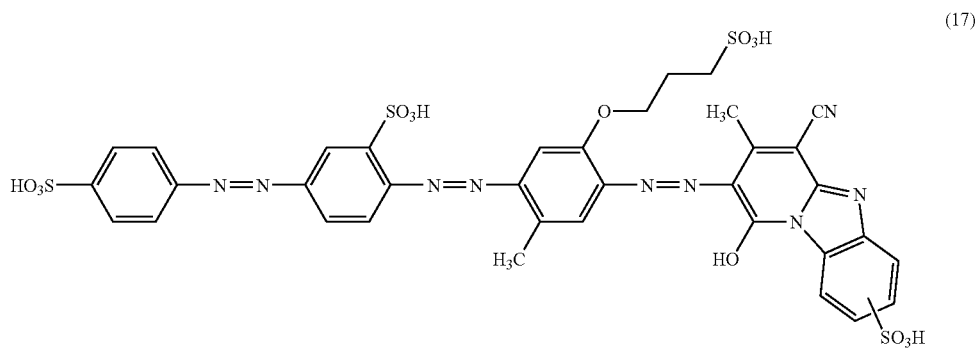
(17)

Example 1-2

(1) In the same manner as in Example 1-1 except that the stirring was conducted at 30 to 35° C. for 6 hours in the stirring process after adding the compound of the formula (15) in the 6% fuming sulfuric acid in (2) of Example 1-1, 10.3 parts of a compound of the formula (18) was obtained.

The formula (18)

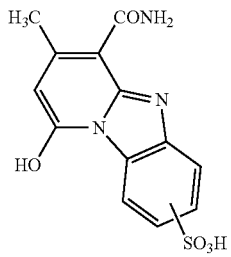
(18)

(2) In the same manner as in Example 1-1 except that 3.2 parts of the compound of the above formula (18) was used instead of 3.0 parts of the compound of the formula (16) in (3) of Example 1-1, 8.0 parts of a trisazo compound of a formula (19) of the present invention (Compound No. 2 in Table 2) was obtained as a sodium salt. The maximum absorption wavelength (λmax) of this compound in an aqueous solution of pH 7 to 8 was 545 nm and the solubility was 100 g/L or more.

The formula (19)

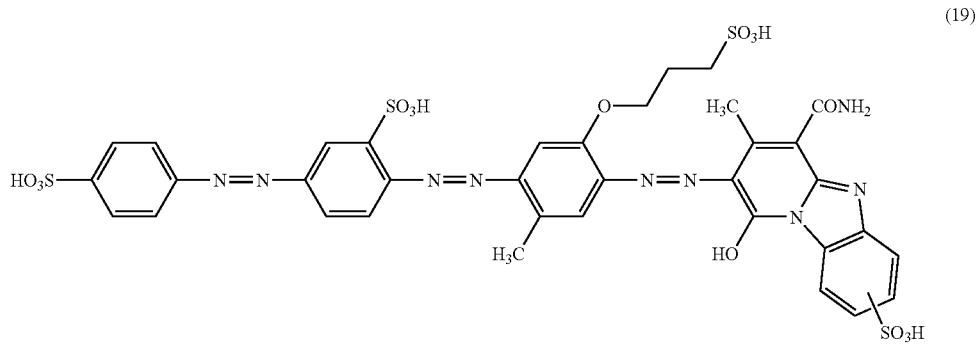

Example 1-3

(1) In 100 parts of water, 21.7 parts of 5-sulfoanthranilic acid was dissolved at pH 5.0 to 6.0 adjusted by addition of sodium hydroxide. In said solution, 31.3 parts of 35% hydrochloric acid was added, followed by adjusting to 0 to 5° C., and 19.0 parts of a 40% aqueous sodium nitrite solution added thereto for diazotization. In this diazo solution, a solution where 24.0 parts of the compound of the formula (13) was, with the pH value adjusted to 4.5 to 5.5 by addition of sodium hydroxide, dissolved in 240 parts of water was added dropwise over about 20 minutes. After the dropwise addition, sodium carbonate was added thereto at 10 to 20° C. to adjust the pH value to 2.0 to 3.0, and the solution was stirred for 3 hours while maintaining the same temperature and pH. After the stirring, it was salted out by addition of sodium chloride, and this precipitate was separated by filtration and dried to obtain 42.1 parts of a compound of the following formula (20).

The formula (20)

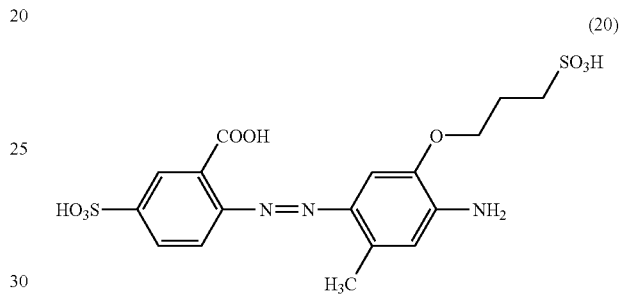

(2) In the same manner as in Example 1-1 except that 7.1 parts of the compound of the above formula (20) was used instead of 5.4 parts of the compound of the formula (12) in (1) of Example 1-1, 8.9 parts of a trisazo compound of the formula (21) of the present invention (Compound No. 6 in Table 2) was obtained as a sodium salt. The maximum absorption wavelength (λmax) of this compound in an aqueous solution of pH 7 to 8 was 553 nm and the solubility was 100 g/L or more.

The formula (21)

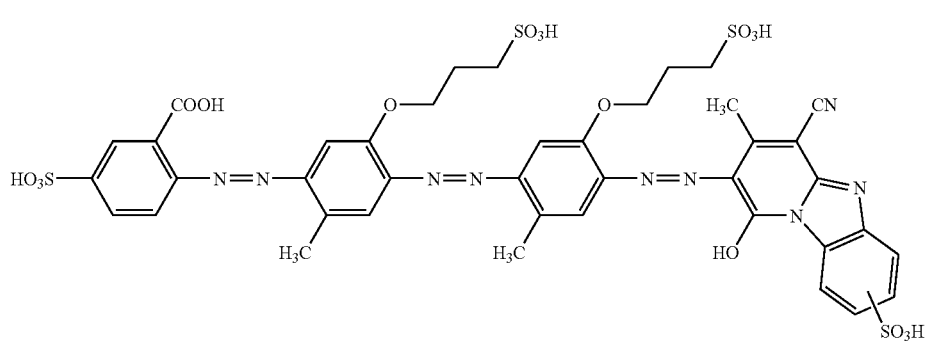

Example 1-4

In the same manner as in Example 1-3 except that the compound of the formula (18) was used instead of the compound of the formula (16) used in the process of (3) of Example 1-1, in (2) of Example 1-3, 8.7 parts of a trisazo compound of the formula (22) of the present invention (Compound No. 7 in Table 3) was obtained as a sodium salt. The maximum absorption wavelength (λmax) of this compound in an aqueous solution of pH 7 to 8 was 557 nm and the solubility was 100 g/L or more.

The formula (22)

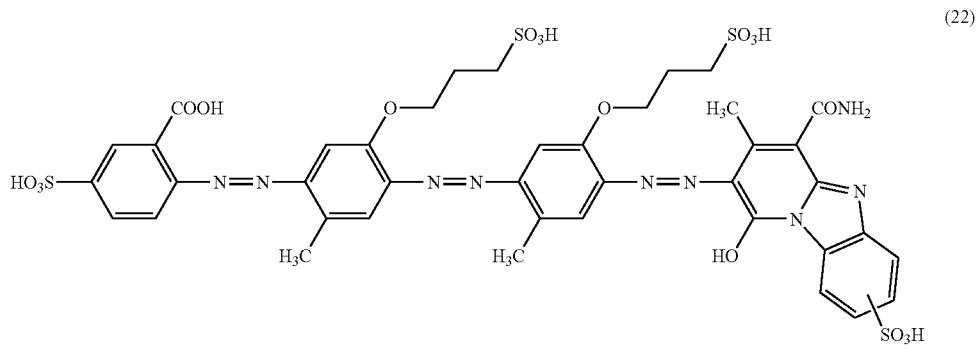

Example 1-5

In the same manner as in Example 1-1 except that 3-keto-n-hexanoic acid ethyl ester was used instead of ethyl acetoacetate in (2) of Example 1-1, parts of a trisazo compound of the formula (23) of the present invention (Compound No. 3 in Table 2) was obtained as a sodium salt. The maximum absorption wavelength (λmax) of this compound in an aqueous solution of pH 7 to 8 was 555 nm and the solubility was 100 g/L or more.

The formula (23)

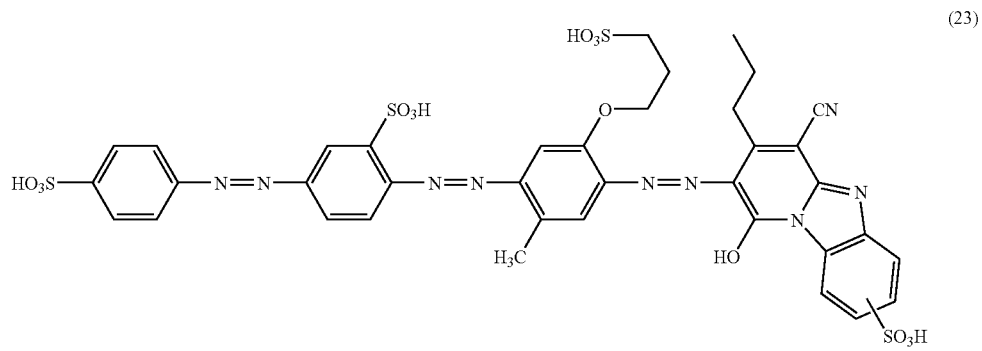

Example 1-6

In the same manner as in Example 1-1 except that ethyl benzoylacetate was used instead of ethyl acetoacetate in (2) of Example 1-1, 8.4 parts of a trisazo compound of the formula (24) of the present invention (Compound No. 4 in Table 2) was obtained as a sodium salt. The maximum absorption wavelength (λmax) of this compound in an aqueous solution of pH 7 to 8 was 548 nm and the solubility was 100 g/L or more.

The formula (24)

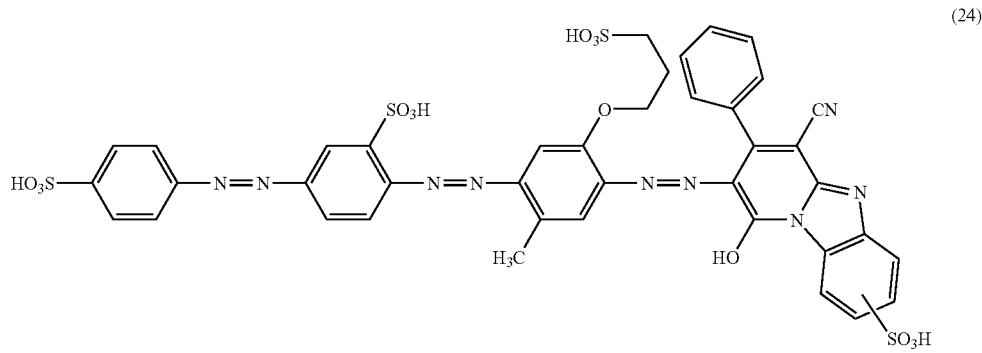

Examples 1-7 to 1-10

(A) Preparation of Ink

The ingredients described in the following table 4 were mixed in the ratio described there to obtain a black ink composition of the present invention, which was then filtered through a 0.45 μm membrane filter to remove foreign substances.

In this connection, ion-exchanged water was used as water. In addition, the ratio of water+sodium hydroxide in Table 4 is a ratio at the time when, in ink preparation, the pH of the ink was adjusted to pH7 to 9 with sodium hydroxide and then ion-exchanged water was added thereto to adjust the concentration of the example compound to 5% so that the total amount was 100 parts.

TABLE 4

| | |
|---|---|
| Each compound obtained in the above Examples 1-1 to 1-4 | 5.0 parts |
| Glycerine | 5.0 parts |
| Urea | 5.0 parts |
| N-methyl-2-pyrolidone | 4.0 parts |
| Isopropyl alcohol | 3.0 parts |
| Butylcarbitol | 2.0 parts |
| Surfactant (Trade name: Surfynol105, manufactured by Nissin Chemical Industry Co., Ltd.) | 0.1 part |
| Water + sodium hydroxide | 75.9 parts |
| Total | 100.0 parts |

Examples 1-7, 1-8, 1-9 and 1-10 are for tests using each compound of the formula (17), the formula (19), the formula (21) and the formula (22) obtained in the above examples 1-1, 1-2, 1-3 and 1-4 in Table 4. Precipitation and separation did not occur in these water-based ink compositions during storage, and in addition, change in physical properties did not occur after storage for a long period of time.

Comparative Example 1

As a water-soluble coloring matter for inkjet for comparison, an ink composition was prepared with the same composition as in Examples 1-7 to 1-10, using a coloring matter (the following formula (25)) of 1 in Table 1-1 of Patent Literature 1.
The formula (25)

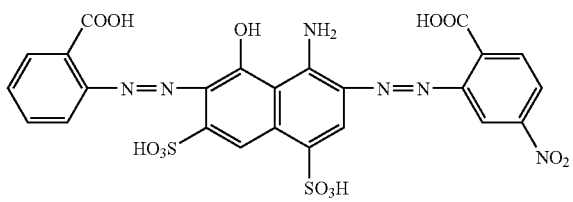

(25)

Comparative Example 2

Similarly to Comparative Example 1, as a water-soluble coloring matter for inkjet for comparison, an ink composition was prepared with the same composition of Examples 1-7 to 1-10, using a coloring matter AN-250 (the following formula (26)) explained in Example 1 of Patent Literature 3.
The formula (26)

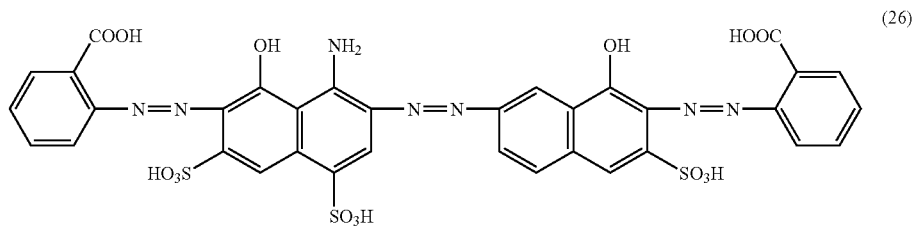

(26)

(B) Inkjet Printing

Using the ink composition obtained above, inkjet recording was performed on two kinds of paper, special glossy paper 1 (manufactured by Canon Inc., trade name: Professional Photopaper PR-101) and special glossy paper 2 (manufactured by Seiko-Epson Corporation, trade name: Photo Paper (Glossy) KA420PSK) by an ink jet printer (trade name PIXUS iP7100, manufactured by Canon Inc.). In printing, such an image pattern was made that several graduations of reflection density were obtained, and black printed matters were obtained.

Evaluation of light fastness test and ozone gas fastness test was conducted by a calorimeter (trade name: Spectro Eye, manufactured by GretagMacbeth AG), using the graduation part of the printed matters where the reflection density D value before the test was the nearest to 1.0.

(C) Evaluation of Recorded Image

The recorded images with the water-based ink composition of the present invention were evaluated on change of the density after light fastness test and ozone gas fastness test. In this connection, the tests were conducted on special glossy paper 1 and 2. The results are shown in Table 5. The specific test method is described below.

1) Light Fastness Test

Using a xenon weatherometer (trade name: Ci4000, manufactured by ATRAS Electric Devices Co.), irradiation was conducted for 50 hours under the conditions of an illuminance of 0.36 W/m², a humidity of 60% RH and a temperature of 24° C. After the test, colorimeter was conducted using the above colorimeter and the residual rates of the coloring matter were determined by (reflection density after the test/reflection density before the test)×100(%) to evaluate according to the following criteria.
  ○ Residual rate: 90% or more
  Δ Residual rate: under 90% and 80% or more
  x Residual rate: under 80%
The results are shown in Table 5.

2) Ozone Gas Fastness Test

Using an ozone weatherometer (trade name, manufactured by Suga Test Instruments Co., Ltd.), the printed samples were left for 4 hours at an ozone concentration of 12 ppm, a humidity of 60% RH and a temperature of 24° C. After the test, colorimeter was conducted using the above colorimeter and the residual rates of the coloring matter were determined by (reflection density after the test/reflection density before the test)×100(%) to evaluate according to the following criteria.

○ Residual rate: 70% or more
Δ Residual rate: 60% or more and under 70%
x Residual rate: under 60%

The results are shown in Table 5. In addition, the results of Example 2-10 are also shown in Table 5.

TABLE 5

|  | Light fastness | Ozone gas fastness |
|---|---|---|
| Example 1-7 (the formula (17)) | | |
| Special glossy paper 1 | ○ | ○ |
| Special glossy paper 2 | ○ | ○ |
| Example 1-8 (the formula (19)) | | |
| Special glossy paper 1 | ○ | ○ |
| Special glossy paper 2 | ○ | ○ |
| Example 1-9 (the formula (21)) | | |
| Special glossy paper 1 | ○ | ○ |
| Special glossy paper 2 | ○ | ○ |
| Example 1-10 (the formula (22)) | | |
| Special glossy paper 1 | ○ | ○ |
| Special glossy paper 2 | ○ | ○ |
| Example 2-10 (the formula (36)) | | |
| Special glossy paper 1 | ○ | ○ |
| Special glossy paper 2 | ○ | ○ |
| Comparative Example 1 (the formula (25)) | | |
| Special glossy paper 1 | x | x |
| Special glossy paper 2 | Δ | ○ |
| Comparative Example 2 (the formula (26)) | | |
| Special glossy paper 1 | x | x |
| Special glossy paper 2 | Δ | ○ |

As is clear from the results of Table 5, the images recorded with the ink compositions containing the azo compound of the present invention exhibited equal fastness or better fastness with regard to ozone gas fastness in comparison with the images of the conventional black dyes (Comparative Examples), and had good results on any of special glossy papers. That is, the residual rate of the coloring matter was under 60% in the case of using Special glossy paper 1 in Comparative Examples 1 and 2, while the residual rate of the coloring matter was 70% or more even in the case of using any of the special glossy papers in Examples 1-7 to 1-10 and 2-10 of the present invention. In addition, there appeared obvious difference in light fastness, which is because the residual rate of the coloring matter was 90% or more (○) even in the case of using any of the special glossy papers in Examples 1-7 to 1-10 and 2-10 where the ink compositions containing the azo compound of the present invention were used, while the residual rate of the coloring matter was under 90% and 80% or more (Δ) in any case of using Special glossy paper 2 and also the residual rate of the coloring matter was under 80% in any case of using Special glossy paper 1, in Comparative Examples 1 and 2. Judging from these results, it is found that Examples 1-7 to 1-10 and 2-10 of the present invention show significantly good results in comparison with Comparative Examples and the fastnesses of the images recorded with the trisazo compound of the present invention are extremely excellent.

Further, the azo compound of the present invention is high in solubility and stable enough to make it possible to design inks having a high concentration.

Example 2-1

In 20 parts of 95% sulfuric acid, 3.0 parts of the compound of the formula (16) was dissolved, heated to 60° C. and then stirred for 1.5 hours. The reaction solution was cooled to room temperature, and then added dropwise in 60 parts of ice water, followed by addition of sodium chloride and then by separation of the crystal by filtration. The crystal was washed on a funnel with dilute hydrochloric acid water dissolving sodium chloride and then dried to obtain 2.5 parts of a compound of the above formula (18).

Example 2-2

(1) In the same manner as in (1) of Example 1-3 except that 18.1 parts of 5-aminoisophthalic acid was used instead of 21.7 parts of 5-sulfoanthranilic acid in (1) of Example 1-3, a compound of the following formula (27) was obtained.

The formula (27)

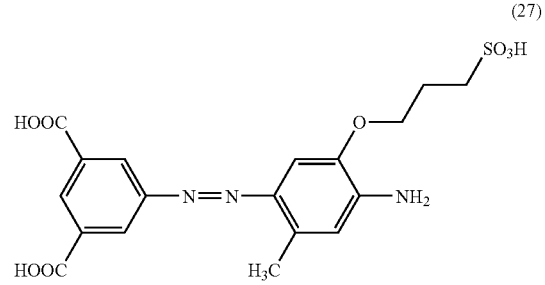

(2) In the same manner as in Example 1-1 except that 6.6 parts of the compound of the above formula (27) was used instead of 5.4 parts of the compound of the formula (12) in (1) of Example 1-1, 8.5 parts of a trisazo compound of the following formula (28) (Compound No. 13 in Table 6) was obtained as a sodium salt. The maximum absorption wavelength (λmax) of this compound in an aqueous solution of pH 7 to 8 was 554.5 nm and the solubility was 100 g/L or more.

The formula (28)

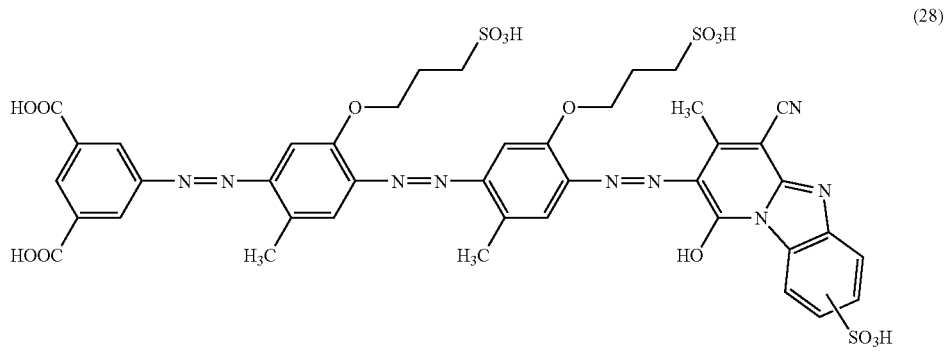

Example 2-3

(1) In the same manner as in (1) of Example 1-3 except that 24.0 parts of sodium 2-amino-5-nitrobenzenesulfonate was used instead of 21.7 parts of 5-sulfoanthranilic acid in (1) of Example 1-3, a compound of the following formula (29) was obtained.
The formula (29)

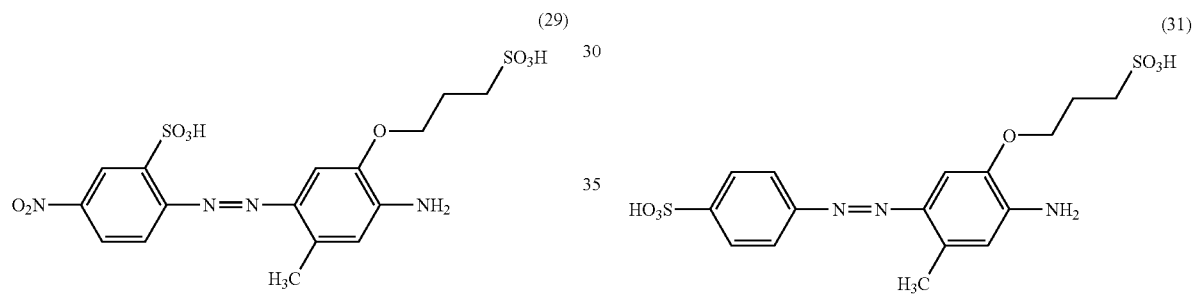

(2) In the same manner as in Example 1-1 except that 7.1 parts of the compound of the above formula (29) was used instead of 5.4 parts of the compound of the formula (12) in (1) of Example 1-1, 8.9 parts of a trisazo compound of the formula (30) of the present invention (Compound No. 14 in Table 6) was obtained as a sodium salt. The maximum absorption wavelength (λmax) of this compound in an aqueous solution of pH 7 to 8 was 559.5 nm and the solubility was 100 g/L or more.
The formula (30)

Example 2-4

(1) In the same manner as in (1) of Example 1-3 except that 17.3 parts of 4-aminobenzenesulfonic acid was used instead of 21.7 parts of 5-sulfoanthranilic acid in (1) of Example 1-3, a compound of the following formula (31) was obtained.
The formula (31)

(2) In the same manner as in Example 1-1 except that 6.4 parts of the compound of the above formula (31) was used instead of 5.4 parts of the compound of the formula (12) in (1) of Example 1-1, 8.2 parts of a trisazo compound of the formula (32) of the present invention (Compound No. 15 in Table 6) was obtained as a sodium salt. The maximum absorption wavelength (λmax) of this compound in an aqueous solution of pH 7 to 8 was 558.5 nm and the solubility was 100 g/L or more.

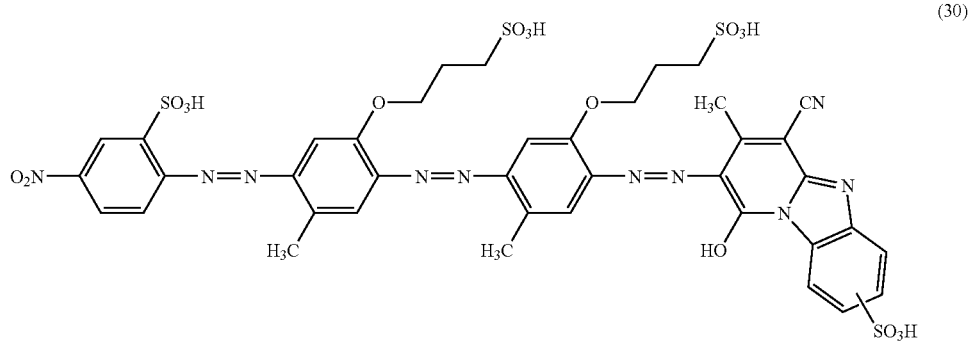

The formula (32)

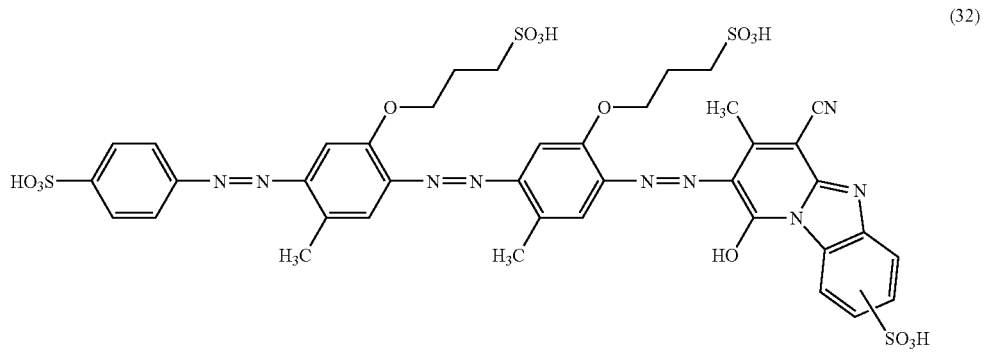

Example 2-5

(1) In the same manner as in (1) of Example 1-3 except that 27.5 parts of monosodium 2-aminobenzene-1,4-disulfonate was used instead of 21.7 parts of 5-sulfoanthranilic acid in (1) of Example 1-3, a compound of the following formula (33) was obtained.
The formula (33)

Example 2-6

(1) In the same manner as in (1) of Example 1-3 except that 25.3 parts of 2-aminobenzene-1,5-disulfonic acid was used instead of 21.7 parts of 5-sulfoanthranilic acid in (1) of Example 1-3, a compound of the following formula (35) was obtained.
The formula (35)

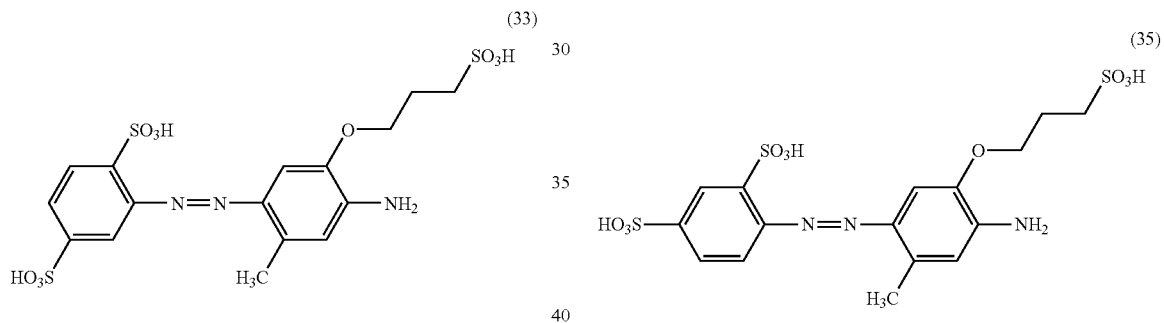

(2) In the same manner as in Example 1-1 except that 7.6 parts of the compound of the above formula (33) was used instead of 5.4 parts of the compound of the formula (12) in (1) of Example 1-1, 9.0 parts of a trisazo compound of the formula (34) of the present invention (Compound No. 16 in Table 6) was obtained as a sodium salt. The maximum absorption wavelength (λmax) of this compound in an aqueous solution of pH 7 to 8 was 552.5 nm and the solubility was 100 g/L or more.
The formula (34)

(2) In the same manner as in Example 1-1 except that 7.6 parts of the compound of the above formula (35) was used instead of 5.4 parts of the compound of the formula (12) in (1) of Example 1-1, 9.0 parts of a trisazo compound of the formula (36) of the present invention (Compound No. 17 in Table 6) was obtained as a sodium salt. The maximum absorption wavelength (λmax) of this compound in an aqueous solution of pH 7 to 8 was 557.5 nm and the solubility was 100 g/L or more.

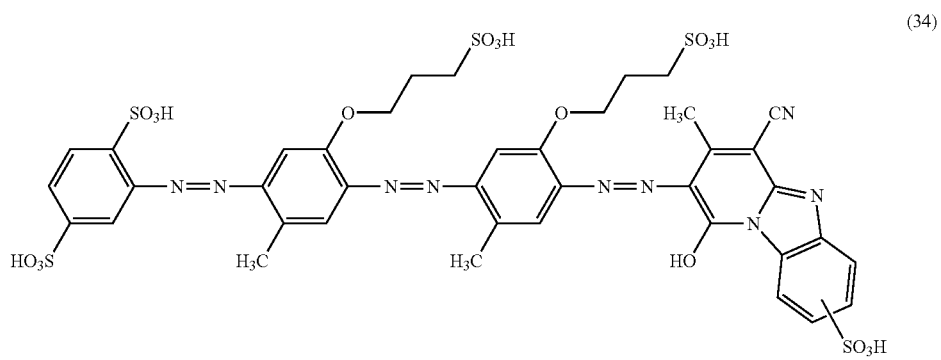

The formula (36)

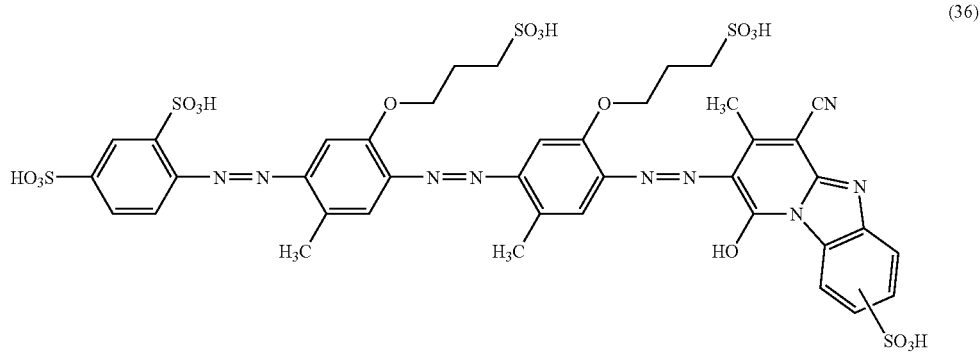

Example 2-7

(1) A mixed solution of 25.0 parts of 4-hydroxyacetanilide, 25.5 parts of potassium carbonate and 120 parts of 2-propanol was heated to 80° C., and a solution dissolving 22.6 parts of propane sultone in 60 parts of 2-propanol was added dropwise hereto. After the dropwise addition, the solution was stirred at 80° C. for 3 hours. It was cooled to room temperature and then a solution where 60 parts of 35% hydrochloric acid was diluted with 40 parts of water was added dropwise thereto. It was heated to 80° C. and stirred for 2.5 hours while distilling some of the solvent away, followed by stirring at 100° C. for 1 hour. It was cooled to room temperature and then the precipitate was separated by filtration and dried to obtain 34 parts of a compound of the following formula (37).

The formula (37)

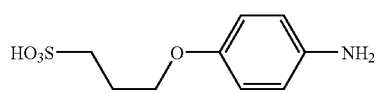

(2) In the same manner as in (1) of Example 1-3 except that 23.1 parts of the compound of the formula (37) obtained in the above reaction was used instead of 21.7 parts of 5-sulfoanthranilic acid in (1) of Example 1-3, a compound of the following formula (38) was obtained.

The formula (38)

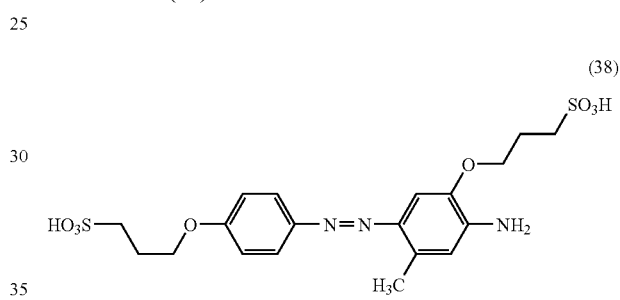

(3) In the same manner as in Example 1-1 except that 7.3 parts of the compound of the above formula (38) was used instead of 5.4 parts of the compound of the formula (12) in (1) of Example 1-1, 9.2 parts of a trisazo compound of the formula (39) of the present invention (Compound No. 18 in Table 7) was obtained as a sodium salt. The maximum absorption wavelength (λmax) of this compound in an aqueous solution of pH 7 to 8 was 564.0 nm and the solubility was 100 g/L or more.

The formula (39)

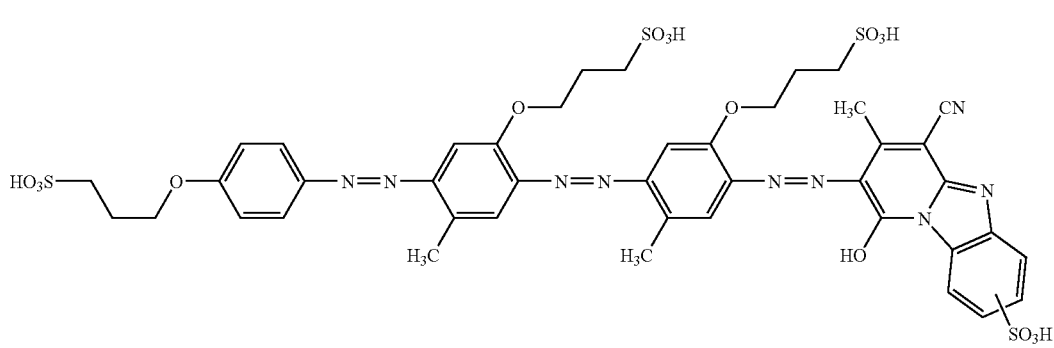

Example 2-8

(1) In the same manner as in (1) of Example 1-3 except that 20.3 parts of 2-amino-5-methoxybenzenesulfonic acid was used instead of 21.7 parts of 5-sulfoanthranilic acid in (1) of Example 1-3, a compound of the following formula (40) was obtained.

The formula (40)

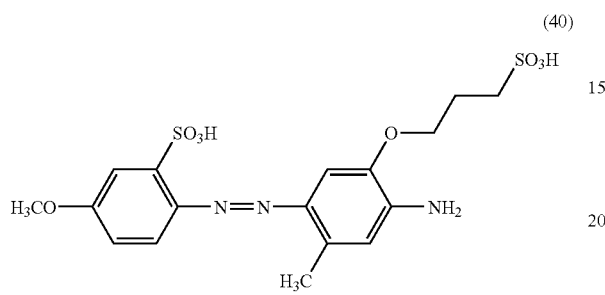

(2) In the same manner as in Example 1-1 except that 6.9 parts of the compound of the above formula (40) was used instead of 5.4 parts of the compound of the formula (12) in (1) of Example 1-1, 8.9 parts of a trisazo compound of the formula (41) of the present invention (Compound No. 19 in Table 7) was obtained as a sodium salt. The maximum absorption wavelength (λmax) of this compound in an aqueous solution of pH 7 to 8 was 562.5 nm and the solubility was 100 g/L or more.

The formula (41)

room temperature, 20 parts of water was added and then a solution where 42 parts of 35% hydrochloric acid was diluted with 20 parts of water was added dropwise thereto. It was heated to 80° C. and stirred for 2.5 hours while distilling some of the solvent away, followed by stirring at 100° C. for 2 hours. It was cooled to room temperature and then salted out by addition of sodium chloride, and the precipitate was separated by filtration and dried to obtain 22.0 parts of a compound of the following formula (42).

The formula (42)

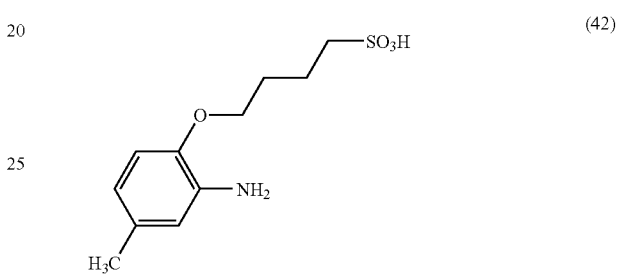

(2) In the same manner as in Example 1-1 except that 3.8 parts of the compound of the above formula (42) was used instead of 3.6 parts of the compound of the formula (13) in (1) of Example 1-1, 8.2 parts of a trisazo compound of the formula (43) of the present invention (Compound No. 20 in Table 7) was obtained as a sodium salt. The maximum absorption wavelength (λmax) of this compound in an aqueous solution of pH 7 to 8 was 555.5 nm and the solubility was 100 g/L or more.

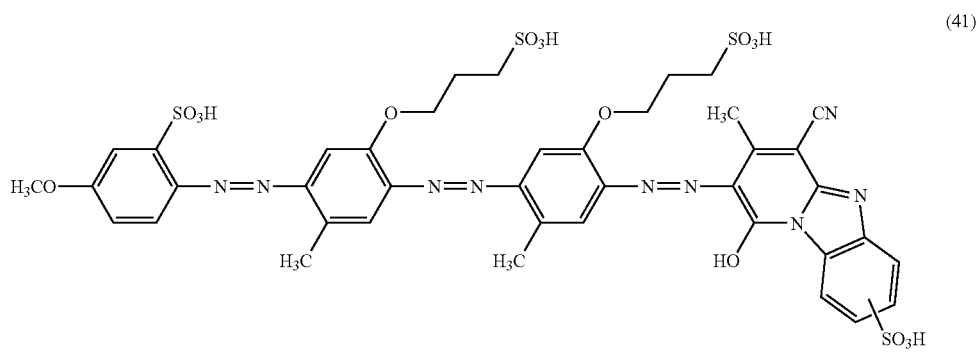

Example 2-9

(1) A mixed solution of 20.1 parts of 2-acetylamino-p-cresol, 18.8 parts of potassium carbonate and 90 parts of 2-propanol was heated to 80° C. and 18.3 parts of Butane sultone was added dropwise hereto. After the dropwise addition, the solution was stirred at 80° C. for 2 hours. After it was cooled to The formula (43)

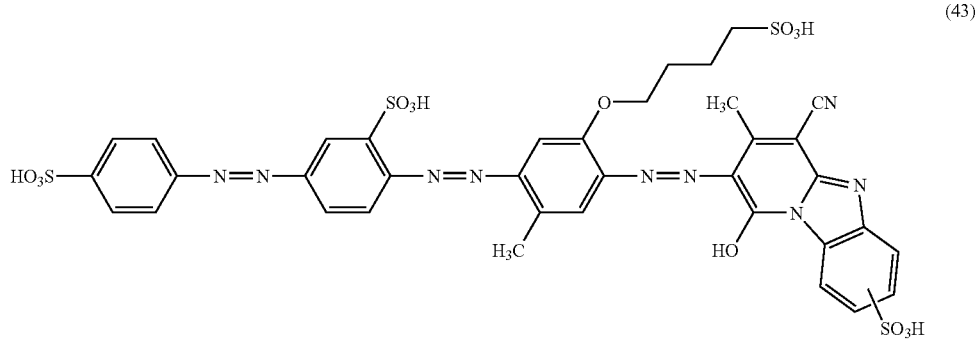

(43)

Example 2-10

By performing the same operation as in the above Examples 1-7 to 1-10 in (A) Preparation of Ink except that the above compound (36) obtained in Example 2-6 was used instead of the above compounds obtained in Examples 1-1 to 1-4, an ink was prepared. Example 2-10 is for a test by using this ink. The results of the test in Example 2-10 are shown in Table 5 described above. This water-based ink composition exhibited no precipitation during storage and also no change of physical properties even after storage for a long period of time.

Synthesis Example 1

(1) 6.4 parts of 2-amino-5-naphthole-1,7-disulfonic acid and 4.1 parts of p-toluenesulfonyl chloride were reacted at pH 8.0 to 8.5 and 70° C. for 1 hour and then salted out under acidic condition, and the precipitate was separated by filtration to obtain a compound of the following formula (66). In 90 parts of water, 8.8 parts of said compound was dissolved while adjusting to pH 6.0 to 8.0 with sodium carbonate. After 6.8 parts of 35% hydrochloric acid was added thereto, said solution was cooled to 0 to 5° C. and 3.6 parts of a 40% aqueous sodium nitrite solution was added thereto for diazotization. The formula (66)

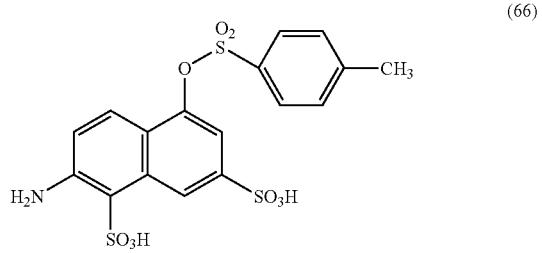

(66)

In this diazo suspension, 5.8 parts of 4-amino-5-naphthole-1,7-disulfonic acid suspended in 60 parts in water was added. Said suspension was stirred at 10 to 20° C. for 4 hours while maintaining the pH value at 2.4 to 2.8 with sodium carbonate. Next, the pH value of the obtained reaction solution was adjusted to 7.0 to 8.5 with sodium carbonate to precipitate a solid, which was then dissolved to obtain a solution containing a monoazo compound of the formula (67).

The formula (67)

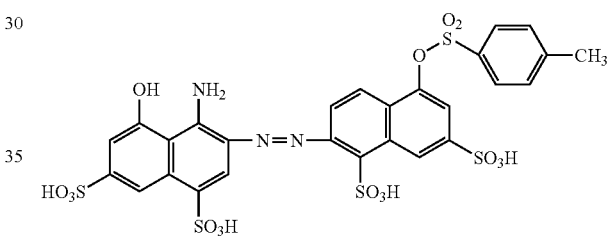

(67)

(2) In 50 parts of water, 5.2 parts of sodium 4-nitroaniline-2-sulfonate was dissolved, and 6.4 parts of 35% hydrochloric acid and 4.0 parts of 40% aqueous sodium nitrite solution were added hereto at 0 to 5° C. for diazotization. The obtained suspension was added dropwise, at 10 to 20° C., in the above solution containing the compound of the formula (67) obtained in above (1), while maintaining the pH value to 8.0 to 9.0 with sodium carbonate. After completion of the dropwise addition, it was stirred at 15 to 30° C. for 2 hours at pH 8.0 to 9.0 to obtain a solution containing a compound of the formula (68).

The formula (68)

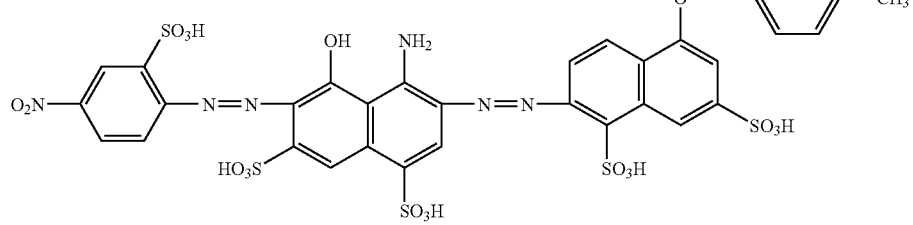

(68)

The above obtained solution was heated to 70° C., and then stirred for 1.5 hours while maintaining the pH value at 10.5 to 11.0 with sodium hydroxide. It was cooled to room temperature and then, at pH 7.0 to 8.0 adjusted with 35% hydrochloric acid, salted out by addition of sodium chloride, and the precipitate was separated by filtration to obtain a wet cake containing a compound of the formula (69).

The formula (69)

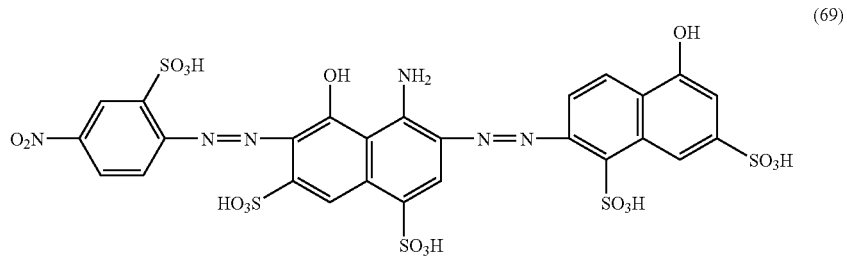

(3) In 130 parts of water, 15.3 parts of a compound of the following formula (70) obtained by the method described in Patent Literature 13 (which is obtained by that the reaction solution was, with the pH value adjusted to 0.5 or under with 35% hydrochloric acid, subjected to aciding out and the precipitate was separated by filtration and dried) was added and dissolved at pH 6.0 to 7.0 adjusted with sodium hydroxide, and 7.7 parts of 35% hydrochloric acid and 4.0 parts of a 40% aqueous sodium nitrite solution were added hereto at 0 to 5° C. for diazotization.

The formula (70)

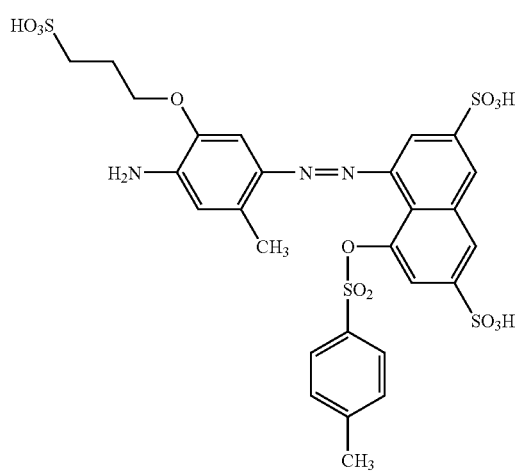

Next, in 30 parts of water 4.9 parts of the compound of the above formula (13) was dissolved at pH 4.5 to 5.5 adjusted by addition of sodium hydroxide, and this solution was added dropwise in the above diazotization reaction solution at 15 to 25° C. over about 30 minutes. After completion of the dropwise addition, the pH value was adjusted to 3.5 to 4.5 by addition of sodium carbonate, the solution was then stirred for 2 hours, the pH value was adjusted to 7.0 to 8.0 by further addition of sodium carbonate to complete the coupling reaction, sodium chloride was added for salting out, and the precipitate was separated by filtration to obtain a wet cake containing a compound of the following formula (72).

The formula (72)

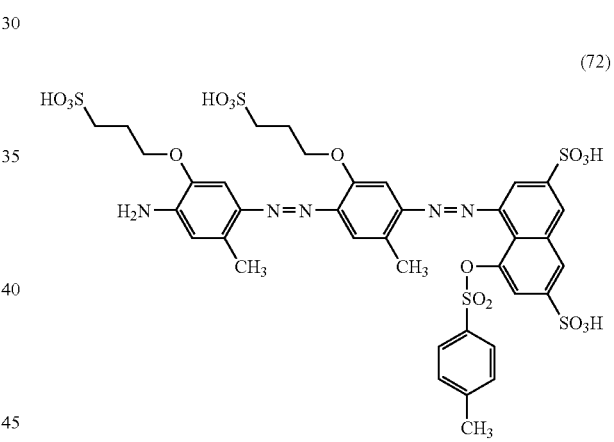

(4) The wet cake containing the compound of the formula (72) obtained in the above (3) was, with the pH value adjusted to 6.0 to 7.0 by addition of sodium hydroxide, dissolved in 80 parts of water, and 8.3 parts of 35% hydrochloric acid and 3.0 parts of a 40% aqueous sodium nitrite solution were added thereto for diazotization to obtain a diazo suspension. On the other hand, the wet cake containing the compound of the formula (69) obtained in the above (2) was added in 120 parts of water, and the pH value was adjusted to 8.0 to 9.0 by addition of sodium hydroxide to dissolve said cake. In the obtained solution, the above obtained diazo suspension of the compound of the formula (72) was added dropwise at 20 to 30° C. During the dropwise addition, the pH value was maintained at 8.0 to 9.0 by addition of sodium carbonate. After the dropwise addition, the solution was stirred at the same temperature for 2 hours and the coupling reaction was completed to obtain a reaction solution containing a compound of the formula (73).

The formula (73)

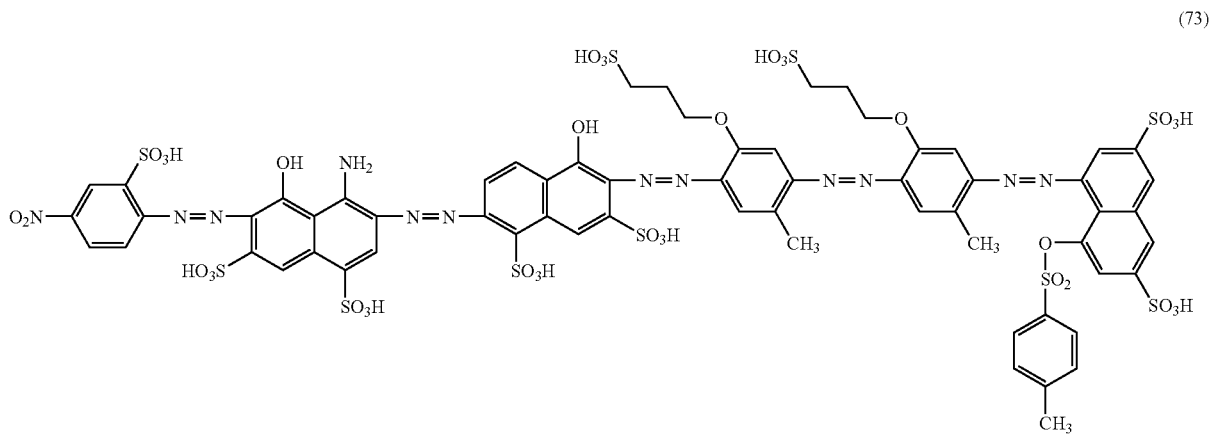

The obtained reaction solution was heated to 70° C. and reacted for 2 hours while maintaining pH 10.8 to 11.0 with sodium hydroxide. After the reaction, it was adjusted to pH 6.0 to 7.5 with 35% hydrochloric acid, and salted out by addition of sodium chloride and the precipitate was separated by filtration. The obtained wet cake was dissolved in 200 parts of water and then crystallized by addition of 250 parts of methanol, and the precipitate was separated by filtration. The obtained wet cake was dissolved in 170 parts of water and then crystallized by addition of 250 parts of methanol, and the precipitate was separated by filtration and dried to obtain 15.4 parts of a compound of the formula (74) as a sodium salt. The maximum absorption wavelength (λmax) of this compound in an aqueous solution of pH 7 to 8 was 625 nm and the solubility was 100 g/L or more.

The formula (74)

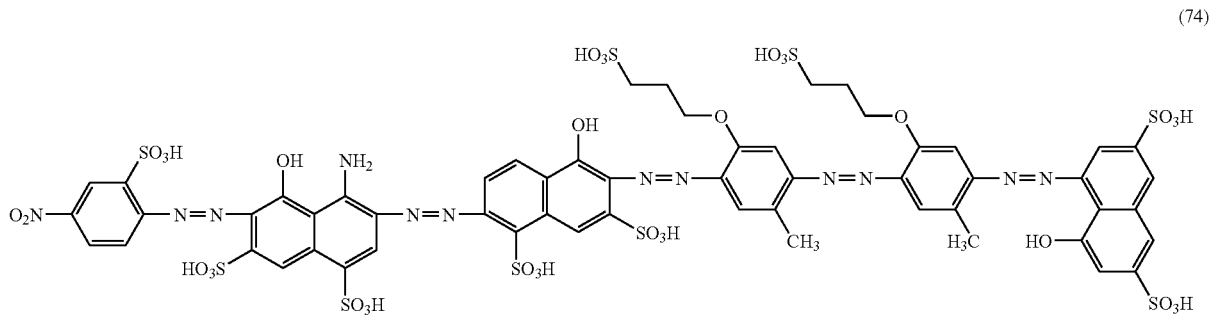

Synthesis Example 2

(1) In the same manner as in Synthesis Example 1 except that the compound of the formula (71) obtained by the method described in Patent Literature 13 was used instead of the compound of the formula (70) in (3) of Synthesis Example 1, 13.2 parts of a compound of the following formula (75) of the present invention was obtained as a sodium salt. The maximum absorption wavelength (λmax) of this compound in an aqueous solution of pH 7 to 8 was 615 nm and the solubility was 100 g/L or more.

The formula (71)

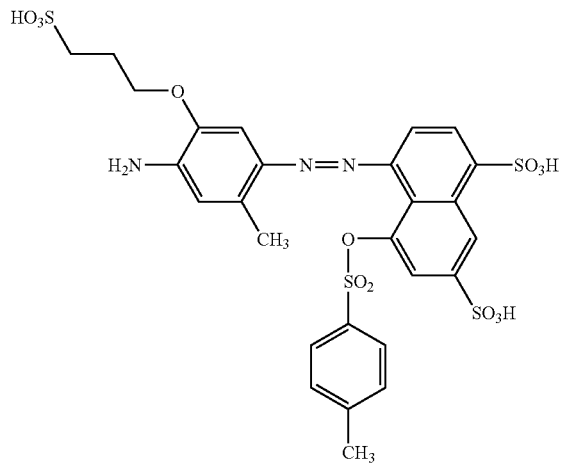

The formula (75)

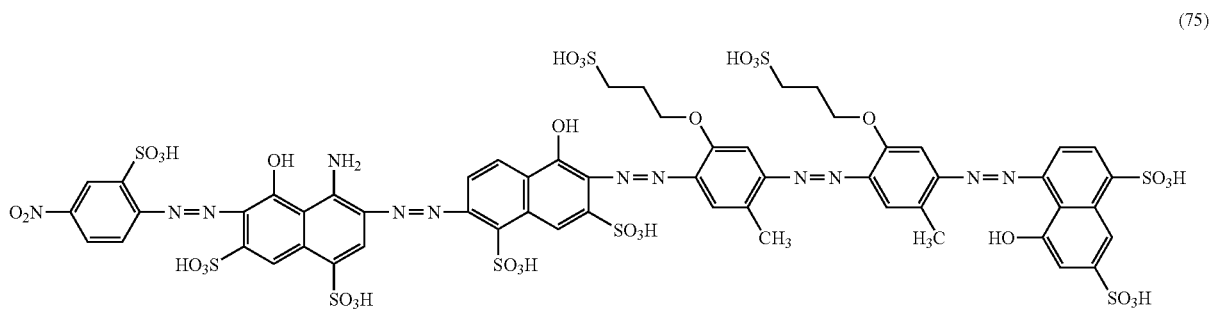

Synthesis Example 3

(1) In the same manner as in Synthesis Example 1 except that sodium 2-nitroaniline-4-sulfonate was used instead of sodium 4-nitroaniline-2-sulfonate in (2) of Synthesis Example 1, 14.3 parts of an azo compound of the formula (76) of the present invention was obtained as a sodium salt. The maximum absorption wavelength (λmax) of this compound in an aqueous solution of pH 7 to 8 was 636 nm and the solubility was 100 g/L or more.

The formula (76)

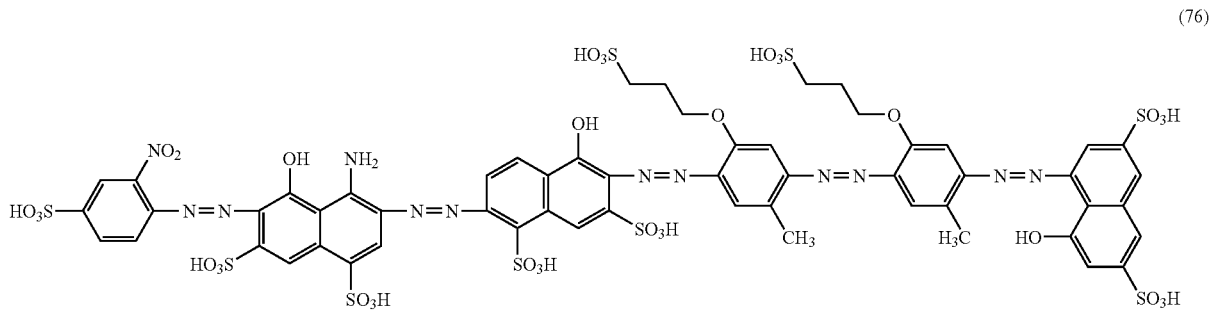

Synthesis Example 4

In 600 parts of water, 14.3 parts of a compound represented by the formula (77) was added and adjusted to pH 6.0 to 7.0 with caustic soda liquid, and 6.1 parts of cyanuric chloride was added thereto at 10 to 20° C. After the addition, it was, with the pH maintained at pH 6.0 to 7.5 with sodium carbonate, stirred for 2 hours to obtain a solution containing a compound of the formula (78).

The formula (77)

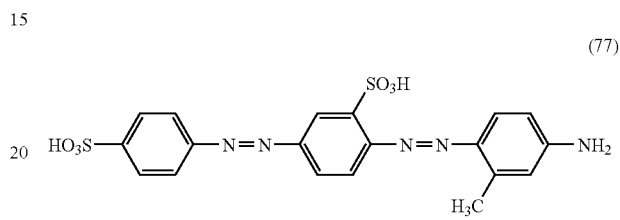

The formula (78)

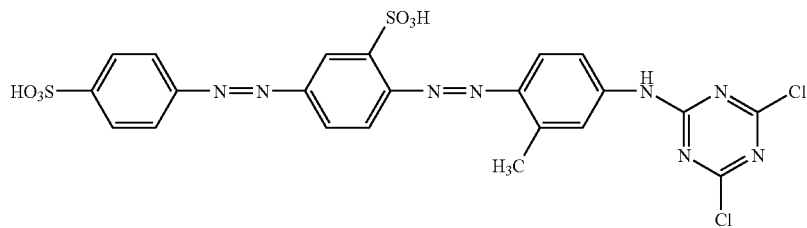

(78)

The temperature of this solution was raised to 30 to 40° C. and 17.1 parts of the compound of the formula (77) was added thereto. After the addition, it was, with the pH maintained at pH=7.0 to 8.5 with sodium carbonate, stirred for 3 hours to obtain a solution containing a compound of the formula (79).
The formula (79)

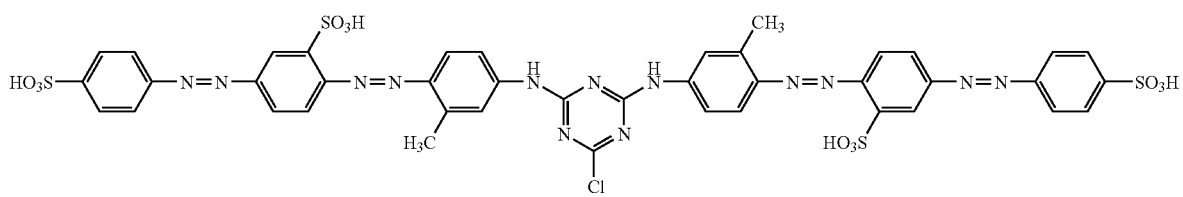

(79)

The temperature of this solution was raised to 80 to 95° C., and 5.0 parts of taurine was added thereto. After the addition, it was, with the pH maintained at pH 9.0 to 10.0 with sodium carbonate, stirred for 6 hours and salted out with sodium chloride, and the precipitate was separated by filtration. The whole volume of the obtained cake was dissolved in 300 parts of water, crystallized with 600 parts of 2-propanol for desalination, and then dried to obtain 30.1 parts of a compound of the formula (80). The maximum absorption wavelength of this compound in an aqueous solution was 415 nm.
The formula (80)

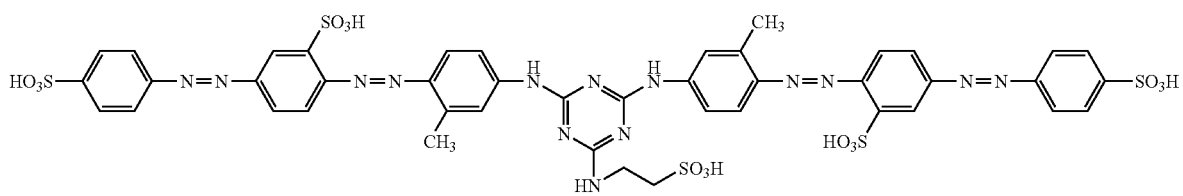

(80)

Synthesis Example 5

In the same manner as in Synthesis Example 4 except that 12.5 parts of iminodiacetic acid was used instead of 5.0 parts of taurine in Synthesis Example 4, 31.0 parts of a compound of the formula (81) was obtained. The maximum absorption wavelength of this compound in an aqueous solution was 425 nm.
The formula (81)

Synthesis Example 6

Synthesis of the Orange Dye Compound Described in Synthesis Example 1 of Patent Literature 13

In 675 parts of water, 115 parts of a compound of the formula (82), 98 parts of a compound of the formula (83), 61 parts of a 48% aqueous sodium hydroxide solution and 11 parts of ethylene glycol were added and stirred at 98° C. for 10 hours to complete the condensation reaction.

(81)

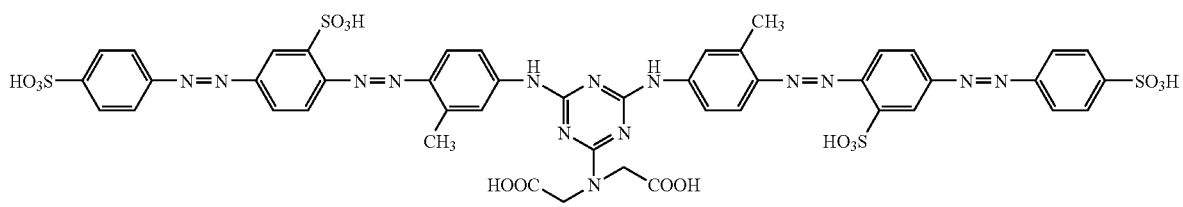

The formula (82)

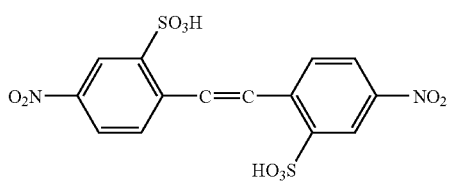

The formula (83)

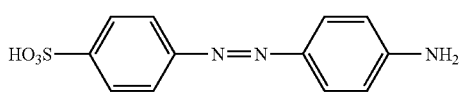

In the obtained reaction solution, 280 parts of water was added, the temperature of which was then adjusted to 85 to 88° C., 12 parts of glucose was added thereto and stirred for 2 hours to complete the reduction reaction. Next, the pH was adjusted to 9.0 to 9.5 with hydrochloric acid, the solution was salted out with sodium chloride, and the precipitate was separated by filtration. The whole volume of the obtained cake was dissolved in 2000 parts of water and crystallized by addition of 2000 parts of methanol, and the crystal was filtered and separated for desalination. Next, the obtained crystal was dried to obtain 192 parts of an orange dye compound. The maximum absorption wavelength ($\lambda$max) of this compound in an aqueous solution was 413 nm and the solubility in water was 100 g/L or more.

(A) Preparation of Ink

Hereinafter, all the dye ingredients were subjected to desalting treatment for use.

Example 3-1

A water-based black ink composition of the present invention was prepared by mixing the ingredients in the following table I-8. Next, it was filtered through a 0.45 μm membrane filter to obtain a water-based black ink composition where the foreign substances were removed.

TABLE I-8

| | |
|---|---|
| The compound (Na and Li-mixed salt) of the formula (17) obtained in Example 1-1 | 1.5 parts |
| The compound (Na salt) of the formula (74) obtained in Synthesis Example 1 | 2.25 parts |
| The compound (Na salt) of the formula (80) obtained in Synthesis Example 4 | 1.25 parts |
| Glycerine | 5.0 parts |
| Urea | 5.0 parts |
| N-methyl-2-pyrolidone | 4.0 parts |
| Isopropyl alcohol | 3.0 parts |
| Butylcarbitol | 2.0 parts |
| Surfactant (Trade name: Surfynol104, manufactured by Nissin Chemical Industry Co., Ltd.) | 0.1 part |
| Water + aqueous sodium hydroxide solution | 75.9 parts |
| Total | 100.0 parts |

Example 3-2

A water-based black ink composition of the present invention was prepared by mixing the ingredients in the following table I-9. Next, it was filtered through a 0.45 μm membrane filter to obtain a water-based black ink composition where the foreign substances were removed.

TABLE I-9

| | |
|---|---|
| The compound (Na salt) of the formula (36) obtained in Example 2-6 | 1.3 parts |
| The compound (Na salt) of the formula (74) obtained in Synthesis Example 1 | 2.35 parts |
| The compound (Na salt) of the formula (80) obtained in Synthesis Example 4 | 1.35 parts |
| Glycerine | 5.0 parts |
| Urea | 5.0 parts |
| N-methyl-2-pyrolidone | 4.0 parts |
| Isopropyl alcohol | 3.0 parts |
| Butylcarbitol | 2.0 parts |
| Surfactant (Trade name Surfynol104, manufactured by Nissin Chemical Industry Co., Ltd.) | 0.1 part |
| Water + aqueous sodium hydroxide solution | 75.9 parts |
| Total | 100.0 parts |

(B) Inkjet Printing

Using each of the water-based black ink compositions of the present invention which were obtained above, inkjet recording was performed on two kinds of paper, special glossy paper A (trade name: Professional Photopaper PR-101, manufactured by Canon Inc.) and special glossy paper B (trade name: Super Photopaper SP-101, manufactured by Canon Inc.) by an ink jet printer (trade name: PIXUS iP4100, manufactured by Canon Inc.). In printing, such an image pattern was made that several graduations of reflection density were obtained, and a black printed matter of half tone was obtained. Among the test methods described below, in measurement for hue evaluation which is an item of evaluation using a calorimeter, the part of this printed matter where the reflection density D value was the most highest was used for calorimeter of a* value and b* value of the printed matter. Similarly, in measurement for light fastness test and ozone gas fastness test using a calorimeter, measurement was conducted using the graduation part of the printed matters where the reflection density D value before the test was the nearest to 1.0. Hue evaluation was conducted on the whole printed matter by visual observation.

(C) Evaluation of Recorded Image

The recorded images with the water-based ink composition of the present invention were evaluated on hue, print density, change of hue after the light fastness test and change of hue after ozone gas fastness test. The results are shown in Table I-11 described afterward. The test method is described below.

(1) Hue Evaluation

In hue evaluation (numeric data) of the printed images, evaluation by visual observation and evaluation by a colorimeter are employed in combination. For evaluation by a colorimeter, a* value and b* value were measured using Gretag Macbeth SpectroEye (trade name, manufactured by Gretag-Macbeth AG) to calculate C* value. The formula to calculate C* value is $C^*=\{(a^*)^2+(b^*)^2\}^{1/2}$. The evaluation criteria are shown below.

○ Good black without color by visual observation, having C*<6.0 from colorimeter Δ Good black without color by visual observation, having 6.0≦C*≦10 from calorimeter × Black with color by visual observation or without color by visual observation, having 10<C* from colorimeter (2) Evaluation of Print Density Using Gretag Macbeth SpectroEye (trade name, manufactured by GretagMacbeth AG), hue density D value was measured. The evaluation criteria are shown below.

○ $2.2 \leqq D$
Δ $2.0 \leqq D < 2.2$
x $D < 2.0$ (3) Light Fastness Test

Using a xenon weatherometer (trade name: Ci4000, manufactured by ATLAS Electric Devices Co.), the printed samples were irradiated at an illuminance of 0.36 W/m² for 100 hours. After the test, calorimeter was conducted similarly above and the color difference (ΔE) before and after the test and the residual rate of the density were determined. Judgment was conducted according to the following criteria.

○ ΔE: under 15, and residual rate: 75% or more
Δ Only either of ΔE and residual rate does not satisfy the conditions of ○
x ΔE: 15 or more, and residual rate: under 75%

(4) Ozone Gas Fastness Test

Using an ozone weatherometer (manufactured by Suga Test Instruments Co., Ltd.), the printed samples were left for 4 hours at an ozone gas concentration of 12 ppm, a humidity of 60% RH and a temperature of 24° C. After the test was completed, calorimeter was conducted similarly above and the color difference (ΔE) before and after the test and the residual rate of the density were determined. Judgment was conducted according to the following criteria.

○ ΔE: under 15, and residual rate: 75% or more
Δ Only either of ΔE and residual rate does not satisfy the conditions of ○
x ΔE: 15 or more, and residual rate: under 75%

Comparative Example I-1

For comparison, the ink composition described in Example 2 of Patent Literature 13 was prepared in the composition of the following table I-10.

The evaluation results of the recorded images conducted similarly to the above (B) Inkjet Printing and (C) Evaluation of Recorded Image are shown in Table I-11.

TABLE I-10

| | |
|---|---|
| The compound of the following formula (84) | 1.2 parts |
| The compound of the following formula (85) | 2.4 parts |
| The compound obtained in Synthesis Example 20 | 1.4 parts |
| Glycerine | 5.0 parts |
| Urea | 5.0 parts |
| N-methyl-2-pyrolidone | 4.0 parts |
| Isopropyl alcohol | 3.0 parts |
| Butylcarbitol | 2.0 parts |
| Surfactant (Surfynol 104, manufactured by Nissin Chemical Industry Co., Ltd.) | 0.1 part |
| Water + aqueous lithium hydroxide solution | 75.9 parts |
| Total | 100.0 parts |

The formula (84)

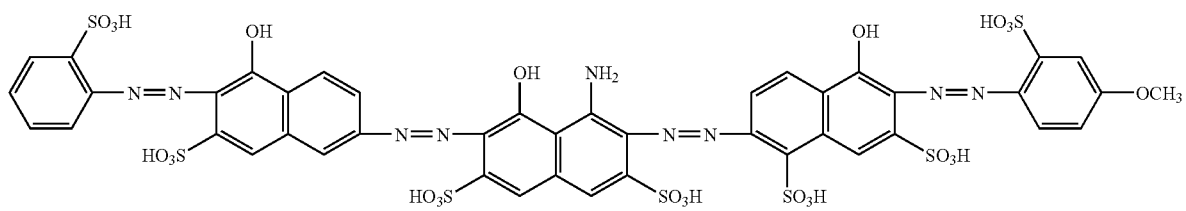

(84)

The formula (85)

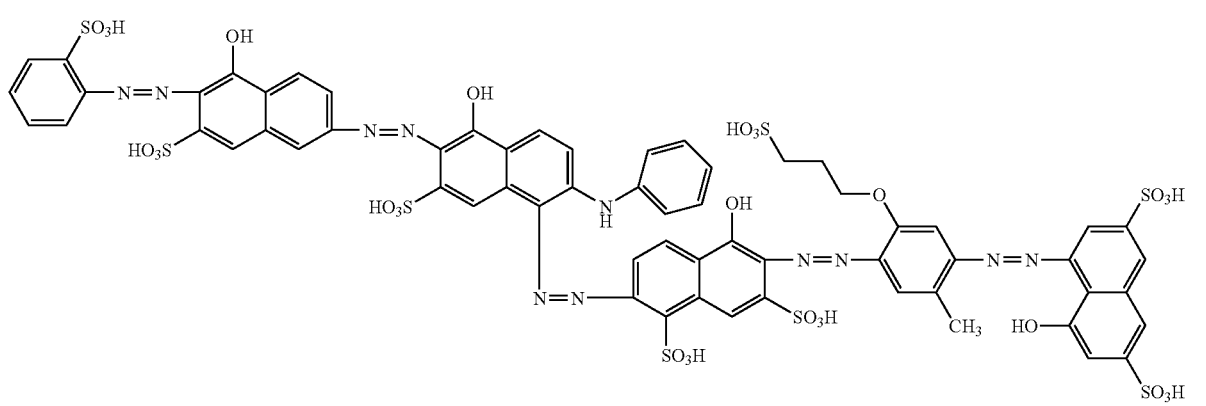

(85)

TABLE I-11

|  | Hue | Density | Light fastness | Ozone gas fastness |
|---|---|---|---|---|
| Example I-1 | | | | |
| Special glossy paper A | ○ | ○ | ○ | ○ |
| Special glossy paper B | ○ | ○ | ○ | ○ |
| Example I-2 | | | | |
| Special glossy paper A | ○ | ○ | ○ | ○ |
| Special glossy paper B | ○ | ○ | ○ | ○ |
| Comparative Example I-1 | | | | |
| Special glossy paper A | ○ | ○ | x | x |
| Special glossy paper B | ○ | ○ | x | x |

As is clear from Table I-11, even when any of special glossy paper A and B was used, the recorded images using the ink composition of Comparative Example I-1 had a color difference before and after the test of 15 or more and a color residual rate of under 75% judgment x) in light fastness, and also had a color difference of 15 or more and a color residual rate of under 75% (judgment x) similarly in ozone gas fastness.

In comparison with this, it is found that the recorded images using the ink composition of the present invention had very good hue and print density, a color difference before and after the test of under 15 and a color residual rate of 75% or more (judgment ○) in light fastness, and also had a color difference of under 15 and a color residual rate of 75% or more judgment ○) similarly in ozone gas fastness, showing remarkably excellent light fastness and ozone gas fastness. The ink composition of the present invention is thus extremely useful as a black ink composition.

Synthesis Example 7

(1) 6.4 parts of 2-amino-5-naphthole-1,7-disulfonic acid and 4.1 parts of p-toluenesulfonyl chloride were reacted at pH 8.0 to 8.5 and 70° C. for 1 hour and then salted out under acidic condition, and the precipitate was separated by filtration to obtain a compound of the formula (II-49). In 90 parts of water, 8.8 parts of said compound was added and dissolved while adjusting to pH 6.0 to 8.0 with sodium carbonate. In said solution, 6.8 parts of 35% hydrochloric acid was added, the temperature of which was then cooled to 0 to 5° C., and 3.6 parts of a 40% aqueous sodium nitrite solution was added thereto for diazotization.

The formula (II-49)

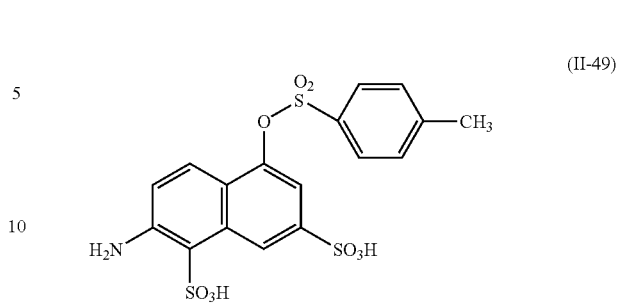

In this diazo suspension, a liquid where 5.8 parts of 4-amino-5-hydroxynaphthalene-1,7-disulfonic acid was suspended in 60 parts of water was added and then stirred at a solution temperature of 10 to 20° C. for 4 hours while maintaining the pH value of the solution at 2.4 to 2.8 with sodium carbonate. Next, it was, with the pH value adjusted to 7.0 to 8.5 with sodium carbonate, dissolved to obtain a solution containing a monoazo compound of the formula (II-50).

The formula (II-50)

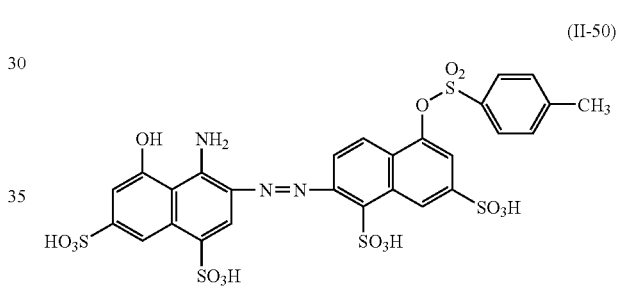

(2) In 50 parts of water, 5.2 parts of sodium 4-nitroaniline-2-sulfonate was dissolved, and 6.4 parts of 35% hydrochloric acid and 4.0 parts of 40% aqueous sodium nitrite solution were added hereto at 0 to 5° C. for diazotization. This diazo suspension was added dropwise in the solution containing the monoazo compound of the formula (II-50) obtained in the above reaction at 10 to 20° C., while maintaining the pH value of the solution at 8.0 to 9.0 with sodium carbonate. After completion of the dropwise addition, it was stirred at 15 to 30° C. for 2 hours at pH 8.0 to 9.0 to obtain a solution containing a disazo compound of the formula (II-51).

The formula (II-51)

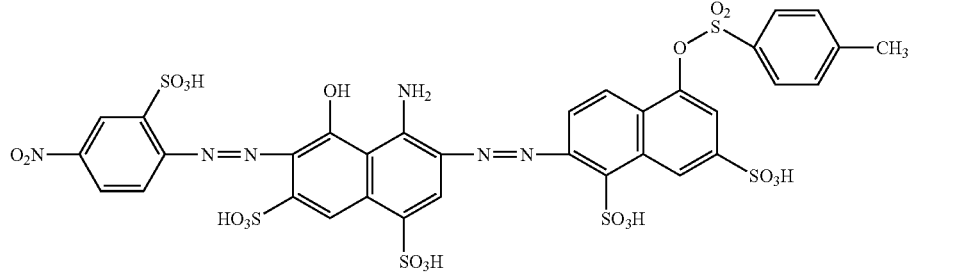

The above obtained solution was heated to 70° C. and then stirred for 1.5 hours while maintaining the pH value at 10.5 to 11.0 with sodium hydroxide. It was cooled to room temperature and, at pH 7.0 to 8.0 adjusted with 35% hydrochloric acid, salted out by addition of sodium chloride and the precipitate was separated by filtration to obtain a wet cake containing a compound of the formula (II-52).

The formula (II-52)

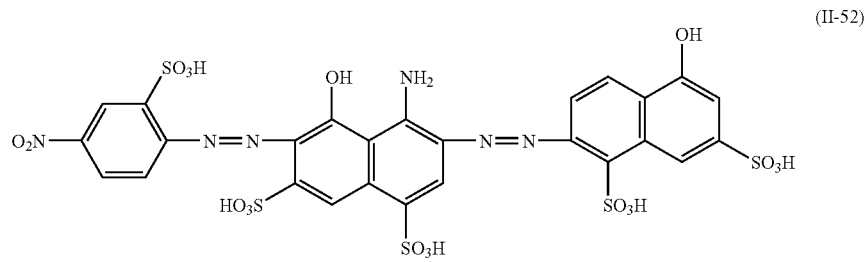

(3) In 80 parts of water, 7.5 parts of the compound of the formula (II-49) was added and then dissolved while adjusting to pH 6.0 to 8.0 with sodium carbonate. Thereto, 5.8 parts of 35% hydrochloric acid was added, the temperature of which was then cooled to 0 to 5° C., and 2.9 parts of a 40% aqueous sodium nitrite solution was added thereto for diazotization. This diazo suspension was added dropwise in a solution where the wet cake containing the compound of the formula (II-52) was dissolved in 150 parts of water, while maintaining said solution temperature at 15 to 30° C. and the pH value of said solution at 8.0 to 9.0 with sodium carbonate. After completion of the dropwise addition, the obtained solution was stirred at pH 8.0 to 9.0 and a temperature of said solution of 15 to 30° C. for 2 hours to obtain a solution containing a trisazo compound of the formula (II-53).

The formula (II-53)

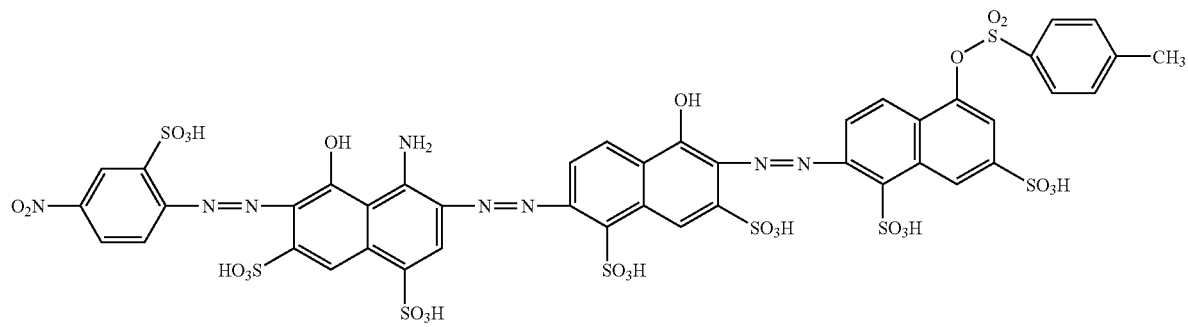

The above obtained solution was heated to 70° C. and then stirred for 1.5 hours while maintaining the pH value at 10.5 to 11.0 with sodium hydroxide. It was cooled to room temperature and then, at pH 7.0 to 8.0 adjusted with 35% hydrochloric acid, salted out by addition of sodium chloride, and the precipitate was separated by filtration to obtain a wet cake containing a compound of the formula (II-54).

The formula (II-54)

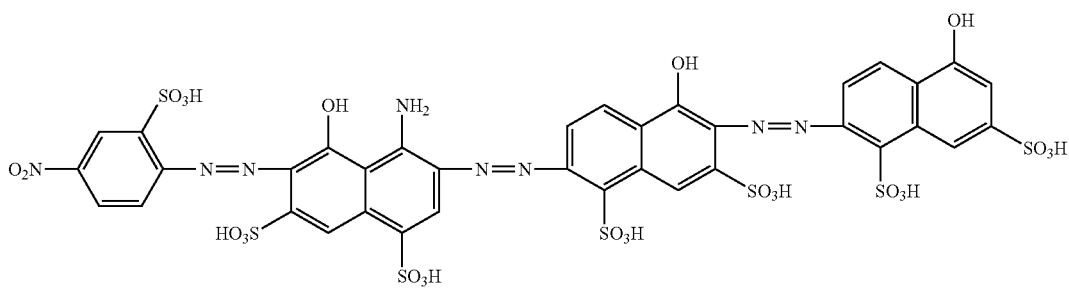

(4) In 55 parts of water, 5.3 parts of a compound of the following formula (II-55) was dissolved at pH 6.0 to 7.0 adjusted with sodium hydroxide, and 4.9 parts of 35% hydrochloric acid and 2.7 parts of a 40% aqueous sodium nitrite solution were added hereto at 0 to 5° C. for diazotization. This diazo suspension was added dropwise in a solution where the wet cake containing the compound of the formula (II-54) obtained in the above reaction was dissolved in 260 parts of water, while maintaining said solution temperature at 15 to 30° C. and the pH value of said solution at 8.0 to 9.0. The maintaining of said pH value was conducted with sodium carbonate. After completion of the dropwise addition, it was stirred at 15 to 30° C. for 2 hours while maintaining pH 8.0 to 9.0 and salted out by addition of lithium chloride and the precipitate was separated by filtration. The obtained wet cake was dissolved in 110 parts of water and crystallized by addition of 250 parts of 2-propanol and fractionated by filtration. Further, the obtained wet cake was dissolved in 100 parts of water and then crystallized by addition of 250 parts of 2-propanol, and the precipitate was separated by filtration and dried to obtain 17.0 parts of an azo compound of the formula (II-56) (Compound No. 2-1 in Table II-3) as a mixed salt of lithium and sodium. The maximum absorption wavelength ($\lambda$max) of this compound in an aqueous solution of pH 9 was 572 nm and the solubility in water was 100 g/L or more.

The formula (II-55)

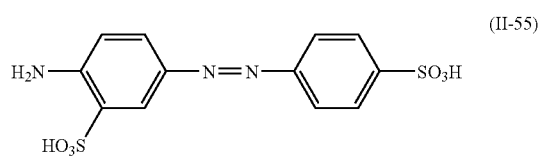

The formula (II-56)

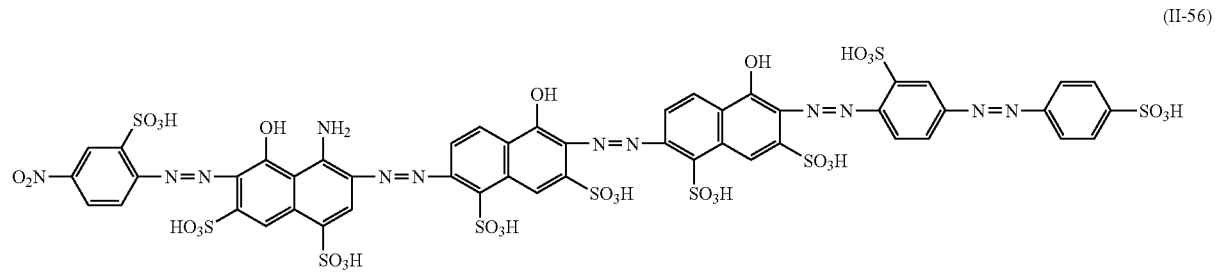

Synthesis Example 8

In the same manner as in Synthesis Example 7 except that 5.2 parts of sodium 2-nitroaniline-4-sulfonate was used instead of 5.2 parts of sodium 4-nitroaniline-2-sulfonate in (2) of Synthesis Example 7, 17.0 parts of an azo compound of the formula (II-57) (Compound No. 2-2 in Table II-3) was obtained as a mixed salt of lithium and sodium. The maximum absorption wavelength ($\lambda$max) of this compound in an aqueous solution of pH 9 was 571 nm and the solubility in water was 100 g/L or more.

The formula (II-57)

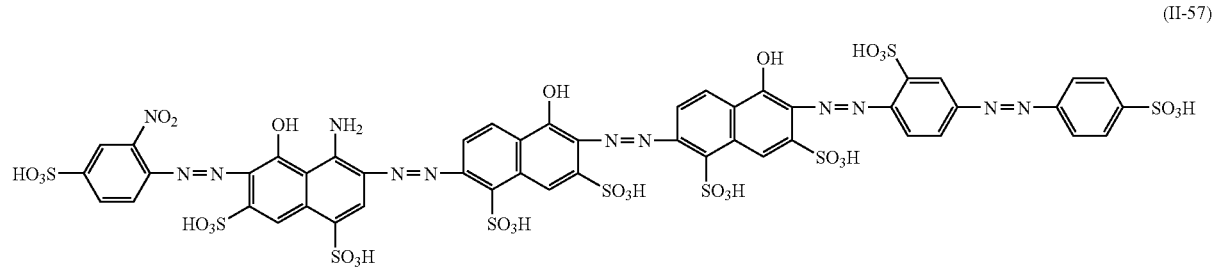

Synthesis Example 9

In 55 parts of water, 10.8 parts of a compound of the following formula (II-58) obtained by the method described in JP 2005-068416 was added and then dissolved at pH 6.0 to 7.0 adjusted with sodium hydroxide, and 4.9 parts of 35% hydrochloric acid and 2.7 parts of a 40% aqueous sodium nitrite solution was added hereto at 0 to 5° C. for diazotization to obtain a diazo suspension. Separately, a wet cake containing the above compound of the formula (II-54) obtained from the reaction in (3) of Synthesis Example 7 was dissolved in 260 parts of water. In said solution, the above obtained diazo suspension was added dropwise, while maintaining the solution temperature at 15 to 30° C. and the pH value of the solution at 8.0 to 9.0. The maintaining of the pH was conducted with sodium carbonate. After completion of the dropwise addition, it was stirred at a solution temperature of 15 to 30° C. and pH 8.0 to 9.0 for 2 hours. Further, said solution was heated to 70° C. and then stirred for 1.5 hours while maintaining the pH value at 10.5 to 11.0 with sodium hydroxide.

It was cooled to room temperature and then, at pH 7.0 to 8.0 adjusted with 35% hydrochloric acid, salted out by addition of lithium chloride and the precipitate was separated by filtration.

The obtained wet cake was dissolved in 450 parts of water and crystallized by addition of 800 parts of 2-propanol and the precipitate was separated by filtration. Furthermore, the obtained wet cake was dissolved in 450 parts of water and then crystallized by addition of 800 parts of 2-propanol and the precipitate was separated by filtration and dried to obtain 10.0 parts of an azo compound of the formula (II-59) (Compound No. 2-13 in Table II-5) was obtained as a mixed salt of lithium and sodium. The maximum absorption wavelength (λmax) of this compound in an aqueous solution of pH 9 was 623 nm and the solubility in water was 100 g/L or more.

The formula (II-58)

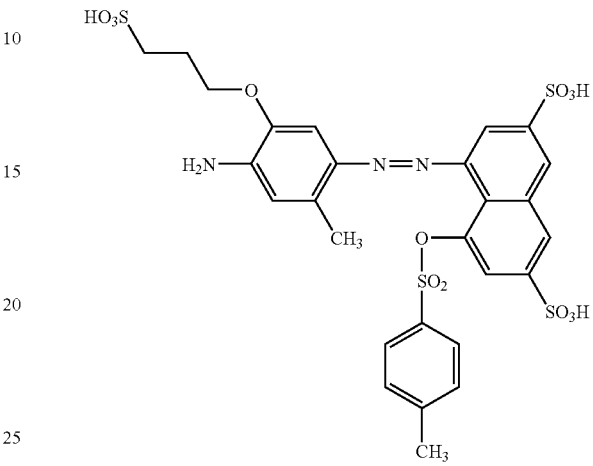

The formula (II-59)

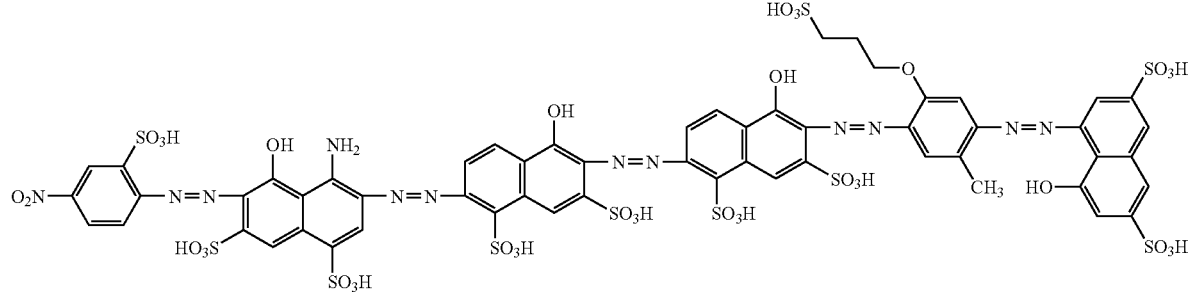

Synthesis Example 10

In the same manner as in Synthesis Example 7 except that 6.5 parts of a compound of the following formula (II-60) was used instead of 5.3 parts of the compound of (II-55) in (4) of Synthesis Example 7, 11.0 parts of an azo compound of the formula (II-61) (Compound No. 2-5 in Table II-3) was obtained as a mixed salt of lithium and sodium. The maximum absorption wavelength (λmax) of this compound in an aqueous solution of pH 9 was 612 nm and the solubility in water was 100 g/L or more.

Meanwhile, the compound of (II-60) can be obtained by, for example, the following method. That is, in 100 parts of water, 18.1 parts of 5-aminoisophthalic acid was dissolved at pH 6.0 to 7.0 adjusted with sodium hydroxide, 36.5 parts of 35% hydrochloric acid and 18.1 parts of a 40% aqueous sodium nitrite solution were added hereto at 0 to 5° C. for diazotization. This diazo suspension was added dropwise in a solution where 24.5 parts of the compound (II-62) described in JP 2005-068416 was dissolved in 150 parts of water at 5 to 10° C. while maintaining the pH value of the solution at 5.0 to 6.0 with sodium carbonate. After completion of the dropwise addition, it was stirred at 10 to 20° C. for 2 hours at pH 8.0 to 9.0 and then salted out by addition of sodium chloride and the precipitate was separated by filtration to obtain a wet cake containing a compound of the formula (II-60).

The formula (II-60)

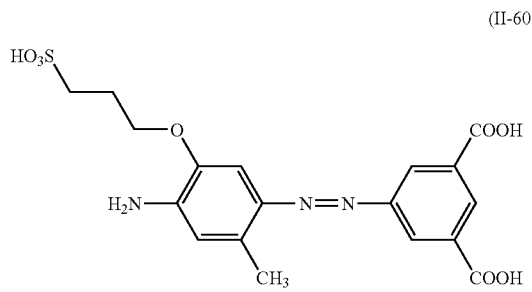

The formula (II-61)

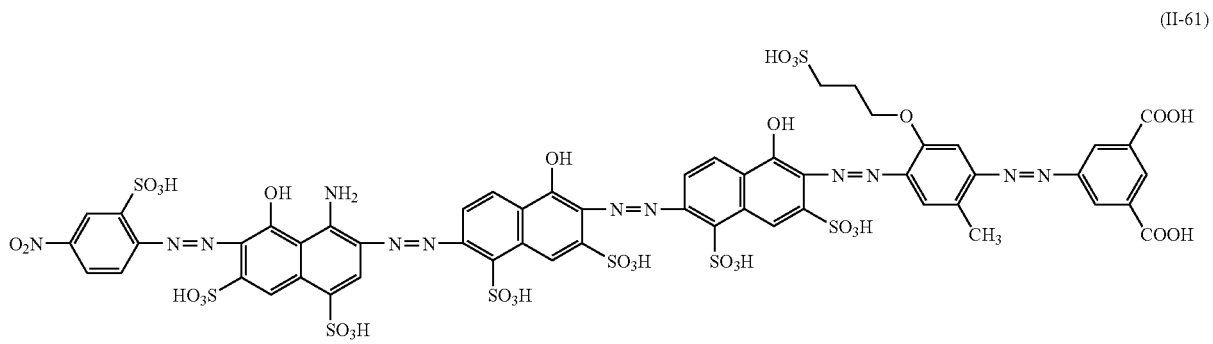

The formula (II-62)

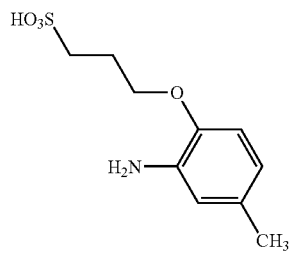

Synthesis Example 11

In the same manner as in Synthesis Example 6 except that 132 parts of a compound of the following formula (II-70) was used instead of the above compound of the formula (83) to obtain 230 parts of an orange compound. The maximum absorption wavelength (λmax) of this compound in an aqueous solution was 437 nm and the solubility in water was 100 g/L or more.

The formula (II-70)

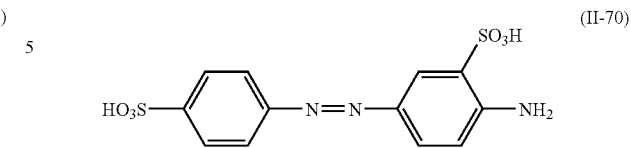

Synthesis Example 12

Synthesis of C.I. Direct Orange 62

In 675 parts of water, 115 parts of the above compound of the formula (82), 172 parts of a compound of the following formula (II-71), 61 parts of a 48% aqueous sodium hydroxide solution and 11 parts of ethylene glycol were added and stirred at 98° C. for 7 hours to complete the condensation reaction.

The formula (II-71)

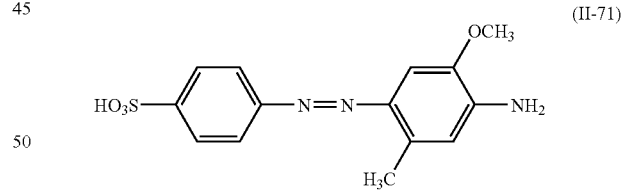

The obtained reaction solution was, with the pH adjusted to 9.0 to 9.5 with hydrochloric acid, salted out with sodium chloride and the precipitate was separated by filtration. The whole volume of the obtained cake was dissolved in 2000 parts of water and crystallized by addition of 2000 parts of methanol and the crystal was filtered and separated for desalination. Next, the obtained crystal was dried to obtain 214 parts of an orange dye compound (C.I. Direct Orange 62). The maximum absorption wavelength (λmax) of this compound in an aqueous solution was 494 nm and the solubility in water was 100 g/L or more.

(A) Preparation of Ink

Hereinafter, all the dye ingredients were subjected to desalting treatment for use.

Example 4-1

A water-based black ink composition of the present invention was prepared by mixing the ingredients in the following table II-9. Next, it was filtered through a 0.45 μm membrane filter to obtain a water-based black ink composition where the foreign substances were removed.

TABLE II-9

| | |
|---|---|
| The compound (Na salt) of the formula (17) obtained in Example 1-1 | 1.75 parts |
| The compound (Na salt) of the formula (II-59) obtained in Synthesis Example 9 | 1.75 parts |
| The compound (Na salt) of the formula (80) obtained in Synthesis Example 4 | 1.5 parts |
| Glycerine | 5.0 parts |
| Urea | 5.0 parts |
| N-methyl-2-pyrolidone | 4.0 parts |
| Isopropyl alcohol | 3.0 parts |
| Butylcarbitol | 2.0 parts |
| Surfactant (Trade name: Surfynol105, manufactured by Nissin Chemical Industry Co., Ltd.) | 0.1 part |
| Water + aqueous sodium hydroxide solution | 75.9 parts |
| Total | 100.0 parts |

Example 4-2

A water-based black ink composition of the present invention was prepared by mixing the ingredients in the following table II-10. Next, it was filtered through a 0.45 μm membrane filter to obtain a water-based black ink composition where the foreign substances were removed.

TABLE II-10

| | |
|---|---|
| The compound (Na salt) of the formula (17) obtained in Example 1-1 | 1.75 parts |
| The compound (Na salt) of the formula (II-59) obtained in Synthesis Example 9 | 1.75 parts |
| The compound (Na salt) of the formula (80) obtained in Synthesis Example 4 | 1.0 part |
| The compound (Na salt) obtained in Synthesis Example 6 | 0.5 parts |
| Glycerine | 5.0 parts |
| Urea | 5.0 parts |
| N-methyl-2-pyrolidone | 4.0 parts |
| Isopropyl alcohol | 3.0 parts |
| Butylcarbitol | 2.0 parts |
| Surfactant (Trade name: Surfynol105, manufactured by Nissin Chemical Industry Co., Ltd.) | 0.1 part |
| Water + aqueous sodium hydroxide solution | 75.9 parts |
| Total | 100.0 parts |

Example 4-3

A water-based black ink composition was prepared by mixing the ingredients in the following table II-11. Next, it was filtered through a 0.45 μm membrane filter to obtain a water-based black ink composition where the foreign substances were removed.

TABLE II-11

| | |
|---|---|
| The compound (Na salt) of the formula (19) obtained in Example 1-2 | 1.9 parts |
| The compound (Na salt) of the formula (II-59) obtained in Synthesis Example 9 | 1.65 parts |
| The compound (Na salt) of the formula (80) obtained in Synthesis Example 4 | 1.45 parts |
| Glycerine | 5.0 parts |
| Urea | 5.0 parts |
| N-methyl-2-pyrolidone | 4.0 parts |
| Isopropyl alcohol | 3.0 parts |
| Butylcarbitol | 2.0 parts |
| Surfactant (Trade name: Surfynol105 manufactured by Nissin Chemical Industry Co., Ltd.) | 0.1 part |
| Water + aqueous sodium hydroxide solution | 75.9 parts |
| Total | 100.0 parts |

(B) Inkjet Printing

Using each of the water-based black ink compositions of the present invention which were obtained above, inkjet recording was performed on two kinds of paper, special glossy paper A (trade name: Professional Photopaper PR-101, manufactured by Canon Inc.) and special glossy paper B (trade name: Super Photopaper SP-101, manufactured by Canon Inc.) by an ink jet printer (trade name: PIXUS iP4100, manufactured by Canon Inc.). In printing, such an image pattern was made that several graduations of reflection density were obtained, and a black printed matter of half tone was obtained. Among the test methods described below, in measurement for hue evaluation which is an item of evaluation using a colorimeter, the part of this printed matter where the reflection density D value was the most highest was used for calorimeter of a* value and b* value of the printed matter. Similarly, in measurement for light fastness test and ozone gas fastness test using a calorimeter, the measurement was conducted using the graduation part of the printed matters where the reflection density D value before the test was the nearest to 1.0. Hue evaluation was conducted on the whole printed matter by visual observation.

(C) Evaluation of Recorded Image

The recorded images with the water-based ink composition of the present invention were evaluated on hue, print density, change of hue after the light fastness test and change of hue after ozone gas fastness test. The results are shown in Table 24. The test method is described below.

(1) Hue Evaluation

In hue evaluation (numeric data) of the printed images, evaluation by visual observation and evaluation by a colorimetry are employed in combination. For evaluation by a colorimetry, a* value and b* value were measured using Gretag Macbeth SpectroEye (trade name, manufactured by Gretag-Macbeth AG) to calculate C* value. The formula to calculate C* value is $C^*=\{(a^*)^2+(b^*)^2\}^{1/2}$. The evaluation criteria are shown below.

○ Good black without color by visual observation, having C*<6.0 from colorimetry Δ Good black without color by visual observation, having 6.0≦C*≦10 from colorimetry x Black with color by visual observation or without color by visual observation, having 10<C* from colorimetry (2) Evaluation of Print Density Using Gretag Macbeth SpectroEye (trade name, manufactured by GretagMacbeth AG), the hue density D value was measured. The evaluation criteria are shown below.

○ 2.2≦D

Δ 2.0≦D<2.2 x D<2.0

(3) Light Fastness Test

Using xenon weatherometer Ci4000 (trade name, manufacture by ATLAS Electric Devices Co.), the printed samples were irradiated at an illuminance of 0.36 W/m² for 100 hours. After the test was completed, colorimeter was conducted similarly above and the color difference (ΔE) before and after the test and the residual rate of the density were determined. Judgment was conducted according to the following criteria.

○ ΔE: under 15, and residual rate: 75% or more
Δ Only either of ΔE and residual rate does not satisfy the conditions of ○
× ΔE: 15 or more, and residual rate: under 75%

(4) Ozone Gas Fastness Test

Using Ozone Weatherometer (trade name, manufactured by Suga Test Instruments Co., Ltd.), the printed samples were left for 4 hours at an ozone concentration of 12 ppm, a humidity of 60% RH and a temperature of 24° C. After the test was completed, calorimeter was conducted similarly above and the color difference (ΔE) before and after the test and the residual rate of the density were determined. Judgment was conducted according to the following criteria.

○ ΔE: under 15, and residual rate: 75% or more
Δ Only either of ΔE and residual rate does not satisfy the conditions of 0
× ΔE: 15 or more, and residual rate: under 75%

Comparative Example II-1

For comparison, the ink composition (Table II-12) described in Example 2 of JP 2005-68416 was prepared. The evaluation results of the recorded images conducted similarly to the above (B) Inkjet Printing and (C) Evaluation of Recorded Image are shown in Table II-13.

TABLE II-12

| | |
|---|---|
| The compound of the following formula (72) | 1.2 parts |
| The compound of the following formula (73) | 2.4 parts |
| The compound obtained in Synthesis Example 6 | 1.4 parts |
| Glycerine | 5.0 parts |
| Urea | 5.0 parts |
| N-methyl-2-pyrolidone | 4.0 parts |
| Isopropyl alcohol | 3.0 parts |
| Butylcarbitol | 2.0 parts |
| Surfactant | 0.1 part |
| (Trade name: Surfynol105 manufactured by Nissin Chemical Industry Co., Ltd.) | |
| Water + aqueous lithium hydroxide solution | 75.9 parts |
| Total | 100.0 parts |

The formula (II-72)

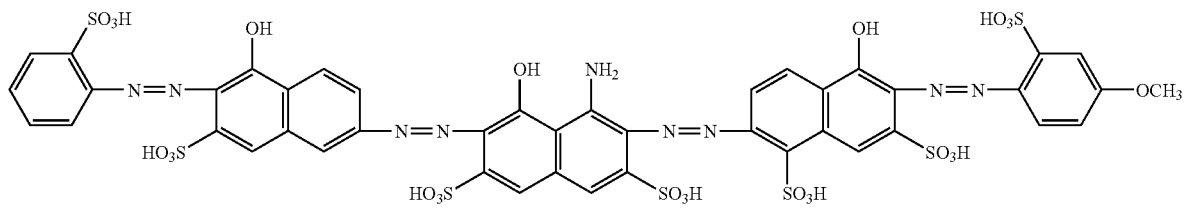

(II-72)

The formula (II-73)

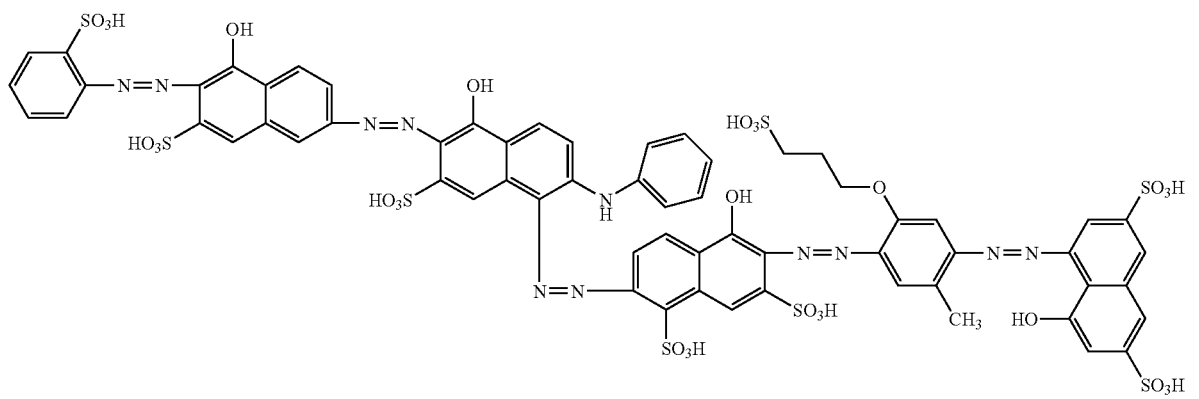

(II-73)

TABLE II-13

|  | Hue | Print density | Light fastness | Ozone gas fastness |
|---|---|---|---|---|
| Example II-1 |  |  |  |  |
| Special glossy paper A | ○ | ○ | ○ | ○ |
| Special glossy paper B | ○ | ○ | ○ | ○ |
| Example II-2 |  |  |  |  |
| Special glossy paper A | ○ | ○ | ○ | ○ |
| Special glossy paper B | ○ | ○ | ○ | ○ |
| Example II-3 |  |  |  |  |
| Special glossy paper A | ○ | ○ | ○ | ○ |
| Special glossy paper B | ○ | ○ | ○ | ○ |
| Comparative Example II-1 |  |  |  |  |
| Special glossy paper A | ○ | ○ | x | x |
| Special glossy paper B | ○ | ○ | x | x |

As is clear from Table II-13, even when any of special glossy paper A and B was used, the recoded images using the ink composition of Comparative Example II-1 had a color difference before and after the test of 15 and more and a color residual rate of under 75% (judgment x) in light fastness, and also had a color difference of 15 or more and a color residual rate of under 75% (judgment x) similarly in ozone gas fastness.

In comparison with this, it is found that the recorded images of Examples II-1 to II-3 using the ink composition of the present invention had very good hue and print density, a color difference before and after the test of under 15 and a color residual rate of 75% or more (judgment ○) in light fastness, and also had a color difference of under 15 and a color residual rate of 75% or more (judgment ○) similarly in ozone gas fastness, showing remarkably excellent light fastness and ozone gas fastness. The ink composition of the present invention is thus extremely useful as a black ink composition.

INDUSTRIAL APPLICABILITY

The ink composition containing the trisazo compound of the present invention is suitably used as a black ink liquid for inkjet recording and for writing tools.

The invention claimed is:

1. A trisazo compound represented by the following formula (1) in free acid form:

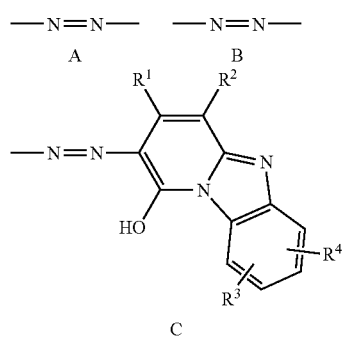

(1)

wherein, the group A is a substituted phenyl group and has a substituent selected from the group consisting of a carboxy group, a sulfo group, a chlorine atom, a cyano group, a nitro group, a sulfamoyl group, a C1 to C4 alkyl group, a C1 to C4 alkoxy group which may be substituted by a hydroxy group, a C1 to C4 alkoxy group, a sulfo group or a carboxy group and a C1 to C4 alkylsulfonyl group which may be substituted by a hydroxy group, a sulfo group or a carboxy group;

B and C are substituted para-phenylene groups and have a substituent selected from the group consisting of a carboxy group, a sulfo group, a C1 to C4 alkyl group and a C1 to C4 alkoxy group which may be substituted by a hydroxy group, a C1 to C4 alkoxy group, a sulfo group or a carboxy group;

$R^1$ represents a C1 to C4 alkyl group which may be substituted by a carboxy group, a phenyl group which may be substituted by a sulfo group, or a carboxy group;

$R^2$ represents a cyano group, a carbamoyl group or a carboxy group;

each of $R^3$ and $R^4$ independently represents a hydrogen atom, a methyl group, a chlorine atom or a sulfo group, respectively;

or a salt thereof.

2. The trisazo compound or the salt thereof according to claim 1, wherein the substituent of the group A is a sulfo group or a carboxy group and at least one of the substituents on the group B and the group C is a sulfo group or a sulfopropoxy group.

3. The trisazo compound according to claim 1, wherein the group B and the group C in the formula (1) are groups represented by the following formula (2):

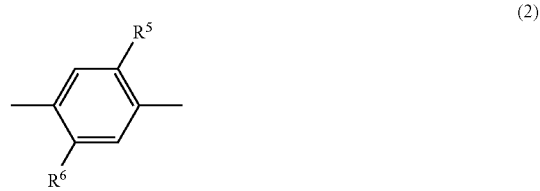

(2)

wherein, $R^5$ represents a sulfo group or a sulfopropoxy group, and $R^6$ represents a hydrogen atom, a methyl group, an ethyl group, a methoxy group or an ethoxy group, respectively.

4. The trisazo compound according to claim 3, wherein in the formula (1), $R^1$ is a methyl group, $R^2$ is a cyano group or a carbamoyl group, $R^3$ is a hydrogen atom, and $R^4$ is a sulfo group.

5. The trisazo compound or the salt thereof according to claim 3, wherein in the formula (1), the substituent of the group A is a sulfo group or a carboxy group, $R^1$ is a methyl group, $R^2$ is a cyano group or a carbamoyl group, $R^3$ is a hydrogen atom, $R^4$ is a sulfo group, the group B and the group C are represented by the above formula (2), $R^5$ is a sulfo group or a sulfopropoxy group, and $R^6$ is a hydrogen atom or a methyl group.

6. The trisazo compound or the salt thereof according to claim 3, wherein, in the formula (1), the substituent of the group A is a sulfo group and its substitution position is the para-position to the azo group, $R^1$ is a methyl group, $R^2$ is a cyano group or a carbamoyl group, $R^3$ is a hydrogen atom, $R^4$ is a sulfo group, and the group B and the group C are represented by the above formula (2) where in the group B, $R^5$ is a sulfo group and $R^6$ is a hydrogen atom, and in the group C, $R^5$ is a sulfopropoxy group and $R^6$ is a methyl group.

7. An ink composition comprising at least one kind of the trisazo compound according to claim 1.

8. A method for inkjet print recording, comprising discharging the ink composition according to claim 7 on a record-receiving material.

9. The method for inkjet print recording according to claim 8, wherein the record-receiving material is a communication sheet.

10. The method for inkjet print recording according to claim 9, wherein the communication sheet is a sheet containing a porous white inorganic substance.

11. An ink jet printer comprising a container containing the ink composition according to claim 7.

12. A colored article colored with the trisazo compound according to claim 1.

13. The trisazo compound according to claim 1, wherein in the formula (1), at least either one of the group B and the group C is a para-phenylene group substituted by a sulfo C1 to C4 alkoxy group wherein said phenylene group may be further substituted by a C1 to C4 alkyl group.

14. The trisazo compound according to claim 13, wherein in the formula (1), at least either one of the group B and the group C is a 2-sulfo C1 to C4 alkoxy-5-C1 to C4 alkyl-1,4-phenylene group.

15. The trisazo compound according to claim 1 or 13, wherein, in the formula (1), the group A is a phenyl group which has a sulfo group, a sulfo C1 to C4 alkoxy group or a sulfo C1 to C4 alkylsulfonyl group as one substituent and further may be substituted by a sulfo group, a carboxy group, a C1 to C4 alkoxy group or a nitro group, or a dicarboxy-substituted phenyl group.

16. The trisazo compound according to claim 15, wherein in the formula (1), $R^1$ is a C1 to C4 alkyl group which may be substituted by a carboxy group, or a phenyl group, $R^2$ is a cyano group, a carbamoyl group or a carboxy group, and one of $R^3$ and $R^4$ is a hydrogen atom and the other is a sulfo group.

17. The trisazo compound according to claim 1 or 13, wherein the formula (1), the group A is a 4-sulfophenyl group, a 2-carboxy-4-sulfophenyl group, a 2,4- or 2,5-disulfophenyl group, a 4-sulfo C1 to C4 alkoxyphenyl group, a 2-sulfo-4-(nitro or C1 to C4 alkoxy)phenyl group or a 3,5-dicarboxyphenyl group.

18. The trisazo compound according to claim 17, wherein in the formula (1), both the group B and the group C are 3-sulfo C1 to C4 alkoxy-6-C1 to C4 alkyl-1,4-phenylene groups, $R^1$ is a C1 to C4 alkyl group which may be substituted by a carboxy group, $R^2$ is a cyano group, and one of $R^3$ and $R^4$ is a hydrogen atom and the other is a sulfo group.

19. The trisazo compound according to claim 1, wherein in the formula (1), the group A is a 2,4-disulfophenyl group, both the group B and the group C are 2-(3-sulfopropoxy)-5-methyl-1,4-phenylene groups, $R^1$ is a methyl group, $R^2$ is a cyano group, one of $R^3$ and $R^4$ is a hydrogen atom and the other is a sulfo group.

20. A water-based black ink composition which contains the three of (a) the trisazo compound according to claim 1, (b) a dye having a maximum absorption wavelength in the range of 350 nm to 550 nm and (c) a dye having a maximum absorption wavelength in the range of 560 nm to 660 nm.

21. The water-based black ink composition according to claim 20, wherein (b) a dye having a maximum absorption wavelength in the range of 350 nm to 550 nm is the following formula (5):

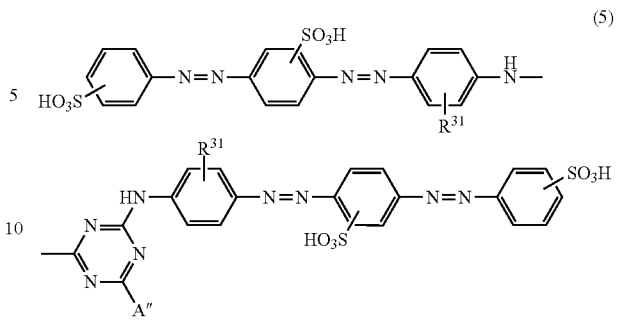

wherein, $R^{31}$ represents a hydrogen atom; a hydroxy group; a carboxy group; a C1 to C4 alkyl group which may be substituted by a hydroxy group or a C1 to C4 alkoxy group; a C1 to C4 alkoxy group which may be substituted by a hydroxy group or a C1 to C4 alkoxy group; a C1 to C4 alkylamino group which may be substituted by a hydroxy group or a C1 to C4 alkoxy group; a carboxy C1 to C5 alkylamino group; a bis[carboxy C1 to C5 alkyl]amino group; and a C1 to C4 alkanoylamino group which may be substituted by a hydroxy group or a C1 to C4 alkoxy group; a phenylamino group which may be substituted by a carboxy group, a sulfonic acid group or an amino group; a sulfo group; a halogen atom or a ureide group, and the group A″ represents a substituted alkylamino group wherein the substituent on said alkyl group is a carboxy group or a sulfo group, respectively.

22. The water-based black ink composition according to claim 20, wherein (c) a dye having a maximum absorption wavelength in the range of 560 nm to 660 nm is a compound represented by the following formula (I-2) or a salt thereof, Formula (I-2):

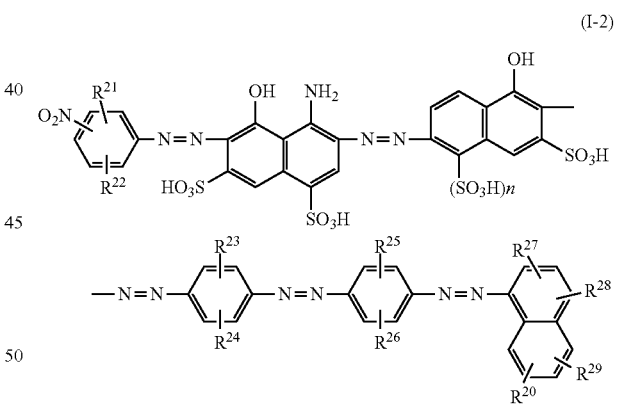

wherein, each of $R^{21}$ and $R^{22}$ independently represents a hydrogen atom, a halogen atom, a cyano group, a carboxy group, a sulfo group, a sulfamoyl group, an N-alkylaminosulfonyl group, an N-phenylaminosulfonyl group, a C1 to C4 alkylsulfonyl group which may be substituted by a hydroxy group, a phosphono group, a nitro group, an acyl group, a ureide group, a C1 to C4 alkyl group which may be substituted by a group selected from the group consisting of a hydroxy group and a C1 to C4 alkoxy group, a C1 to C4 alkoxy group which may be substituted by a group selected from the group consisting of a hydroxy group, a C1 to C4 alkoxy group, a sulfo group and a carboxy group, an acylamino group, an alkylsulfonylamino group or a phenylsulfonylamino group wherein the phenyl group may be substituted by a group selected from the group consisting of a halogen atom, an alkyl group and a nitro group;

each of $R^{23}$, $R^{24}$, $R^{25}$, $R^{26}$, $R^{27}$, $R^{28}$ $R^{29}$ and $R^{20}$ independently represents a hydrogen atom, a halogen atom, a hydroxy group, a cyano group, a carboxy group, a sulfo group, a sulfamoyl group, an N-alkylaminosulfonyl group, an N-phenylaminosulfonyl group, a C1 to C4 alkylsulfonyl group which may be substituted by a hydroxy group, a phosphono group, a nitro group, an acyl group, a ureide group, a C1 to C4 alkyl group which may be substituted by a hydroxy group or a C1 to C4 alkoxy group, a C1 to C4 alkoxy group which may be substituted by a hydroxy group, a C1 to C4 alkoxy group, a sulfo group or a carboxy group, an acylamino group, an alkylsulfonylamino group or a phenylsulfonylamino group wherein the phenyl group may be substituted by a halogen atom, an alkyl group or a nitro group; and n represents 0 or 1, respectively.

23. The water-based black ink composition according to claim 20, wherein (b) a dye having a maximum absorption wavelength in the range of 350 nm to 550 nm is a compound represented by the formula (5) or a salt thereof:

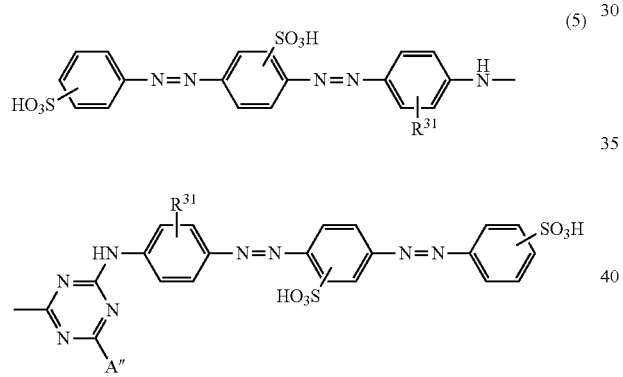

(5)

wherein, $R^{31}$ represents a hydrogen atom; a hydroxy group; a carboxy group; a C1 to C4 alkyl group which may be substituted by a hydroxy group or a C1 to C4 alkoxy group;

a C1 to C4 alkoxy group which may be substituted by a hydroxy group or a C1 to C4 alkoxy group; a C1 to C4 alkylamino group which may be substituted by a hydroxy group or a C1 to C4 alkoxy group; a carboxy C1 to C5 alkylamino group; a bis[carboxy C1 to C5 alkyl] amino group;

and a C1 to C4 alkanoylamino group which may be substituted by a hydroxy group or a C1 to C4 alkoxy group; a phenylamino group which may be substituted by a carboxy group, a sulfonic acid group or an amino group; a sulfo group; a halogen atom or a ureide group, and the group A" represents a substituted alkylamino group wherein the substituent on said alkyl group is a carboxy group or a sulfo group;

and (c) a dye having a maximum absorption wavelength in the range of 560 nm to 660 nm is a compound represented by the formula (II-2) or a salt thereof, Formula (II-2):

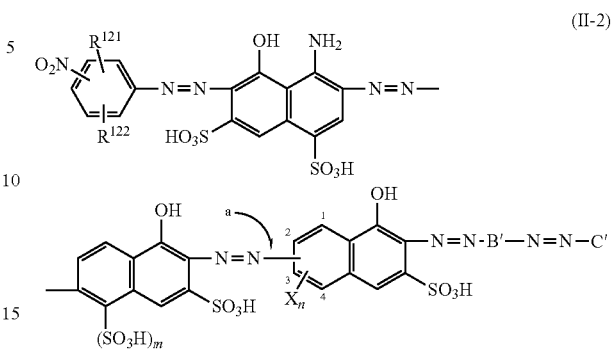

(II-2)

wherein, each of $R^{121}$ and $R^{122}$ independently represents a hydrogen atom, a halogen atom, a cyano group, a carboxy group, a sulfo group, a sulfamoyl group, an N-alkylaminosulfonyl group, an N-phenylaminosulfonyl group, a C1 to C4 alkylsulfonyl group which may be substituted by a hydroxy group, a phosphono group, a nitro group, an acyl group, a ureide group, a C1 to C4 alkyl group which may be substituted by a hydroxy group or a C1 to C4 alkoxy group, a C1 to C4 alkoxy group which may be substituted by a hydroxy group, a C1 to C4 alkoxy group, a sulfo group or a carboxy group, an acylamino group, an alkylsulfonylamino group or a phenylsulfonylamino group wherein the phenyl group may be substituted by a halogen atom, an alkyl group or a nitro group;

m represents 0 or 1, n represents 0 or 1, and

X represents a sulfo group, the group B' represents the following formula (II-3) or (II-4):

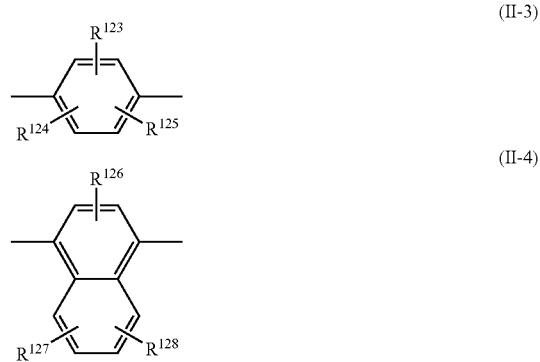

(II-3)

(II-4)

wherein, each of $R^{123}$, $R^{124}$, $R^{125}$, $R^{126}$, $R^{127}$ and $R^{128}$ independently represents a hydrogen atom, a halogen atom, a hydroxy group, a cyano group, a carboxy group, a sulfo group, a sulfamoyl group, an N-alkylaminosulfonyl group, an N-phenylaminosulfonyl group, a C1 to C4 alkylsulfonyl group which may be substituted by a hydroxy group, a phosphono group, a nitro group, an acyl group, a ureide group, a C1 to C4 alkyl group which may be substituted by a hydroxy group or a C1 to C4 alkoxy group, a C1 to C4 alkoxy group which may be substituted by a group selected from the group consisting of a hydroxy group, a C1 to C4 alkoxy group, a sulfo group and a carboxy group, an acylamino group, an alkylsulfonylamino group or a phenylsulfonylamino group wherein the phenyl group may be substituted by a group selected from the group consisting of a halogen atom, alkyl group and a nitro group;

the group C' is a substituted phenyl group or a substituted naphthyl group, and said phenyl or naphthyl group has a group selected from the group consisting of a hydroxy group, a halogen atom, a cyano group, a carboxy group, a sulfo group, a sulfamoyl group, an N-alkylaminosulfonyl group, an N-phenylaminosulfonyl group, a C1 to C4 alkylsulfonyl group which may be substituted by a hydroxy group, a phosphono group, a nitro group, an acyl group, a ureide group, a C1 to C4 alkyl group which may be substituted by a hydroxy group or a C1 to C4 alkoxy group, a C1 to C4 alkoxy group which may be substituted by a group selected from the group consisting of a hydroxy group, a C1 to C4 alkoxy group, a sulfo group and a carboxy group, an acylamino group, an alkylsulfonylamino group and a phenylsulfonylamino group wherein the phenyl group may be substituted by a group selected from the group consisting of a halogen atom, an alkyl group and a nitro group, as a substituent; respectively.

* * * * *